US006939670B2

(12) United States Patent
Pressman et al.

(10) Patent No.: US 6,939,670 B2
(45) Date of Patent: Sep. 6, 2005

(54) CELL-BASED DETECTION AND DIFFERENTIATION OF LUNG CANCER

(75) Inventors: Norman J. Pressman, Glencoe, IL (US); Kenneth S. Hirsch, deceased, late of Redwood City, CA (US); by Adrian Hirsch, legal representative, Redwood City, CA (US)

(73) Assignee: Monogen, Inc., Vernon Hills, IL (US)

( * ) Notice: Subject to any disclaimer, the term of this patent is extended or adjusted under 35 U.S.C. 154(b) by 301 days.

(21) Appl. No.: 10/095,297

(22) Filed: Mar. 12, 2002

(65) Prior Publication Data

US 2003/0104499 A1 Jun. 5, 2003

Related U.S. Application Data

(60) Provisional application No. 60/274,638, filed on Mar. 12, 2001.

(51) Int. Cl.⁷ .............................. C12Q 1/00; C12Q 1/68; G01N 33/50; G01N 33/53
(52) U.S. Cl. ................................ 435/4; 435/6; 435/7.1; 530/388.8; 530/389.7; 530/391.1; 536/24.31; 436/64
(58) Field of Search .................... 435/4, 6, 7.1; 436/64; 530/388.8, 389.7, 391.1, 387.1; 536/24.31

(56) References Cited

U.S. PATENT DOCUMENTS

| 4,579,827 A | 4/1986 | Sakamoto et al. |
| 4,853,770 A | 8/1989 | Schneller |
| 5,543,291 A | 8/1996 | Keyomarsi et al. |
| 5,731,162 A | 3/1998 | Gatti et al. |
| 5,997,866 A | 12/1999 | Johnson et al. |
| 6,007,996 A | 12/1999 | McNamara et al. |
| 6,335,170 B1 * | 1/2002 | Orntoft .......................... 435/6 |
| 2002/0192228 A1 * | 12/2002 | Hanash .................... 424/185.1 |

FOREIGN PATENT DOCUMENTS

| EP | 0 727 664 | 8/1996 |
| WO | WO87/06620 A1 | 11/1987 |
| WO | WO94/24560 A1 | 10/1994 |
| WO | WO98/28622 A1 | 7/1998 |
| WO | WO99/21014 | 4/1999 |
| WO | WO99/64631 | 12/1999 |
| WO | WO 00/55180 * | 9/2000 |
| WO | WO01/36674 A2 | 5/2001 |
| WO | WO02/08764 A1 | 1/2002 |

OTHER PUBLICATIONS

Roig et al (Anticancer Research, 1993, vol. 13, pp. 2457–2463).*
Burke et al (Human Pathology, 1999, vol. 30, pp. 158–167).*
60/121,124.*
Guddo et al (J Clin Pathol, 1998, vol. 51, pp. 667–671).*
Malusecka et al (Anticancer Research, 2001, 21, vol. 1015–1021).*
Dessy et al (Virchows Archive, Mar 2000, vol. 436, pp. 289–296).*
Puglisi et al (Cancer Letters, 2001, vol. 162, pp. 97–103).*
Schlom (Monoclonal Antibodies, In: Molecular Foundations of Oncology, 1991, pp. 95–134).*
Flam et al., "Immunohistochemical markers defined by monoclonal antibodies and response to bacillus Calmette–Gueriri endovesical immunotherapy for superficial bladder tumors", Abstract, European Urology, pp. 338–342, vol. 17, No. 4.
Duray et al., "Immunohistochemical phenotyping of malignant melanoma. A procedure whose time has come in pathology practice", Abstract, Pathology Annual, pp. 351–377, vol. 25 Pt 2, 1990.
Gazdar et al., "Biological, Molecular, and Clinical Markers for the Diagnosis and Typing of Lung Cancer", Abstract, Immunol. Ser, pp. 453–468, vol. 53, 1990.
Terada et al., "N–Ras Gene–Mutations in Childhood Acute Non–Lymphoblastic Leukemia", Abstract, Leukemia Research, pp. 935–941, vol. 15, No. 10, 1991.
Imamura et al., "Detection of High–Incidence of N–Ras Oncogene Point Mutations in Acute Myelogenous Leukemia", Abstract, American Journal of Hematology, pp. 151–153, vol. 43, No. 2, Jun. 1993.
Wood et al., "Immunocytochemical and Differentiation of Reactive Hyperplasia from Follicular Lymphoma Using Monoclonal Antibodies to Cell–Surface and Proliferation–Related Markers", Abstract, Applied Immunohistochemistry, pp. 48–53, vol. 2, Nol. 1, Spring 1994.
Jacquemier et al, "P53 Immunochemical Analysis in Breast–Cancer with 4 Monoclonal–Antibodies–Comparison of Stating and PCR–SSCP Results", Abstract, British Journal of Cancer, pp. 846–852, vol. 69, No. 5, May 1994.
Granberg et al, "Prognostic markers in bronchial carcinoid tumors", Abstract, Proc Annu Meet Am Assoc Cancer Res, vol. 38, A774, 1997.
Pastorino et al, "Immunochemical markers in stage I lung cancer: relevance to prognosis", Abstract, Journal of Clinical Oncology, pp. 2858–2865, vol. 15, No. 8, Aug. 1997.
Harpole et al, "A biological risk model for stage I lung cancer: Immunohistochemcial analysis of 408 patients with the use of ten molecular markers", Abstract, Journal of Thoracic and Cardiovascular Surgery, pp. 736–742, vol. 117, No. 4, Apr. 1999.

(Continued)

*Primary Examiner*—Karen A. Canella
(74) *Attorney, Agent, or Firm*—Foley & Lardner LLP

(57) ABSTRACT

The present invention provides a method for detecting and differentiating disease states with high sensitivity and specificity. The method allows for a determination of whether a cell-based sample contains abnormal cells and, for certain diseases, is capable of determining the histologic type of disease present. The method detects changes in the level and pattern of expression of the molecular markers in the cell-based sample. Panel selection and validation procedures are also provided.

4 Claims, 7 Drawing Sheets

OTHER PUBLICATIONS

Piao et al., "Frequent loss xq25 on the inactive X chromosome in primary breast carcinomas is associated with tumor grade and auxiliary lymph node status", Abstract, Genes, Chromosomes & Cancer, pp. 262–269, vol. 33, No. 3, Mar. 2002.

Fritsche et al., "Tumor markers and pattern recognition analysis: A new diagnostic tool for cancer", Abstract, Journal of Clinical Ligand Assay, pp. 11–15, vol. 25, Nol, 1, Spring 2002.

Wu et al., "Value of Combined determination of tumor marker for histological type of lung cancer by pattern recognition", Abstract, Henan Yilce Daxue Xuebao, pp. 214–217, vol. 35, No. 3, 2000.

Pohl et al., "Neural network evaluation of multiple tumor markers for diagnosis of ovarian cancer using three different sets of patients", Abstract, 3rd International Conference of the Mediterranean Society of Tumor Marker Oncology, Oct. 26–29, 1994.

Lansford et al., "Resolution of multiple green fluorescent protein color variants and dyes using two–photon microscopy and imaging spectroscopy", Abstract, Journal of Biomedical Optics, pp. 311–318, vol. 6, No. 3, Jul. 2001.

So et al., "Two–photon deep tissue ex vivo imaging of mouse dermal and subcutaneous structures", Abstract, Optics Express, pp. 339–350, vol. 3, No. 9, Oct. 26, 1998.

Tockman et al., "Sensitive and Specific Monoclonal Antibody Recognition of Human Lung Cancer Antigen or Preserved Sputum Cells: A New Approach to Early Lung Cancer Detection," Journal of Clinical Oncology, vol. 6, No. 11, Nov. 1988, pp. 1685–1693, XP000614978.

Lozano et al., "Immunocytochemistry in the Differential Diagnosis of Serous Effusions: A Comparative Evaluation of Eight Monoclonal Antibodies in Papanicolaou Stained Smears", Cancer Cytopathology, vol. 93, No. 1, Feb. 25, 2001, pp. 68–72, XP009002477.

Frisman et al., "Immunocytochemistry in the Differential Diagnosis of Effusions: Use of Logistic Regression to Select a Panel of Antibodies to Distinguish Adenocarcinomas from Mesothelial Proliferations," Modern Pathology, vol. 6, No. 2, 1993, pp. 179–184, XP009002474.

Leers et al., "E–Cadherin and Calretinin: A Useful Combination of Immunochemical Markers for Differentiation Between Mesothelioma and Metastatic Adenocarcinoma," Histopathology (Oxford), vol. 32, No. 3, Mar. 1998, pp. 209–216. XP002224146.

Skov et al., "Differentiation of Adenocarcinoma of the Lung and Malignant Mesothelioma: Predictive Value and Reproducibility of Immunoreactive Antibodies," Histopathology (Oxford), vol. 25, No. 5, 1994, pp. 431–437, XP009002475.

Neft et al., "Concurrent Fluorescence in Situ Hybridization and immunocytochemistry for the Detection of Chromosome Aberrations in Exfoliated Bronchial Epithelial Cells," ACTA Cytological, International Academy of Cytology, Chicago, IL, vol. 41, No. 6, 1997, pp. 1769–1773, XP000961317.

Gonzalez–Lois et al., "Combined Use of Novel Epithelial (MOC–31) and Mesothelial (HBME–1) Immunohistochemical Markers for Optimal First Line Diagnostic Distinction Between Mesothelioma and Metastatic Carcinoma in Pleura," Histopathology (Oxford), vol. 38, No. 6, Jun. 2001, pp. 528–534, XP002224147.

Kallakury et al., "The Prognostic Significance of Proliferation–Associated Nucleolar Protein p120 Expression in Prostate Adenocarcinoma: A Comparison with Cyclins A and B1, Ki–67, Proliferating Cell Nuclear Antigen, and $p34^{cdc2}$," CANCER, vol. 85, No. 7, Apr. 1, 1999, pp. 1569–1576, XP–002235530.

Mitas et al., "Quantitative Real–Time RT–PCR Detection of Breast Cancer Micrometastasis Using a Multigene Marker Panel," International Journal of Cancer, vol. 93, No. 2, 2001, pp. 162–171.

Volm et al., "Prognostic Value of ERBB–1, VEGF, Cyclin A, FOS, JUN and MYC in Patients with Squamous Cell Lung Carcinomas," British Journal of Cancer, vol. 77, No. 4, Feb. 1998, pp. 663–669, XP009007843.

Bejarano et al., "Surfactant Proteins and Thyroid Transcription Factor–1 in Pulmonary and Breast Carcinomas," Modern Pathology, vol. 9, No. 4, 1996, pp. 445–452, XP009007792.

Gaspar et al., "Quantitative Immunohistochemical Analyses of the Expression of E–Cadherin, Thrombomodulin, CD44H and CD44v6 in Primary Tumours of Pharynx/Larynx Squamous Cell Carcinoma and Their Lymph Node Matastases," Analytical Cellular Pathology, vol. 18, No. 4, 1999, pp. 183–190, XP009007804.

Fukuse et al., "Expression of Proliferating Cell Nuclear Antigen and CD44 Variant Isoforms in the Primary and Metastatic Sites of Nonsmall Cell Lung Carcinoma with Intrapulmonary Metastases," CANCER, vol. 86, No. 7, Oct. 1, 1999, pp. 1174–1181, XP002235532.

Aksien et al., "Oncoproteins and Tumor Progression in Papillary Thryoid Carcinoma: Presence of Epidermal Growth Factor Receptor Related Protein, p21–ras Protein, and Proliferation indicators in Relation to Tumor Recurrences and Patient Survival," CANCER (Philadelphia), vol. 76, No. 9, 1995, pp. 1643–1654, XP009007851.

Reis–Filho et al., "Evaluation of Cell Proliferation, Epidermal Growth Factor Receptor, and bcl–2 Immunoexpression as Prognostic Factors for Patients with World Health Organization Grade 2 Oligodendroglioma," *CANCER*, vol. 88, No. 4, pp. 862–869, XP002235533.

Pastorino et al., "Immunocytochemical Markers in Stage I Lung Cancer: Relevance of Prognosis," Journal of Clinical Oncology, vol. 15, No. 8, 1997, pp. 2858–2865, XP009007844.

Orchard et al., "Immunocytochemistry in the Diagnosis of Kaposi's Sarcoma and Angiosarcoma," British Journal of Biomedical Science, England, Mar. 1995, vol. 52, No. 1, pp. 35–49, XP009007990.

Piatti et al., "Fine Needle Aspiration Biopsy of Hepatocellular Carcinoma Resembling Neuroendocrine Tumor: A Case Report," ACTA Cytological, vol. 41, No. 2, Mar. 1997, pp. 583–586, XP009007979.

Dessy et al., "Surfactant Protein and Thyroid Transcription Factor 1 in Pleuro–Pulmonary Neoplasia," Immunohistochemical Study, Database Medline "Online", U.S. National Library of Medicine (NLM), Dec. 2000, Database Accession No. NLM11234300, XP002235534.

Lucas et al., "Ewing Sarcoma vs Lymphoblastic Lymphoma: A Comparative Immunohistochemical Study," American Journal of Clinical Pathology, vol. 115, No. 1, Jan. 2001, pp. 11–17, XP009007975.

Campana et al., "Immunophenotyping of Leukemia," Journal of Immunological Methods, Netherlands, vol. 243, No. 1–2, Sep. 21, 2000, pp. 59–75, XP004210693.

Goldberg–Kahn, et al. The cost of diagnosis: a comparison of four different strategies in the workup of solitary radiographic lung lesions. Chest 111, 870–6, (1997).

O'Donovan, The radiologic appearance of lung cancer. Oncology (Huntingt) 11, 1387–402; discussion 1402–4, (1997).

Worrell, Radiology of the central airways. Otolaryngol Clin North Am 28, 701–20, (1995).

Henschke, et al. Radiographic screening for cancer. Proposed paradigm for requisite research. Clin Imaging 18, 16–20, (1994).

Lam, et al. Localization of bronchial intraepithelial neoplastic lesions by fluorescence bronchoscopy. Chest 113, 696–702, (1998).

Sazon, et al. Fluorodeoxyglucose–positron emission tomography in the detection and staging of lung cancer. Am J Respir Crit Care Med 153, 417–21, (1996).

Lowe, et al. Optimum scanning protocol for FDG–PET evaluation of pulmonary malignancy. J Nucl Med 36, 883–7, (1995).

Lowe, et al. Prospective investigation of positron emission tomography in lung nodules. J Clin Oncol 16, 1075–84, (1998).

Raab, et al. The importance of sputum cytology in the diagnosis of lung cancer: a cost–effectiveness analysis. Chest 112, 937–45, (1997).

Franklin, New molecular and cellular approaches to lung cancer detection. In: Biology of Lung Cancer, pp. 529–570, (1998).

Kern, The diagnostic accuracy of sputum and urine cytology. Acta Cytol 32, 651–4, (1988).

Mehta, et al. Sputum cytology. Clin Chest Med 14, 69–85, (1993).

Gleohill, et al. Sputum cytology: a limited role. J Clin Pathol 50, 566–8, (1997).

Steffee, et al. Changing cytologic and histologic utilization patterns in the diagnosis of 515 primary lung malignancies. Cancer 81, 105–15, (1997).

Zaman, Pulmonary cytology. Clin Lab Med 11, 293–315.

Flehinger, et al. Current status of screening for lung cancer. Chest Surg Clin N Am 4, 1–15, (1994).

Koss, et al. Pulmonary cytology: A brief survey of diagnostic results from Jul. 1st, 1952 until Dec. 31st, 1960, Acta Cytol 8, 104, (1964).

Saccomanno, et al. Concentration of carcinoma or atypical cells in sputum. Acta Cytol 5, 305–310. (1963).

Miura, et al. Sputum cytology–positive, bronchoscopically negative adenocarcinoma of the lung [see comments]. Chest 102, 1328–32, (1992).

Valatis, et al. Increased incidence of adenocarcinoma of the lung. Cancer 47, 1042–1046, (1981).

Baldini, et al. Women and lung cancer: waiting to exhale, Chest 112, 229S–234S, (1997).

Caldwell, et al. Is the incidence of primary adenocarcinoma of the lung increasing? Virchows Arch 429, 359–63, (1996).

Risse, et al. Relationship between the cellular composition of sputum and the cytologic diagnosis of lung cancer. Acta Cytol 31, 170–6, (1987).

Holiday, et al. Sputum cytology within and across laboratories. A reliability study. Acta Cytol 39, 195–206, (1995).

Eddy, Screening for lung cancer [see comments]. Ann Intern Med 111, 232–7, (1989).

Younes, et al. Overexpression of Glut1 and Glut3 in stage I nonsmall cell lung carcinoma is associated with poor survival. Cancer 80, 1046–51, (1997).

Ogawa, et al. Glucose–transporter–type–I–gene amplification correlates with slalyl–Lewis–X synthesis and proliferation in lung cancer. Int J Cancer 74, 189–92, (1997).

Ito, et al. Expression of facilitative glucose transporter isoforms in lung carcinomas: its relation to histologic type, differentiation grade, and tumor state [see comments]. Mod Pathol 11, 437–43, (1998).

Sosolik, et al. Anti–MOC–31: a potentiz! addition to the pulmonary adenocarcinoma versus mesothelioma immunohistochemistry panel. Mod Pathol 10, 716–9, (1997).

Ordonez, Value of the MOC–31 monoclonal antibody in differentiating epithelial pleural mesothelioma from lung adenocarcinoma. Hum Pathol 29, 166–9, (1998).

Takanami, et al. The basic fibroblast growth factor and its receptor in pulmonary adenocarcinomas: an investigation of their expression as prognostic markers. Eur J Cancer 32A, 1504–9, (1996).

Takanami, et al. Immunohistochemical detection of basic fibroblast growth factor as a prognostic indicator in pulmonary adenocarcinoma. Jpn J Clin Oncol 26, 293–7, (1996).

Ohta, et al. Significance of vascular endothelial growth factor messenger RNA expression in primary lung cancer. Clin Cancer Res 2, 1411–6 1996, (1996).

Volm, et al. Prognostic value of basic fibroblast growth factor and its receptor (FGFR–1) in patients with non–small cell lung carcinomas. Eur J Cancer 33, 691–3, (1997).

Hiyama, et al. Telomerase activity in small–cell and non–small–cell lung cancers [see comments]. J Natl Cancer Inst 87, 895–902, (1995).

Yashima, et al. Telomerase expression in respiratory epithelium during the multistage pathogenesis of lung carcinomas. Cancer Res 57, 2373–7, (1997).

Ahrendt, et al. Comparison of oncogene mutation detection and telomerase activity for the molecular staging of non–small cell lung cancer. Clin Cancer Res 3, 1207–14, (1997).

Albanell, et al. High telomerase activity in primary lung cancers: association with increased cell proliferation rates and advanced pathologic stage. J Natl Cancer Inst 89, 1609–15, (1997).

Hiyama, et al. Telomerase activity as a novel marker of lung cancer and immune–associated lung diseases. Int J Mol Med 1, 545–9, (1998).

Yahata, et al. Telomerase activity in lung cancer cells obtained from bronchial washings. J Natl Cancer Inst 90, 684–90, (1998).

Lee, et al. Telomerase activity in lung cancer cell lines and tissues. Lung Cancer 21, 99–103, (1998).

Arai, et al. Application of telomerase activity for screening of primary lung cancer in broncho–alveolar lavage fluid. Oncol Rep 5, 405–8, (1998).

Fujii, et al. Prognostic significance of proliferating cell nuclear antigen (PCNA) expression in non–small cell lung cancer. Acta Med Okayama 47, 103–8, (1993).

Kawai, et al. Proliferating cell nuclear antigen and Ki–67 in lung carcinoma. Correlation with DNA flow cytometric analysis. Cancer 74, 2468–75, (1994).

Ogawa, et al. Blood vessel invasion and expression of sialyl Lewisx and proliferating cell nuclear antigen in stage I non–small cell lung cancer. Relation to postoperative recurrence. Cancer 73, 1177–83, (1994).

Ebina, et al. Relationship of p53 overexpression and up-regulation of proliferating cell nuclear antigen with the clinical course of non-small cell lung cancer. Cancer Res 54, 2496–503, (1994).

Fontanini, et al. Human non-small cell lung cancer: p53 protein accumulation is an early event and persists during metastatic progression [see comments]. J Pathol 174, 23–31, (1994).

Wiethege, et al. P53 accumulation and proliferating-cell nuclear antigen expression in human lung cancer. J Cancer Res Clin Oncol 121, 371–7, (1995).

Esposito, et al. Prognostic value of p53 in non-small cell lung cancer: relationship with proliferating cell nuclear antigen and cigarette smoking. Hum Pathol 28, 233–7, (1997).

Caputi, et al. Prognostic role of proliferating cell nuclear antigen in lung cancer: an immunohistochemical analysis. In Vivo 12, 85–8, (1998).

Hirata, et al. Expression of CD44 variant exon 6 in stage I non-small cell lung carcinoma as a prognostic factor. Cancer Res 58, 1108–10, (1998).

Ariza, et al. Standard and variant CD44 isoforms are commonly expressed in lung cancer of the non-small cell type but not of the small cell type. J Pathol 177, 363–8, (1995).

Fasano, et al. CD44 and its v6 spliced variant in lung tumors: a role in histogenesis? Cancer 80, 34–41, (1997).

Miyoshi, et al. The expression of the CD44 variant exon 6 is associated with lymph node metastasis in non-small cell lung cancer, Clin Cancer Res 3, 1289–97, (1997).

Tran, et al. Expression of CD44 standard form and variant isoforms in non-small cell lung carcinomas. Hum Pathol 28, 809–14, (1997).

Takigawa, et al. Serum CD44 levels in patients with non-small cell lung cancer and their relationship with clinico-pathological features. Lung Cancer 18, 147–5 7, (1997).

Kondo, et al. High frequency expressions of CD44 standard and variant forms in non- small cell lung cancers, but not in small cell lung cancers. J Surg Oncol 69, 128–36, (1998).

Sasaki, et al. Expression of CD44 splicing isoforms in lung cancers: dominant expression of CD44v8–10 in non-small cell lung carcinomas. Int J Oncol 12, 525–33, (1998).

Volm, et al. Cyclin A is associated with an unfavourable outcome in patients with non-small-cell lung carcinomas. Br J Cancer 75, 1774–8, (1997).

Dobashi, et al. Active cyclin A–CDK2 complex, a possible critical factor for cell proliferation in human primary lung carcinomas, Am J Pathol 153, 963–72, (1998).

Volm, et al. Prognostic value of ERBB–1, VEGF, cyclin A, FOS, JUN and MYC in patients with squamous cell lung carciomas [published erratum appears in Br J Cancer Apr. 1998; 77(7):1198]. Br J Cancer 77, 663–9, (1998).

Shoji, et al. Tumor extension and cell proliferation in adenocarcinomas of the lung. Am J Pathol 154, 909–18, (1999).

Shapiro, et al. Reciprocal Rb inactivation and p16INK4 expression in primary lung cancers and cell lines. Cancer Res 55, 505–9, (1995).

Betticher, et al. Prognostic significance of CCND1 (cyclin D1) overexpression in primary resected non-small-cell lung cancer. Br J Cancer 73, 294–300, (1996).

Mate, et al. Cyclin D1 overexpression in non-small cell lung carcinoma: correlation with Ki67 labelling index and poor cytoplasmic differentiation. J Pathol 180, 395–9, (1995).

Yang, et al. Cyclin D1 protein expression in lung cancer. Yonsei Med J 37, 142–50, (1996).

Betticher, et al. Abnormal expression of CCND 1 and RB 1 in resection margin epithelia of lung cancer patients. Br S Cancer 75, 1761–8, (1997).

Nishio, et al. Prognostic significance of cyclin D1 and retinoblastoma expression in combination with p53 abnormalities in primary, resected non-small cell lung cancers. Clin Cancer Res 3, 1051–8, (1997).

Caputi, et al. Prognostic role of cyclin D1 in non small cell lung cancer: an immunohistochemical analysis. Eur S Histochem 41, 133–8, (1997).

Betticher, et al. G1 control gene status is frequently altered in resectable non-small cell lung cancer. Int J Cancer 74, 556–62, (1997).

Volm, et al. Clinical implications of cyclins, cyclin-dependent kinases, RB and E2F1 in squamous-cell lung carcinoma. Int J Cancer 79, 294–9, (1998).

Kurasono, et al. Expression of cyclin D1, retinoblastoma gene protein, and p16 MTS1 protein in atypical adenomatous hyperplasia and adenocarcinoma of the lung. An immunohistochemical analysis. Virchows Arch 432, 207–15, (1998).

Tanaka, et al. Disruption of the RB pathway and cell-proliferative activity in non-small-cell lung cancers. Int J Cancer 79, 111–5, (1998).

Olivero, et al. Overexpression and activation of hepatocyte growth factor/scatter factor in human non-small-cell lung carcinomas. Br J Cancer 74, 1862–8, (1996).

Harvey, et al. Immunoreactivity for hepatocyte growth factor/scatter factor and its receptor, met, in human lung carcinomas and malignant mesotheliomas. J Pathos 180, 389–94, (1996).

Takanami, et al. Hepatocyte growth factor and c-Met/hepatocyte growth factor receptor in pulmonary adenocarcinomas: an evaluation of their expression as prognostic markers. Oncology 53, 392–7, (1996).

Siegfried, et al. The clinical significance of hepatocyte growth factor for non-small cell lung cancer. Ann Thorac Surg 66, 1915–8, (1998).

Nguyen, et al. Membrane-bound (MUC1) and secretory (MUC2, MUC3, and MUC4) mucin gene expression in human lung cancer. Tumour Biol 17, 176–92, (1996).

Yu, et al. Overexpression of MIJC5 genes in associated with early post-operative metastasis in nonsmall-cell lung cancer. Int J Cancer 69, 45 7–65, (1996).

Yu, et al. Sialomucin expression is associated with erbB–2 oncoprotein overexpression, early recurrence, and cancer death in non-small-cell lung cancer [published erratum appears in Am J Respir Crit Care Med Aug. 1997;156(2Pt1):677–8]. Am J Respir Crit Care Med 155, 1419–27, (1997).

Jarrad, et al. MUC1 is a novel marker for the type II pneumocyte lineage during lung carcinogenesis. Cancer Res 58, 5582–9, (1998).

Ohgami, et al. MUC1 mucin mRNA expression in stage I lung adenocarcinoma and its association with early recurrence. Ann Thorac Surg 67, 810–4, (1999).

Bejarano, et al. Surfactant proteins and thyroid transcription factor–1 in pulmonary and breast carcinomas. Mod Pathol 9, 445–52, (1996).

Harlamert, et al. Thyroid transcription factor–1 and cytokeratins 7 and 20 in pulmonary and breast carcinoma. Acta Cytol 42, 1382–8, (1998).

Fontanini, et al. Neoangiogenesis and p53 protein in lung cancer: their prognostic role and their relation with vascular endothelial growth factor (VEGF) expression [see comments]. Br J Cancer 75, 1295–301, (1997).

Shibusa, et al. Tumor angiogenesis and vascular endothelial growth factor expression in stage I lung adenocarcinoma. Clin Cancer Res 4, 1483–7, (1998).

Giatromanolaki, et al. Vascular endothelial growth factor, wild–type p53, and angiogenesis in early operable non–small cell lung cancer. Clin Cancer Res 4, 3017–24, (1998).

Fontanini, et al. Bcl2 and p53 regulate vascular endothelial growth factor (VEGF)– mediated angiogenesis in non–small cell lung carcinoma. Eur J Cancer 34, 718–23, (1998).

Takahama, et al. Frequent expression of the vascular endothelial growth factor in human non–small–cell lung cancers, Jpn J Clin Oncol 28, 176–81, (1998).

Sozzi, et al. Cytogenetic abnormalities and overexpression of receptors for growth factors in normal bronchial epithelium and tumor samples of lung cancer patients. Cancer Res 51, 400–4, (1991).

Volm, et al. Overexpression of c–fos and c–erbB1 encoded proteins in squamous cell carcinomas of the lung of smokers. Int J Oncol 1, 69–71, (1992).

Wodrich, et al. Overexpression of oncoproteins in non–small cell lung carcinomas of smokers. Carcinogenesis 14, 1121–4, (1993).

Pastorino, et al. Genetic changes in lung cancer. J Cell Biochem Suppl 17F, 237–48, (1993).

Gorgoulis, et al. Molecular and immunohistochemical study of class I growth factor receptors in squamous cell lung carcinomas. Pathol Res Pract 191, 973–81, (1995).

Rusch, et al. Aberrant expression of p53 or the epidermal growth factor receptor is frequent in early bronchial neoplasia and coexpression precedes squamous cell carcinoma development, Cancer Res 55, 1365–72, (1995).

Rusch, et al. Molecular biologic features of non–small cell lung cancer. Clinical Implications. Chest Surg Clin N Am 5, 39–55, (1995).

Fontanini, et al. Epidermal growth factor receptor (EGFr) expression in non–small cell lung carcinomas correlates with metastatic involvement of hilar and mediastinal lymph nodes in the squamous subtype. Eur J Cancer 31A, 178–83, (1995).

Pflug, et al. Expression of the low affinity nerve growth factor receptor in prostate epithelial cells negatively regulates nerve growth factor– mediated growth via induction of apoptosis (Meeting abstract). Proc Annu Meet Am Assoc Cancer Res 37, A262, (1996).

Rusch, et al. Overexpression of EGFR and TGF–alpha is frequent in early stage non– small cell lung cancer, but does not predict tumor progression (Meeting abstract). Proc Annu Meet Am Assoc Cancer Res 37, A1314, (1996).

Fujino, et al. A comparison of epidermal growth factor receptor levels and other prognostic parameters in non–small cell lung cancer. Eur J Cancer 32A, 2070–4, (1996).

Pastorino, et al. Immunocytochemical markers in stage I lung cancer: relevance to prognosis. J Clin Oncol 15, 2858–65, (1997).

Sekine, et al. Role of epidermal growth factor receptor overexpression, K–ras point mutation and c–myc amplification in the carcinogenesis of non–small cell lung cancer. Oncol Rep 5, 351–4, (1998).

Pfeiffer, et al. Enzyme–linked immunosorbent assay of epidermal growth factor receptor in lung cancer: comaprisons with immunohistochemistry, clinicopathological features and prognosis. Br J Cancer 78, 96–9, (1998).

d'Amico, et al. A biological risk model for stage I lung cancer: immunohistochemical analysis of 408 patients with the use of ten molecular markers. J Thorac Cardiovasc Surg 117, 736–43, (1999).

Engel, et al. High levels of nm23–H1 and nm23–H2 messenger RNA in human squamous–cell lung carcinoma are associated with poor differentiation and advanced tumor stages. Int J Cancer 55, 375–9, (1993).

Ozeki, et al. Immunohistochemical analysis of nm23/NDP kinase expression in human lung adenocarcinoma: association with tumor progression in Clara cell type. Jpn J Cancer Res 85, 840–6, (1994).

Lai, et al. Immunohistochemical analysis of nm23–H1 in state I non–small cell lung cancer: a useful marker in prediction of metastases. Ann Thorac Surg 62, 1500–4, (1996).

Gazzeri, et al. Overexpression of nucleoside diphosphate/kinase A/nm23–H1 protein in human lung tumors: association with tumor progression in squamous carcinoma. Lab Invest 74, 158–67, (1996).

Mackinnon, et al. p53, c–erbB–2 and nm23 expression have no prognostic significance in primary pulmonary adenocarcinoma. Eur J Cardiothorac Surg 11, 838–42, (1997).

Bosnar, et al. Squamous cell lung carcinomas: the role of nm23–H1 gene. J Mol Med 75, 609–13, (1997).

Kawakubo, et al. Expression of nm23 protein in pulmonary adenocarcinomas: inverse correlation to tumor progression. Lung Cancer 17, 103–13, (1997).

Ritter, et al. Expression of bcl–2 protein in stage T1N0M0 non–small cell lung carcioma. Hum Pathol 26, 1227–32, (1995).

Kitagawa, et al. Overexpression of Bcl–2 and mutations in p53 and K–ras in resected human non–small cell lung cancers. Am J Respir Cell Mol Biol 15, 45–54, (1996).

Rao, et al. Immunohistochemical detection of bcl–2 protein in adenocarcinoma and non–neoplastic cellular compartments of the lung. Mod Pathol 9, 555–9, (1996).

Boers, et al. P53 in squamous metaplasia: a marker for risk of respiratory tract carcinoma. Am J Respir Crit Care Med 153, 411–6, (1996).

Coppola, et al. Bcl–2, p53, CD44, and CD44v6 isoform expression in neuroendocrine tumors of the lung. Mod Pathol 9, 484–90, (1996).

Higashiyama, et al. Bcl–2 oncoprotein expression is increased especially in the portion of small cell carcinoma within the combined type of small cell lung cancer. Tumour Biol 17, 341–4, (1996).

Strauss, G.M. Prognostic markers in resectable non–small cell lung cancer. Hematol Oncol Clin North Am 11, 409–34, (1997).

Anton, et al. Absence of prognostic significance of bcl–2 immunopositivity in non– small cell lung cancer: analysis of 427 cases. Hum Pathol 28, 1079–82, (1997).

Ishida, et al. The prognostic significance of p53 and bcl–2 expression in lung adenocarcinoma and its correlation with Ki67 growth fraction. Cancer 80, 1934–45, (1997).

Stefanaki, et al. Immunohistochemical detection of bcl2, p53, mdm2 and p21/waf1 proteins in small–cell lung carcinomas. Anticancer Res 18, 1167–73, (1998).

Brambilla, et al. p53 mutant immunophenotype and deregulation of p53 transcription pathway (Bcl2, Bax, and Wafl) in precursor bronchial lesions of lung cancer. Clin Cancer Res 4, 1609–16, (1998).

Salgia, et al. Molecular abnormalities in lung cancer. J Clin Oncol 16, 1207–17, (1998).

Kim, et al. The interactive effect of Ras, HER2, P53 and Bcl–2 expression in predicting the survival of non–small cell lung cancer patients. Lung Cancer 22, 181–90, (1998).

Groeger, et al. Bcl–2 protein expression correlates with nodal status in non small cell lung cancer. Anticancer Res 19, 821–4, (1999).

Vargas, et al. Estrogen–receptor–related protein p29 in primry nonsmall cell lung carcinoma: pathologic and prognostic correlations. Cancer 82, 1495–500, (1998).

Higashiyama, et al. Retinoblastoma protein expression in lung cancer: an immunohistochemical analysis. Oncology 51, 544–51, (1994).

Xu, et al. Altered retinoblastoma protein expression and prognosis in early stage non–small cell lung carcinoma. J. Natl. Cancer Inst. 86, 695–699, (1994).

Lee, et al. Prognostic significance of retinoblastoma protein expression in non–small cell lung cancer (Meeting abstract). Proc Annu Meet Am Assoc Cancer Res 36, A3787, (1995).

Dixon, et al. Expression of the retinoblastoma protein in normal and dysplastic bronchial epithelium and lung cancer (Meeting abstract). J Pathol 176, 32A, (1995).

Shapiro, et al. Reciprocal Rb inactivation and p16 expression in lung cancer (Meeting abstract). Proc Annu Meet Am Assoc Cancer Res 36, A164, (1995).

Volm, et al. Retinoblastoma (Rb) protein expression and resistance in squamous cell lung carcinomas. Anticancer Res 16, 891–4, (1996).

Dosaka–Akita, et al. Prognostic significance of Rb protein expression in non–small cell lung cancer (NSCLC) (Meeting abstract). Proc Annu Meet Am Assoc Cancer Res 37, A1401 (1996).

Kinoshita, et al. Significance of abnormal pl6INK4 and RB protein expression in non– small cell lung cancer (NSCLC) (Meeting abstract). Proc Annu Meet Am Assoc Cancer Res 37, A3979, (1996).

Kratzke, et al. Rb and p16INK4a expression in resected non–small cell lung tumors. Cancer Res 56, 3415–20, (1996).

Sakaguchi, et al. Inversely correlated expression of p16 and Rb protein in non–small cell lung cancers: an immunohistochemical study. Int J Cnacer 65, 442–5, (1996).

Xu, et al. Altered retinoblastoma and p53 protein status in non–small cell carcinoma of the lung: potential synergistic effects on prognosis. Clin Cancer Res 2, 1169–76, (1996).

Dosaka–Akita, et al. Altered retinoblastoma protein expression in non–small cell lung cancer: Its synergistic effects with altered ras and p53 protein status on prognosis. Cancer 79, 1329–37, (1997).

Cagle, et al. Differential retinoblastoma protein expression in neuroendocrine tumors of the lung. Potential diagnostic implications. Am J Pathol 150, 393–400, (1997).

Kashiwabara, et al. Correlation between methylation status of the p16/CDKN2 gene and the expression of p16 and Rb proteins in primary non–small cell lung cancers. Int J Cancer 79, 215–20, (1998).

Caputi, et al. RB growth control evasion in lung cancer. Anticancer Res 18, 2371–4, (1998).

Tamura, et al. Detection of thrombomodulin in human lung cancer cells. Am J Pathol 142, 79–85, (1993).

Tamura, et al. Is thrombomodulin useful as a tumor marker of a lung cancer? Lung Cancer 15, 189–95, (1996).

Collins, et al. Thrombomudulin expression in malignant pleural mesothelioma and pulmonary adenocarcinoma. Am J Pathol 141, 827–33, (1992).

Hamatake, et al. Prognostic value and clinicopathological correlation of thrombomodulin in squamous cell carcinoma of the human lung. Clin Cancer Res 2, 763–6, (1996).

Ordonez, N.G. Value of thrombomodulin immunostaining in the diagnosis of mesothelioma. Histopathology 31, 25–30, (1997).

Tolnay, et al. Expression and localization of thrombomodulin in preneoplastic bronchial lesions and in lung cancer. Virchows Arch 430, 209–12, (1997).

Bohm, et al. Differences of E–cadherin expression levels and patterns in human lung cancer. Ann Hematol 68, 81–3, (1994).

Bohm, et al. Differences of E–cadherin expression levels and patterns in primary and metastatic human lung cancer. Clin Exp. Metastasis 12, 55–62, (1994).

Soler, et al. The differential expression of N–cadherin and E–cadherin distinguishes pleural mesotheliomas from lung adenocarcinomas [see comments]. Hum Pathol 26, 1363–9, (1995).

Han, et al. Differential expression of N–cadherin in pleural mesotheliomas and E–cadherin in lung adenocarcinomas in formalin–fixed, paraffin–embedded tissues [see comments]. Hum Pathol 28, 641–5, (1997).

Weynants, et al. Expression of mage genes by non–small–cell lung carcinomas. Int J Cancer 56, 826–9, (1994).

Shichijo, et al. Detection of MAGE–4 protein in lung cancers. Int J Cancer 64, 158–65, (1995).

Sakata, M. Expression of MAGE gene family in lung cancers. Kurume Med J 43, 55–61, (1996).

Fischer, et al. High expression of MAGE–3 protein in aquamous–cell lung carcinoma [letter]. Int J Cancer 71, 1119–21, (1997).

Gotoh, et al. Frequency of MAGE–3 gene expression in HLA–A2 positive patients with non–small cell lung cancer. Lung Cancer 20, 117–25, (1998).

Uchiyama, et al. Expression of nucleolar protein p120 in human lung cancer: difference in histological types as a marker for proliferation. Clin Cancer Res 3, 1873–7, (1997).

Singh, et al. The pathobiologic features of carcinomas of type II pneumocytes. An immunocytologic study. Cancer 57, 994–9, (1986).

Mizutani, et al. Immunohistochemical localization of pulmonary surfactant apoproteins in various lung tumors. Special reference to nonmucus producing lung adenocarcinomas. Cancer 61, 532–7, (1988).

Noguchi, et al. Immunohistomchemical distinction of malignant mesothelioma from pulmonary adenocarcinoma with anti–surfactant apoprotein, anti– Lewisa, and anti–Tn antibodies. Hum Pathol 20, 53–7, (1989).

Linnoila, et al. Peripheral airway cell marker expression in non–small cell lung carcinoma. Association with distinct clinicopathologic features [see comments]. Am J Clin Pathol 97, 233–43, (1992).

Shijubo, et al. Pulmonary surfactant protein A in pleural effusions. Cancer 69, 2905–9, (1992).

Shijubo, et al. Lung surfactant protein–A and carcinoembryonic antigen in pleural effusions due to lung adenocarcinoma and malignant mesothelioma. Eur Respir J 8, 403–6, (1995).

Nicholson, et al. The value of PE–10, a monoclonal antibody against pulmonary surfactant, in distinguishing primary and metastatic lung tumours. Histopathology 27, 57–60.

Khoor, et al. Expression of surfactant protein B precursor and surfactant protein B mNA in adenocarcinoma of the lung. Mod Pathol 10, 62–7, (1997).

Saitoh, et al. Detection of surfactant protein–A gene transcript in the cells from pleural effusion for the diagnosis of lung adenocarcinoma. Am J Med 103, 400–4, (1997).

Grohs et al. Acta Cytologica, 1996, 40(1):26–30.

Grohs et al. Acta Cytologica, 1997, 41(1):144–152.

Phillips et al., "Three–dimensional imaging of embryonic mouse kidney by two–photon microscopy", Abstract, American Journal of Pathology, pp. 49–55, vol. 158, No. 1, Jan. 2001.

Osaka et al., "Expression of a novel antiapoptosis gene, survivin, correlated with tumor cell apoptosis and p53 accumulation in gastric carcinomas", Abstract, Cancer Research, pp. 1808–1812, vol. 58, No. 9, May 1, 1998.

Santella et al., Quantitation of exposure to benzo(a)pyrene with monoclonal antibodies, Abstract, Environ. Health Perspect., pp. 95–99, vol. 62, 1985.

Lawry et al., "The idenfitication of informative parameters in the flow cytometric analysis of breast carcinoma", Abstract, European Journal of Cancer, pp. 719–723, vol. 29A, No. 5, 1993.

Brotherick et al., "P53 expression measured by flow–cytometry– a comparison of 3 monoclonal–antibodies and the relationship with grade and DNA–ploidy in breast cancer", Abstract, Cancer Immunology Immunotherapy, pp. 146–150, vol. 41, No. 3, Sep. 1995.

Harrison et al., "Comparison of chromosome 1 aneusomy detected by interphase cytogenetics and DNA ploidy in carcinoma of the breast", Abstract, Histopathology, pp. 221–226, vol. 30, No. 3, May. 1997.

Ossewaarde et al., "Comparison of two panels of monoclonal antibodies for determination of Chlamydia trachomatis serovars", Abstract, Journal of Clinical Microbiology, pp. 2968–2974, vol. 32, Nol. 12, 1994.

Goldstein et al., "Specific diagnosis of herpesvirus with monoclonal antibodies; hybridoma construction and monoclonal antibody preparation", Abstract, Annu. Meet. Am. Soc. Microbiol., p. 292, vol. 83, 1983.

Tockman et al., "Considerations in Bringing A Cancer Biomaker To Clinical Application," Cancer Research, vol. 52, May 1, 1992, pp. 2711s–2718s.

Sherman, "Oncogenes And Tumor Suppressor Genes As Targets For Cancer Diagnosis And Therapy," Molecular Foundations Of Oncology, Broader, Ed., 1991, pp. 435–446.

* cited by examiner

Figure 1

| Squamous Cell Carcinoma | | Adenocarcinoma | | Large Cell Carcinoma | | Small Cell Carcinoma | | Mesothelioma | |
|---|---|---|---|---|---|---|---|---|---|
| Marker | (%) | Marker | (%) | Marker | (%) | Marker | (%) | Marker | (%) |
| Glut1 | 100.0 | MOC-31 | 100.0 | VEGF | 100.0 | MOC-31 | 100.0 | HGF | 100.0 |
| MOC-31 | 100.0 | MUC-1 | 90.0 | MUC-1 | 100.0 | FGF | 100.0 | N-Cadherin | 94.0 |
| FGF | 83.0 | Telomerase | 86.3 | HGF | 100.0 | MUC-1 | 100.0 | Thrombomodulin | 81.0 |
| Telomerase | 82.3 | HGF | 78.3 | EGF Receptor | 96.0 | E-Cadherin | 100.0 | | |
| PCNA | 80.0 | Thyroid Transcription Factor | 76.0 | Telomerase | 93.0 | Cyclin A | 97.0 | | |
| CD44v6 | 79.3 | | | PCNA | 87.7 | Bcl-2 | 92.0 | | |
| Cyclin A | 79.0 | | | Cyclin A | 83.5 | Cyclin D1 | 90.0 | | |
| HGF | 75.5 | | | nm23-H1 | 83.5 | Rb (loss) | 85.3 | | |
| | | | | Glut1 | 80.5 | Thyroid Transcription Factor | 83.0 | | |

Figure 2

| Marker | SQ/AD | SQ/LC | SQ/SC | SQ/ME | AD/LC | AD/SC | AD/ME | LC/SC | LC/ME | SC/ME |
|---|---|---|---|---|---|---|---|---|---|---|
| N-Cadherin | | | | | .04 | | | | | |
| Moc-31 | | | | 22.22 | | | 22.22 | | | 22.22 |
| FGF | | | | | | 0.49 | | 0.50 | | |
| MAGE-3 | 2.16 | | 2.15 | | | | | | | |
| Thrombomodulin | 5.64 | 17.20 | 688.00 | | | | 0.15 | | 0.05 | |
| VEGF | | | | | | | | 2.30 | | |
| MAGE-4 | 4.14 | | | | | 0.22 | | | | |
| Cyclin D1 | | | 0.47 | | | 0.40 | | | | |
| Thyroid Transcription Factor | 0.50 | | 0.46 | | | | | | | |
| Glut3 | | 0.44 | | | 0.41 | | | 4.39 | | |
| CD44v6 | 2.28 | | 793.00 | 690.00 | | 348.00 | 850.00 | 442.00 | | |
| E-Cadherin | | 2.27 | | | | | | 0.00 | | |
| Nucleolar Protein P120 | | | | | 0.47 | | | | | |
| EGF Receptor | | | .5 | | | .47 | | .46 | | |
| Bcl-2 | | | 2.73 | | | 2.12 | | | | |
| MAGE-1 | | | 0.24 | | | 0.31 | | 0.42 | | |
| Rb (Decreased) | 0.001 | | | | 615.00 | | | | | |
| Pulmonary Surfactant B | 0.23 | | | | 3.02 | 2.65 | 529 | | | |
| Pulmonary Surfactant A | | | | | | | | | | |

| Panel | Classifier | Test Pairs | Probe 1-28 | Area Under ROC |
|---|---|---|---|---|
| Detection | Decision Trees | Cancer vs control | | NA |
| | Stepwise LR | Cancer vs control | | 98.01 |
| | Stepwise LD | Cancer vs control | | 99.80% |
| | Common Probes (>= 2) | | | |
| Single Lung Cancer-type Specific Discrimination Against All Other Lung Cancers (Pair-wise Panels) | Decision Trees | Adeno vs others | | NA |
| | Stepwise LR | Adeno vs others | | 92.90% |
| | Stepwise LD | Adeno vs others | | 96.60% |
| | Common Probes (>= 2) | | | |
| | Decision Trees | Squamous vs others | | NA |
| | Stepwise LR | Squamous vs others | | 85.15% |
| | Stepwise LD | Squamous vs others | | 95.80% |
| | Common Probes (>= 2) | | | |
| | Decision Trees | Large Cell vs others | | NA |
| | Stepwise LR | Large Cell vs others | | 81.65% |
| | Stepwise LD | Large Cell vs others | | 78.20% |
| | Common Probes (>= 2) | | | |
| | Decision Trees | Mesothelioma | | NA |
| | Stepwise LR | Mesothelioma | | 93.72% |
| | Stepwise LD | Mesothelioma | | 99.20% |
| | Common Probes (>= 2) | | | |
| | Decision Trees | Small Cell vs others | | NA |
| | Stepwise LR | Small Cell vs others | | 98.13% |
| | Stepwise LD | Small Cell vs others | | 99.30% |
| | Common Probes (>=2) | | | |
| Joint Discrimination | Decision Trees | All simultaneously | | NA |

Key: Stepwise LR = Stepwise Logistic Regression; Stepwise LD = Stepwise Linear Discrimination

Figure 6

| Panel | Classifier | Test Pairs | \multicolumn{28}{c}{PROBE} |
|---|---|---|---|

| Panel | Classifier | Test Pairs | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|---|---|
| Detection | Decision Trees | Cancer vs control | X | | | | | | | | | X | | | | | | X | | | | | | | | | | | | |
| Detection | Stepwise LR | Cancer vs control | | | | X | | | | | | X | | | | | X | | | | | X | | | | X | | | | X | |
| Detection | Stepwise LD | Cancer vs control | X | | | | | X | | | | | | | | | | X | | | | | | | | | | | | |
| | Common Probes (>=2) | | ■ | | | | | | | | | ■ | | | | | | ■ | | | ■ | | | | ■ | | | | ■ | |

Figure 7

| Panel | | | PROBE | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | Classifier | Test Pairs | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| Detection | Decision Trees | Cancer vs control | | | | | X | X | | | | X | X | | | | | | | | | X | X | | | X | | | | | X |
| | Stepwise LR | Cancer vs control | | | | | | | | X | | X | | | | | | | | | X | | | | | X | | | | | | |
| | Stepwise LD | Cancer vs control | | | | | | | | | | | | | | | | | X | | X | X | | | | | | | | | | |
| | Common Probes (>= 2) | | | | | | | | | | | ■ | | | | | | | | | ■ | | | | | ■ | | | | | ■ |

CELL-BASED DETECTION AND DIFFERENTIATION OF LUNG CANCER

This application is a Continuation-in-Part of provisional application No. 60/274,638, filed Mar. 12, 2001, the entire contents of which are incorporated by reference herein.

BACKGROUND OF THE INVENTION

The present invention relates to early detection of a general disease state in a patient. The present invention also relates to discrimination (differentiation) between specific disease states in their early stages.

Early detection of a specific disease state can greatly improve a patient's chance for survival by permitting early diagnosis and early treatment while the disease is still localized and its pathologic effects limited anatomically and physiologically. Two key evaluative measures of any test or disease detection method are its sensitivity (Sensitivity= True Positives/(True Positives+False Negatives) and specificity (Specificity=True Negatives/(False Positives+True Negatives), which measure how well the test performs to accurately detect all affected individuals without exception, and without falsely including individuals who do not have the target disease. Historically, many diagnostic tests have been criticized due to poor sensitivity and specificity.

Sensitivity is a measure of a test's ability to detect correctly the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus (see Lewis, D. R. et al. "Molecular Diagnostics: The Genomic Bridge Between Old and New Medicine: A White Paper on the Diagnostic Technology and Services Industry" Thomas Weisel Partners, Jun. 13, 2001).

Specificity, on the other hand, is a measure of a test's ability to identify accurately patients who are free of the disease state. A test having poor specificity produces a high rate Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures treatments with their attendant risks, emotional and financial stresses, and which could have adverse effects on the patient's health. A feature of diseases which makes it difficult to develop diagnostic tests with high specificity is that disease mechanisms often involve a plurality of genes and proteins. Additionally, certain proteins may be elevated for reasons unrelated to a disease state. An example of a test that has high specificity is a gene-based test that can detect a p53 mutation. A p53 mutation will never be detected unless there are cancer cells present (see Lewis, D. R. et al. "Molecular Diagnostics: The Genomic Bridge Between Old and New Medicine: A White Paper on the Diagnostic Technology and Services Industry" Thomas Weisel Partners, Jun. 13, 2001).

Cellular markers are naturally occurring molecular structures within cells that can be discovered and used to characterize or differentiate cells in health and disease. Their presence can be detected by probes, invented and developed by human beings, which bind to markers enabling the markers to be detected through visualization and/or quantified using imaging systems. Four classes of cell-based marker detection technologies are cytopathology, cytometry, cytogenetics and proteomics, which are identified and described below.

Cytopathology relies upon the visual assessment by human experts of cytomorphological changes within stained whole-cell populations. An example is the cytological screening and cytodiagnosis of Papanicolaou-stained cervical-vaginal specimens by cytotechnologists and cytopathologists, respectively. Unlike cytogenetics, proteomics and cytometry, cytopathology is not a quantitative tool. While it is the state-of-the-art in clinical diagnostic cytology, it is subjective and the diagnostic results are often not highly sensitive or reproducible, especially at early stages of cancer (e.g., ASCUS, LSIL).

Tests that rely on morphological analyses involve observing a sample of a patient's cells under a microscope to identify abnormalities in cell and nuclear shape, size, or staining behavior. When viewed through a microscope, normal mature epithelial cells appear large and well differentiated, with condensed nuclei. Cells characterized by dysplasia, however, may be in a variety of stages of differentiation, with some cells being very immature. Finally, cells characterized by invasive carcinoma often appear undifferentiated, with very little cytoplasm and relatively large nuclei.

A drawback to diagnostic tests that rely on morphological analyses is that cell morphology is a lagging indicator. Since form follows function, often the disease state has already progressed to a critical stage by the time the disease becomes evident by morphological analysis. The initial stages of a disease involve chemical changes at a molecular level. Changes that are detectable by viewing cell features under a microscope are not apparent until later stages of the disease. Therefore, tests that measure chemical changes on a molecular level, referred to as "molecular diagnostic" tests, are more likely to provide early detection than tests that rely on morphological analyses alone.

Cytometry is based upon the flow-microfluorometric instrumental analysis of fluorescently stained cells moving in single file in solution (flow cytometry) or the computer-aided microscope instrumental analysis of stained cells deposited onto glass microscope slides (image cytometry). Flow cytometry applications include leukemia and lymphoma immunophenotyping. Image cytometry applications include DNA ploidy, Malignancy-Associated Changes (MACs) and S-phase analyses. The flow and image cytometry approaches yield quantitative data characterizing the cells in suspension or on a glass microscope slide. Flow and image cytometry can produce good marker detection and differentiation results depending upon the sensitivity and specificity of the cellular stains and flow/image measurement features used.

Malignancy-Associated Changes (MACs) have been qualitatively observed and reported since the early to mid- 1900's (O C Gruner: "Study of the changes met with leukocytes in certain cases of malignant disease" in Brit J Surg 3: 506–522, 1916) (H E Neiburgs, F G Zak, D C Allen, H Reisman, T Clardy: "Systemic cellular changes in material from human and animal tissues" in Transactions, 7th Ann Mtg Inter Soc Cytol Council, pp 137–144, 1959). From the mid-1900's through 1975, MACs were documented in independent qualitative histology and cytology studies in buccal mucosa and buccal smears (Nieburgs, Finch, Klawe), duodenum (Nieburgs), liver (Elias, Nieburgs), megakaryocytes (Ramsdahl), cervix (Nieburgs, Howdon), skin (Kwitiken), blood and bone marrow (Nieburgs), monocytes and leukocytes (van Haas, Matison, Clausen), and lung and sputum (Martuzzi and Oppen Toth). Before 1975 these qualitative studies reported MAC-based sensitivities for specific disease detection from 76% to 97% and specificities from 50% to 90%. In 1975 Oppen Toth reported a sensitivity of 76% and specificity of 81% in a qualitative sputum analysis study.

Quantitative observations regarding MAC-based probe analysis began two to three decades ago (H Klawe, J Rowinski: "Malignancy associated changes (MAC) in cells of buccal smears detected by means of objective image analysis" in Acta Cytol 18: 30–33, 1974) (G L Wied, P H Bartels, M Bibbo, J J Sychra: "Cytomorphometric markers for uterine cancer in intermediate cells" in Analyt Quant Cytol 2: 257–263, 1980) (G Burger, U Jutting, K Rodenacker: "Changes in benign population in cases of cervical cancer and its precursors" in Analyt Quant Cytol 3: 261–271, 1981). MACs were documented in independent quantitative histology and cytology studies in buccal mucosa and smears Klawe, Burger), cervix (Wied, Burger, Bartels, Vooijs, Reinhardt, Rosenthal, Boon, Katzke, Haroske, Zahniser), breast (King, Bibbo, Susnik), bladder and prostate (Sherman, Montironi), colon (Bibbo), lung and sputum (Swank, MacAulay, Payne), and nasal mucosa (Reith) studies with MAC-based sensitivities from 70% to 89% and specificities from 52% to 100%. Marek and Nakhosteen showed (1999, American Thoracic Society annual meeting) the results from two quantitative pulmonary studies showing (a) sensitivity of 89% and specificity of 92%, and (b) sensitivity of 91% and specificity of 100%.

Clearly, Malignancy-Associated Changes (MACs) are potentially useful probes that result from the image-cytometry marker detection technology. MAC-based features from DNA-stained nuclei can be used in conjunction with other molecular diagnostic probes to create optimized molecular diagnostic panels for the detection and differentiation of lung cancer and other disease states.

Cytogenetics detects specific chromosome-based intracellular changes using, for example, in situ hybridization (ISH) technology. ISH technology can be based upon fluorescence (FISH), multi-color fluorescence (M-FISH), or light-absorption-based chromogenics imaging (CHRISH) technologies. The family of ISH technologies uses DNA or RNA probes to detect the presence of the complementary DNA sequence in cloned bacterial or cultured eukaryotic cells. FISH technology can, for example, be used for the detection of genetic abnormalities associated with certain cancers. Examples include probes for Trisomy 8 and HER-2 neu. Other technologies such as polymerase chain reactions (PCR) can be used to detect B-cell and T-cell gene rearrangements. Cytogenetics is a highly specific marker detection technology since it detects the causative or "trigger" molecular event producing a pathology condition. It may be less sensitive than the other marker detection technologies because fewer events may be present to detect. In situ hybridization (ISH) is a molecular diagnostic method uses gene-based analyses to detect abnormalities on the genetic level such as mutations, chromosome errors or genetic material inserted by a specific pathogen. For example, in situ hybridization may involve measuring the level of a specific mRNA by treating a sample of a patient's cells with labeled primers designed to hybridize to the specific mRNA, washing away unbound primers and measuring the signal of the label. Due to the uniqueness of gene sequences, a test involving the detection of gene sequences will likely have a high specificity, yielding very few false positives. However, because the amount of genetic material in a sample of cells may be very low, only a very weak signal may be obtained. Therefore, in situ hybridization tests that do not employ pre-amplification techniques will likely have a poor specificity, yielding many false negatives.

Proteomics depends upon cell characterization and differentiation resulting from the over-expression, under-expression, or presence/absence of unique or specific proteins in populations of normal or abnormal cell types. Proteomics includes not only the identification and quantification of proteins, but also the determination of their localization, modifications, interactions, chemical activities, and cellular/extracellular functions. Immunochemistry (immunocytochemistry in cells and immunohistochemistry (IHC) in tissues) is the technology used, either qualitatively or quantitatively (QIHC) to stain antigens (i.e., proteomes) using antibodies. Immunostaining procedures use a dye as the detection indicator. Examples of IHC applications include analyses for ER (estrogen receptor), PR progesterone receptor), p53 tumor suppressor genes, and EGRF prognostic markers. Proteomics is typically a more sensitive marker detection technology than cytogenetics because there are often orders of magnitude more protein molecules to detect using proteomics than there are cytogenetic mutations or gene-sequence alterations to detect using cytogenetics. However, proteomics may have a poorer specificity than the cytogenetic marker detection technology since multiple pathologies may result in similar changes in protein over-expression or under-expression. Immunochemistry involves histological or cytological localization of immunoreactive substances in tissue sections or cell preparations, respectively, often utilizing labeled antibodies as probe reagents. Immunochemistry can be used to measure the concentration of a disease marker (specific protein) in a sample of cells by treating the cells with an agent such as a labeled antibody (probe) that is specific for an epitope on the disease marker, then washing away unbound antibodies and measuring the signal of the label. Immunochemistry is based on the property that cancer cells possess different levels of certain disease markers than do healthy cells. The concentration of a disease marker in a cancer cell is generally large enough to produce a large signal. Therefore, tests that rely on immunochemistry will likely have a high sensitivity, yielding few false negatives. However, because other factors in addition to the disease state may cause the concentration of a disease marker to become raised or lowered, tests that rely on immunochemical analysis of a specific disease marker will likely have poor specificity, yielding a high rate of false positives.

The present invention provides a noninvasive disease state detection and discrimination method with both high sensitivity and high specificity. The method involves contacting a cytological sample suspected of containing diseased cells with a panel of probes comprising a plurality of agents, each of which quantitatively binds to a specific disease marker, and detecting and analyzing the pattern of binding of the probe agents. The present invention also provides methods of constructing and validating a panel of probes for detecting a specific disease (or group of diseases) and discriminating among its various disease states. Illustrative panels for detecting lung cancer and discriminating among different types of lung cancer are also provided.

A human disease results from the failure of the human organism's adaptive mechanisms to neutralize external or internal insults which result in abnormal structures or functions within the body's cells, tissues, organs or systems. Diseases can be grouped by shared mechanisms of causation as illustrated below, in Table 1.

TABLE 1

| Classes of Diseases | Examples of Disease States |
|---|---|
| Allergy | Adverse reactions to foods and plants |
| Cardiovascular | Heart failure, atherosclerosis |
| Degenerative (neurological and muscular) | Alzheimer's and Parkinson's |
| Diet | Non-nutritional substances and excess/imbalanced nutrition |
| Hereditary | Sickle cell anemia, cystic fibrosis |
| Immune | HIV and autoimmune |
| Infection | Viral, bacterial, fungal, parasitic |
| Metabolic | Diabetes |
| Molecular and cell biology | Cancer (neoplasia) |
| Toxic insults | Alcohol, drugs, environmental mutagens and carcinogens |
| Trauma | Bodily injury from automobile collision |

Disease states are either caused by or result in abnormal changes (i.e., pathological conditions) at a subcellular, cellular, tissue, organ, or human anatomic or physiological system level. Many disease states (e.g., lung cancer) are characterized by abnormal changes at a subcellular or cellular level. Specimens (e.g., cervical PAP smears, voided urine, blood, sputum, colonic washings) can be collected from patients with suspected disease states to diagnose those patients for the presence and type of the disease state. Molecular pathology is the discipline that attempts to identify and diagnostically exploit the molecular changes associated with these cell-based diseases.

Lung cancer is an illustrative example of a disease state in which screening of high-risk populations and at-risk individuals can be performed using diagnostic tests (e.g., molecular diagnostic panel assays) to detect the presence of the disease state. Also, for patients in which lung cancer or other disease states have been detected by these means, related diagnostic tests can be employed to differentiate the specific disease state from related or co-occurring disease states. For example, in this lung cancer illustration, additional molecular diagnostic panel assays may indicate the probabilities that the patient's disease state is consistent with one of the following types of lung cancer: (a) squamous cell carcinoma of the lung, (b) adenocarcinoma of the lung, (c) large cell carcinoma of the lung, (d) small cell carcinoma of the lung, or (e) mesothelioma. Early detection and differentiation of cell-based disease states is a hypothesized means to improve patient outcomes.

Cancer is a neoplastic disease the natural course of which is fatal. Cancer cells, unlike benign tumor cells, exhibit the properties of invasion and metastasis and are highly anaplastic. Cancer includes the two broad categories of carcinoma and sarcoma, but in normal usage it is often used synonymously with carcinoma. According to the World Health Organization (WHO), cancer affects more than 10 million people each year and is responsible for in excess of 6.2 million deaths.

Cancer is, in reality, a heterogeneous collection of diseases that can occur in virtually any part of the body. As a result, different treatments are not equally effective in all cancers or even among the stages of a specific type of cancer. Advances in diagnostics (e.g., mammography, cervical cytology, and serum PSA testing) have, in some cases, allowed for the detection of early-stage cancer when there are a greater number of treatment options, and therapies tend to be more effective. In cases where a solid tumor is small and localized, surgery alone may be sufficient to produce a cure. However, in cases where the tumor has spread, surgery may provide, at best, only limited benefits. In such cases the addition of chemotherapy and/or radiation therapy may be used to treat metastatic disease. While somewhat effective in prolonging life, treatment of patients with metastatic disease rarely produces a cure. Even through there may be an initial response, with time the disease progresses and the patient ultimately dies from its effects and/or from the toxic effects of the treatments.

While not proven, it is generally accepted that early detection and treatment will reduce the morbidity, mortality and cost of cancer. Early detection will, in many cases, permit treatment to be initiated prior to metastasis. Furthermore, because there are a greater number of treatment options, there is a higher probability of achieving a cure or significant improvement in long-term survival.

Developing a test that can be used to screen an "at-risk" population has long been a goal of health practitioners. While there have been some successes such as mammography for breast cancer, PSA testing for prostate cancer, and the PAP smear for cervical cancer, in most cases cancer is detected at a relatively late stage where the patient is symptomatic and the disease is almost always fatal. For most cancers, no test or combination of tests has exhibited the necessary sensitivity and specificity to permit cost-effective identification of patients with early stage disease.

For a cancer screening program to be successful and gain acceptance by patients, physicians, and third party payers, the test must have implied benefit (changes the outcome), be widely available and be able to be carried out readily within the framework of general healthcare. The test should be relatively noninvasive, leading to adequate compliance, have high sensitivity, and reasonable specificity and predictive value. In addition, the test must be available at relatively low cost.

For patients who are suspected of having cancer, the diagnosis must be confirmed and the tumor properly staged cytologically and clinically in order for physicians to undertake appropriate therapeutic intervention. Some tests currently being used in the diagnosis and staging of cancer, however, either lack sufficient sensitivity or specificity, are too invasive, or are too costly to justify their use as a population-based screening test. Shown below in Tables 2 and 3, for example, are estimates of sensitivity and specificity of lung cancer diagnostics and estimated costs for diagnostic tests used to detect lung cancer.

TABLE 2

ESTIMATES OF SENSITIVITY AND SPECIFICITY OF LUNG CANCER DIAGNOSTICS [1]

| DIAGNOSTIC TEST | SENSITIVITY (%) | SPECIFICITY (%) |
|---|---|---|
| Conventional Sputum Cytology | 51.0 | 100.0 |
| Chest X-ray | 16–85* | 90–95 |
| White Light Bronchoscopy | 48.0–80.0 | 91.1–96.8 |

TABLE 2-continued

ESTIMATES OF SENSITIVITY AND SPECIFICITY OF
LUNG CANCER DIAGNOSTICS [1]

| DIAGNOSTIC TEST | SENSITIVITY (%) | SPECIFICITY (%) |
|---|---|---|
| LIFE Bronchoscopy | 72.0 | 86.7 |
| Computed Tomography | 63.0–99.9 | 80.0–61 |
| PET Scan | 88.0–92.5 | 83.0–93.0 |

*Dependent upon the stage of the disease at the time of diagnosis

TABLE 3

ESTIMATED COSTS FOR DIAGNOSTIC TESTS
USED IN LUNG CANCER [1]

| DIAGNOSTIC TEST | COST ($) |
|---|---|
| Sputum Cytology | 90 |
| Chest X-ray | 44 |
| Bronchoscopy | 725 |
| Computed Tomography | 378 |
| PET Scan | 800–3000 |
| Open Biopsy | 12,847–14,121 |

The chest radiograph (X-ray) is often used to detect and localize cancer lesions due to its reasonable sensitivity, high specificity and low cost. However, small lesions are often difficult to detect and although larger tumors are relatively easy to visualize on a chest film, at the time of detection most have already metastasized. Thus, chest X-rays lack the necessary sensitivity for use as an early detection method.

Computed tomography (CT) is useful in the confirmation and characterization of pulmonary nodules and allows the detection of subtle abnormalities that are often missed on a standard chest X-ray [2]. CT, and Spiral CT methods in particular, remains the test of choice for patients who present with a prior malignant sputum cytology result or vocal chord paralysis. CT, with its improved sensitivity over the conventional chest film, has become the primary tool for imaging the central airway [3]. While capable of examining large areas, CT is subject to artifacts from cardiac and respiratory motion although improved resolution can be achieved through the use of iodinated contrast material.

Spiral CT is a more rapid and sensitive form of CT that has the potential to detect early cancer lesions more reliably than either conventional CT or X-ray. Spiral CT appears to have greatly improved sensitivity in diagnosing early disease. However, the test has relatively low specificity with a 20% false positive rate [4]. Spiral CT is also less sensitive in detecting the central lesions that represent one-third of all lung cancers. Furthermore, while the cost of the initial test is relatively low ($300), the cost of follow-up can be high. Cytology using molecular diagnostic panel assays offers significant promise as an adjunctive test with Spiral CT to improve the specificity of Spiral CT testing by minimizing false positive results through the evaluation of fine needle aspirations (FNAs) or biopsies (FNBs) from Spiral CT-suspicious pulmonary nodules.

Fluorescence bronchoscopy provides increased sensitivity over conventional white light bronchoscopy, significantly improving the detection of small lesions within the central airway [5]. However, fluorescence bronchoscopy is unable to detect peripheral lesions, it takes a long time for bronchoscopists to examine a patient's airways, and it is an expensive procedure. Additionally, the procedure is moderately invasive, creating an insurmountable barrier to its use as a population-based screening test.

Positron Emission Tomography (PET) is a highly sensitive test that utilizes radioactive glucose to identify the presence of cancer cells within the lung [6–8]. The cost of establishing a testing facility is high and there is the need for a cyclotron on site or nearby. This, coupled with the high cost of the test, has limited the use of PET scans to staging lung cancer patients rather than for early detection of the disease.

Although used for some time as a means of screening for lung cancer, sputum cytology has enjoyed only limited success due to its low sensitivity and its failure to reduce disease-specific mortality. In conventional sputum cytology, the pathologist uses characteristic changes in cellular morphology to identify malignant cells and make a diagnosis of cancer. Today only 15% of patients who are "at-risk" or who are suspected of having lung cancer undergo sputum cytology testing, and less than 5% undergo multiple evaluations [9]. A number of factors including tumor size, location, degree of differentiation, cell clumping, inefficiency of clearing mechanisms to release cells and sputum to the external environment, and the poor stability of cells within the sputum contribute to the overall poor performance of the test.

Cancer diagnostics has traditionally relied upon the detection of single molecular markers. Unfortunately, cancer is a disease state in which single markers have typically failed to detect or differentiate many forms of the disease. Thus, probes that recognize only a single marker have been shown to be largely ineffective. Exhaustive searches for "magic bullet" diagnostic tests have been underway for many decades though no universal successful magic bullet probes have been found to date.

A major premise of this invention is that cell-based cancer diagnostics and the screening, diagnosis for, and therapeutic monitoring of other disease states will be significantly improved over the state-of-the-art that uses single marker/probe analyses rather than kits of multiple, simultaneously labeled probes. This multiplexed analytical approach is particularly well suited for cancer diagnostics since cancer is not a single disease. Furthermore, this multi-factorial "panel" approach is consistent with the heterogeneous nature of cancer, both cytologically and clinically.

Key to the successful implementation of a panel approach to cell-based diagnostic tests is the design and development of optimized panels of probes that can chemically recognize the pattern of markers that characterizes and distinguishes a variety of disease states. This patent application describes an efficient and unique methodology to design and develop such novel and optimized panels.

Improved methods for specimen collection (e.g., point-of-care mixers for sputum cytology) and preparation (e.g., new cytology preservation and transportation fluids, and liquid-based cytology preparation instruments) are under development and becoming commercially available. In conjunction with existing and these emerging methods, a successful implementation of this molecular diagnostics cell-based panel assay will lead to (a) characterization of the molecular profile of malignant tumors and other disease states, (b) improved methods for early cancer and other disease state detection and differentiation, and (c) opportunities for improved clinical diagnoses, prognoses, customized patient treatments, and therapeutic monitoring.

SUMMARY OF THE INVENTION

The present invention is directed to a panel for detecting a generic disease state or discriminating between specific disease states using cell-based diagnosis. The panel comprises a plurality of probes each of which specifically binds to a marker associated with a generic or specific disease state, wherein the pattern of binding of the component probes of the panel to cells in a cytology specimen is diagnostic of the presence or specific nature of said disease state. The present invention is also directed to a method of forming a panel for detecting a disease state or discriminating between disease states in a patient using cell-based diagnosis. The method involves determining the sensitivity and specificity of binding of probes each of which specifically binds to a member of a library of markers associated with a disease state and selecting a limited plurality of said probes whose pattern of binding is diagnostic for the presence or specific nature of said disease state. The present method is also directed to a method of detecting a disease or discriminating between disease states comprising. The method involves contacting a cytological sample suspected of containing abnormal cells characteristic of a disease state with a panel according to claim 1 and detecting a pattern of binding of said probes that is diagnostic for the presence or specific nature of said disease state.

BRIEF DESCRIPTION OF THE FIGURES

FIG. 1. Molecular markers that are preferable markers to be included in a panel for identifying different histologic types of lung cancer. The column labeled "%" indicates the percentage of tumor specimens that express a particular marker.

FIG. 2. Potential ways in which different markers may be used to discriminate between specific types of lung cancer. SQ indicates squamous cell carcinoma, AD indicates adenocarcinoma, LC indicates large cell carcinoma, SC indicates small cell carcinoma and ME indicates mesothelioma. The numbers appearing in each cell represent frequency of marker change in one cell type versus another. To be included in the table, the ratio must be greater than 2.0 or less than 0.5. A number larger than 100 generally indicates that the second marker is not expressed. In such cases the denominator was set at 0.1 for the purpose of the analysis. Finally, empty cells represent either no difference in expression or the absence of expression data.

FIG. 4. Correlation matrix, in which correlation measures the amount of linear association between a pair of variables. All markers in this matrix with a correlation number of 50% or higher are considered correlate markers.

FIG. 5. Detection panel compositions, pair-wise discrimination panel compositions and joint discrimination panel compositions. Panel compositions using decision tree analysis, stepwise LR and stepwise LD are shown.

FIG. 6. Detection panel compositions wherein probe 7 was not included as a probe. Panel compositions using decision tree analysis, stepwise LR and stepwise LD are shown.

FIG. 7. Detection panel compositions using only commercially preferred probes. Panel compositions using decision tree analysis, stepwise LR and stepwise LD are shown.

DETAILED DESCRIPTION OF THE INVENTION

1. Introduction

Figure 3:
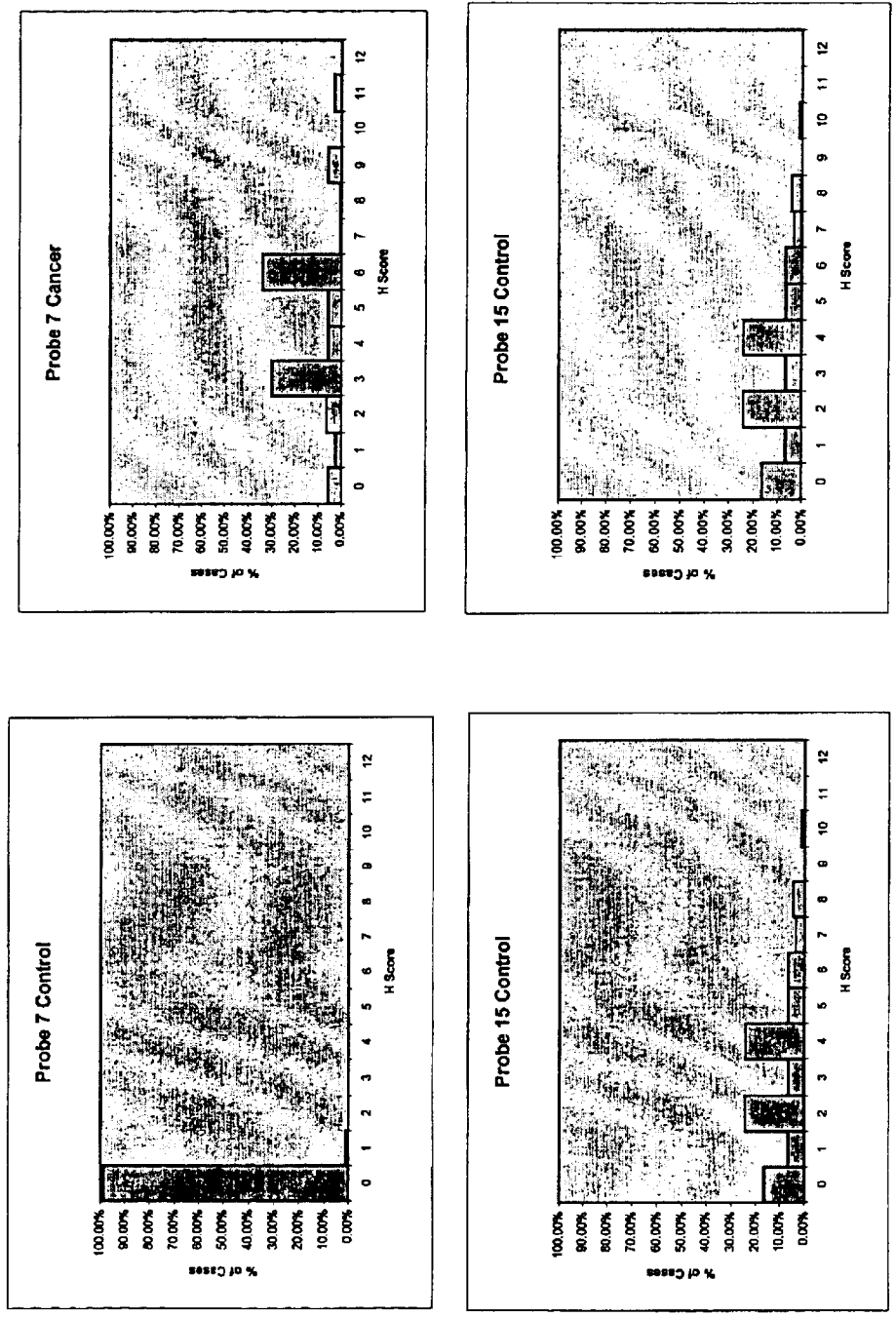
FIG. 3. Comparisons between H-scores for probes 7 and 15 in control tissue and in cancerous tissue. The x-axis shows the H-scores while the y-axis shows the percent of cases.

The present invention provides a noninvasive disease state detection and discrimination method with high sensitivity and specificity. The method involves contacting a cytological sample suspected of containing diseased cells with a panel comprising a plurality of agents, each of which quantitatively binds to a disease marker, and detecting a pattern of binding of the agents. This pattern includes the localization and density/concentration of binding of the component probes of the panel. The present invention also provides methods of making a panel for detecting a disease and also for discriminating between disease states as well as panels for detecting lung cancer in early stages and discriminating between different types of lung cancer. Panel tests have been used in medicine. For example, panels are used in blood serum analysis. However, because a cytology analysis involves imaging and localization of specific markers within individual cells and tissues, prior to the present invention it was not apparent that the panel approach would be effective for cytology samples. Additionally, it was not apparent which, if any statistical analyses could be applied to design and develop an optimized cell-based diagnostic panel of probes.

One of the few examples of a cytology-based screening program is the PAP Smear, which screens for cervical cancer. For over 50 years this method has been practiced and has greatly contributed to the fact that today, almost no woman who has regular PAP smears dies of cervical cancer. There are drawbacks, however, to the PAP smear screening program. For example, PAP smears are labor intensive and are not universally accessible. The present molecular diagnostic cell-based screening method utilizing probe panels does not suffer from these drawbacks. The method may be fully automated and thereby made less expensive, increasing access to this type of testing.

The present invention provides a method, having both high specificity and high sensitivity, for detecting a disease state and for discriminating between disease states. The invention is applicable to any cell-based disease state, such as cancer and infectious diseases.

The panel is diagnostic of the presence or specific nature of the disease state. The present invention overcomes the limitations and drawbacks of known disease state detection methods by enabling quick, accurate, relatively noninvasive and easy detection and discrimination of diseased cells in a cytological sample while keeping costs low.

A feature of the inventive method for making a panel of the present invention is the rapidity with which the panel may be developed.

There are several benefits to using a panel of agents in a method for detecting a disease state, and for discriminating between types of disease states. One benefit is that a panel of agents has sufficient redundancy to permit detection and characterization of disease states thereby increasing the sensitivity and specificity of the test. Given the heterogeneous nature of many disease states, no single agent is capable of identifying the vast majority of cases.

An additional benefit to using a panel is that use of a panel permits discrimination between the various types of a disease state based on specific patterns (probe localization and density/concentration) of expression. As the various types of a disease may exhibit dramatic differences in their rate of progression, response to therapy, and lethality, knowledge of the specific type can help physicians choose the optimal therapeutic approach.

2. The Panel

The panel of the present invention comprises a plurality of agents, each of which quantitatively binds to a disease marker, wherein the pattern (localization and density/concentration) of binding of the component agents of the panel is diagnostic of the presence or specific nature of a disease state. Therefore, the panel may be a detection panel or a discrimination panel. A detection panel detects whether a generic disease state is present in a sample of cells, while a discrimination panel discriminates among different specific disease states in a sample of cells known to be affected by a disease state which comprises different types of diseases. The difference between a detection panel and a discrimination panel lies in the specific agents that the panels comprise. A detection panel comprises agents having a pattern of binding that is diagnostic of the presence of a disease state, while a discrimination panel comprises agents having a pattern of binding that allows for determining the specific nature (i.e., each type) of the disease state.

A panel, by definition, contains more than one member. There are several reasons why it is beneficial to use a panel of markers rather than just one marker alone to detect a generic disease state or to discriminate among specific disease states. One reason is the unlikely existence of a probe for one single marker, that is present in all diseased cells yet not present in healthy cells, whose behavior can be measured with a high specificity and sensitivity to yeild an accurate test result. If such a single probe existed for detection of a particular disease with high sensitivity and specificity, it would already have been utilized for clinical testing. Rather, it is the directed selection of panel tests, each consisting of multiple probes, that together can provide the range of detection capability to ensure clinically adequate testing.

If one nevertheless chooses to construct a panel test comprising one or a very few probes, then the failure of any single marker/probe combination to perform its labeling function for any reason (for example, diminished reactivity of the specimen cells due to biological variability; inherent variability between lots of probe reagents; a weak, outdated or defective processing reagent; improper processing time or conditions for that probe) could result in a catastrophic failure of the test to detect or discriminate the target disease. The inclusion of multiple, and even redundant probes in each panel test greatly enhances the probability that a failure of any one probe will not cause a catastrophic failure of the test.

A probe is any molecular structure or substructure that binds to a disease marker. The term "agent" as used herein, may also refer to a molecular structure or substructure that binds to a disease marker. Molecular probes are homing devices used by biologists and clinicians to detect and locate markers indicative of the specific disease states. For example, antibodies may be produced that bind specifically to a protein previously identified as a marker for small cell lung cancer. This antibody probe can then be used to localize the target protein marker in cells and tissues of patients suspected of having the disease by using appropriate immunochemical protocols and incubations. If the antibody probe binds to its target marker in a stoichiometric (i.e., quantitative) fashion and is labeled with a chromogenic or colored "tag", then localization and quantitation of the probe and, indirectly, its target marker may be accomplished using an optical microscope and image cytometry technology.

The present invention contemplates detecting changes in molecular marker expression at the DNA, RNA or protein level using any of a number of methods available to an ordinary skilled artisan. Exemplary probes may be a polyclonal or monoclonal antibody or fragment thereof or a nucleic acid sequences that is complementary to the nucleic acid sequence encoding a molecular marker in the panel. A probe may also be a stain, such as a DNA stain. Many of the antibodies used in the present invention are specific to a variety of cell surface or intracellular antigens as marker substances. The antibodies may be synthesized using techniques generally known to those of skill in the art. For example, after the initial raising of antibodies to the marker, the antibodies can be sequenced and subsequently prepared by recombinant techniques. Alternatively, antibodies may be purchased.

In embodiments of the present invention, the probe contains a label. A probe containing a label is often referred to herein as a "labeled probe". The label may be any substance that can be attached to a probe so that when the probe binds to the marker a signal is emitted or the labeled probe can be detected by a human observer or an analytical instrument. This label may also be referred to as a "tag". The label may be visualized using reader instrumentation. The term "reader instrumentation" refers to the analytical equipment used to detect a probe. Labels envisioned by the present invention are any labels that emit a signal and allow for identification of a component in a sample. Preferred labels include radioactive, fluorogenic, chromogenic or enzymatic moieties. Therefore, possible methods of detection include, but are not limited to, immunocytochemistry, immunohistochemistry, in situ hybridization, fluorescent in situ hybridization, flow cytometry and image cytometry. The signal generated by the labeled probe is of sufficient intensity to permit detection by a medical practitioner.

A "marker", "disease marker" or "molecular marker" is any molecular structure or substructure that is correlated with a disease state or pathogen. The term "antigen" may be used interchangeably with "marker". Broadly defined, a marker is a biological indicator that may be deliberately used by an observer or instrument to reveal, detect, or measure the presence or frequency and/or amount of a specific condition, event or substance. For example, a specific and unique sequence of nucleotide bases may be used as a genetic marker to track patterns of genetic inheritance among individuals and through families. Similarly, molecular markers are specific molecules, such as proteins or protein fragments, whose presence within a cell or tissue indicates a particular disease state. For example, proliferating cancer cells may express novel cell-surface proteins not found on normal cells of the same type, or may over-express specific secretory proteins whose increased or decreased abundance (e.g., overexpression or underexpression, respectively) can serve as markers for a particular disease state.

Suitable markers for cytology panels are substances that are localized in or on the nucleus, cytoplasm or cell membrane. Markers may also be localized in organelles located in any of these locations in the cell. Exemplary markers localized in the nucleus include but are not limited to retinoblastoma gene product (Rb), Cyclin A, nucleoside diphosphate kinase/nm23, telomerase, Ki-67, Cyclin D1, proliferating cell nuclear antigen (PCNA), p120 (proliferation-associated nucleolar antigen) and thyroid transcription factor 1 (TTF-1). Exemplary markers localized in the cytoplasm include but are not limited to VEGF, surfactant apoprotein A (SP-A), nucleoside nm23, melanoma antigen-1 (MAGE-1), Mucin 1, surfactant apoprotein B (SP-B), ER related protein p29 and melanoma antigen-3 (MAGE-3). Exemplary markers localized in the cell membrane include but are not limited to VEGF, thrombomodulin, CD44v6, E-Cadherin, Mucin 1, human epithelial related antigen (HERA), fibroblast growth factor (FGF), heptocyte growth factor receptor (C-MET), BCL-2, N-Cadherin, epidermal growth factor receptor (EGFR) and glucose transporter-3 (GLUT-3). An example of a marker located in an organelle of the cytoplasm is BCL-2, located (in part) in the mitochondrial membrane. An example of a marker located in an organelle of the nucleus is p120 (proliferating-associated nucleolar antigen), located in the nucleoli.

Preferred are markers where changes in expression: occur early in disease progression, are exhibited by a majority of diseased cells, allow for detection of in excess of 75% of a given disease type, most preferably in excess of 90% of a given disease type and/or allow for the discrimination between the nature of different types of a disease state.

It is noted that the inventive panel may be referred to as a panel of probes or a panel of markers, since the probes bind to the markers. Therefore, the panel may comprise a number of markers or it may comprise a number of probes that bind to specific markers. For the sake of consistency, the present panel is referred to as a panel of probes; however, it could also be referred to as a panel of markers.

Markers can also include features such as malignancy-associated changes (MACs) in the cell nucleus or features related to the patient's family history of cancer. Malignancy-associated changes, or MACs, are typically sub-visual changes that occur in normal-appearing cells located in the vicinity of cancer cells. These exceedingly subtle changes in the cell nucleus may result biologically from changes in the nuclear matrix and the chromatin distribution pattern. They cannot be appreciated even by trained observers through the visual observation of individual cells, but may be determined from statistical analysis of cell populations using highly automated, computerized high-speed image cytometry. Techniques for detection of MACs are well known to those of skill in the art and are described in more detail in: Gruner, O. C. *Brit J. Surg.* 3 506–522 (1916); Neiburgs, H. E. et al., *Transaction, 7th Annual Mtg. Inter. Soc. Cytol. Council* 137–144 (1959); Klawe, H. *Acta. Cytol.* 18 30–33 (1974); Wied, G. L., et al., *Analty. Quant. Cytol.* 2 257–263 (1980); and Burger, G., et al., *Analyt. Quant. Cytol.* 3 261–271 (1981).

The present invention encompasses any marker that is correlated with a disease state. The individual markers themselves are mere tools of the present invention. Therefore, the invention is not limited to specific markers. One way to classify markers is by their functional relationship to other molecules. As used herein, a "functionally related" marker is a component of the same biological process or pathway as the marker in question and would be known by a person of skill in the art to be abnormally expressed together with the marker in question. For example, many markers are associated with a cell proliferation pathway, such as fibrobast growth factor (FGF), (vascular endothelial growth factor) VEGF, CyclinA and Cyclin D1. Other markers are glucose transporters, such as Glut-1 and Glut-3.

A person of ordinary skill in the art is well equipped to determine a functionally related marker and may research various markers or perform experiments in which the functional behavior of a marker is determined. By way of non-limiting example, a marker may be classified as a molecule involved in angiogenesis, a transmembrane glycoprotein, a cell surface glycoprotein, a pulmonary surfactant protein, a nuclear DNA-binding phosphoprotein, a transmembrane $Ca^{2+}$ dependent cell adhesion molecule, a regulatory subunit of the cyclin-dependent kinases (CDK's), a nucleoside diphosphate kinase, a ribonucleoprotein enzyme, a nuclear protein that is expressed in proliferating normal and neoplastic cells, a cofactor for DNA polymerase delta, a gene that is silent in normal tissues yet when it is expressed in malignant neoplasms is recognized by autologous, tumor-directed and specific cytotoxic T cells (CTL's), a glycosylated secretory protein, the gastrointestinal tract or genitourinary tract, a hydrophobic protein of a pulmonary surfactant, a transmembrane glycoprotein, a molecule involved in proliferation, differentiation and angiogenesis, a proto-oncogene, a homeodomain transcription factor, a mitochondrial membrane protein, a molecule found in nucleoli of a rapidly proliferating cell, a glucose transporter, or an estrogen-related heat shock protein.

Classes of biomarkers and probes include, but are not limited to: (a) morphologic biomarkers, including DNA ploidy, MACs and premalignant lesions; (b) genetic biomarkers including DNA adducts, DNA mutations and apoptotic indices; (c) cell cycle biomarkers including cellular proliferation, differentiation, regulatory molecules and apoptosis markers, and; (d) molecular and biochemical biomarkers including oncogenes, tumor suppressor genes, tumor antigens, growth factors and receptors, enzymes, proteins, prostaglandin levels and adhesion molecules.

A "disease state" may be any cell-based disease. In some embodiments the disease state is cancer. In other embodiments, the disease state is an infectious disease. The cancer may be any cancer, including, but not limited to epithelial cell-based cancers from the pulmonary, urinary, gastrointestinal, and genital tracts; solid and/or secretory tumor-based cancers, such as sarcomas, breast cancer, cancer of the pancreas, cancer of the liver, cancer of the kidneys, cancer of the thyroid, and cancer of the prostate; and blood-based cancers, such as leukemias and lymphomas. Exemplary cancers which may be detected by the present invention are lung, bladder, gastrointestinal, cervical, breast or prostate cancer. Exemplary infectious diseases which may be detected are cell-based sieases in which the infectious organism is a virus, bacteria, protozoan, parasite, or fungus. The infectious disease, for example, may be HIV, hepatitis, influenza, meningitis, mononucleosis, tuberculosis and sexually transmitted diseases (STDs), such as chlamydia, trichomonas, gonorrhea, herpes and syphilis.

As used herein, the term "generic disease state" refers to a disease which comprises several types of specific diseases, such as lung cancer, sexually transmitted diseases and immune-based diseases. Specific disease states are also referred to as histologic types of diseases. For example, the term "lung cancer" comprises several specific diseases, among which are squamous cell carcinoma, adenocarcinoma, large cell carcinoma, small cell lung cancer and mesothelioma. The term "sexually transmitted diseases" comprises several specific diseases, among which are Gonorrhea, Human Papilloma Virus (HPV), herpes and Syphilis. The term "immune-based diseases" comprises several specific diseases, such as systemic lupus erythematosus (Lupus), rheumatoid arthritis and pernicious anemia.

As used herein, the term "high-risk population" refers to a group of individuals who are exposed to disease causing agents, e.g., carcinogens, either at home or in the workplace (i.e., a "high risk population" for lung cancer might be exposed to smoking, passive smoking and occupational exposure). Individuals in a "high-risk population" may also have a genetic predisposition.

The term "at-risk" refers to individuals who are asymptotic but, because of a family history or significant exposure are at a significant risk of developing a disease state (i.e., an individual at risk for lung cancer with a >30 pack-year history of smoking; "pack-year" is a measurement unit computed by multiplying the number of packs smoked per day, times the number of years for this exposure).

Cancer is a disease in which cells divide without control due to, for example, altered gene expression. In the methods and panels of the present invention, the cancer may be any malignant growth in any organ. For example, the cancer may be lung, bladder, gastrointestinal, cervical, breast or prostate cancer. Each cancer may comprise a collection of diseases or histological types of cancer. The term "histologic type" refers to cancers of different histology. Depending on the cancer there can be one or several histologic types. For example, lung cancer includes, but is not limited to, squamous cell carcinoma, adenocarcinoma, large cell carcinoma, small cell carcinoma and mesothelioma. Knowledge of the histologic type of cancer affecting a patient is very useful because it helps the medical practitioner to localize and characterize the disease and to determine the optimal treatment strategy.

Infectious diseases include cell-based diseases in which the infectious organism is a virus, bacteria, protozoan, parasite or fungus.

Exemplary detection and discrimination panels are panels that detect lung cancer, a general disease state, and panels that discriminate a single lung cancer type, specific disease state, against all other types of lung cancer and false positives. False positives can include metastatic cancer of a different type, such as metastasized liver, kidney or pancreatic cancer.

3. Methods of Making a Panel

The method of making a panel for detecting a generic disease state or discriminating between specific disease states in a patient involves determining the sensitivity and specificity of binding of probes to a library of markers associated with a generic or specific disease state and selecting a plurality of said probes whose pattern of binding (localization and density/concentration) is diagnostic of the presence or specific nature of the disease state. In some embodiments, optional preliminary pruning and preparation steps are performed. The method of making a panel of the present invention involves analyzing the pattern of binding of probes to markers in known histologic pathology samples, i.e. gold standards. The classifier designed on the gold standard data can then be used to design a classifier for cytometry, especially automated cytometry. Therefore, the set of marker probes selected from the pathology analysis is used to prepare a new training data set taken from a cytology sample, such as sputum, fine needle aspirations, urine, etc. Cells shed from the specified lesions will stain in a similar fashion to the gold standards. The method described here eliminates the experimental error in selecting the best features set because the integrity of the diagnosis based on gold standard histologic pathology samples is high. Although it is, in principle, possible to use cytology samples to produce a panel, this is less desireable because cytology samples contain debris, there may be deterioration of the cells in a cytology sample, and the pathology diagnosis may be difficult to confirm clinically.

A library of markers is a group of markers. The library can comprise any number of markers. However, in some embodiments the number of markers in the library is limited by technical and/or commercial practicalities, such as specimen size. For example, in some embodiments, each specimen is tested against all of the markers in the panel. Therefore, the number of markers must not be larger than the number of samples into which the specimen may be divided. Another technical practicality is time. Typically, the library contains less than 60 markers. Preferably, the library contains less than 50 markers. More preferably, the library contains less than 40 markers. Most preferably the library contains 10–30 markers. It is preferable that the library of potential panel members contain more than 10 markers so that there is opportunity to optimize the performance of the panel. As used herein, the term "about" means plus or minus 3 markers.

In some embodiments, a library is obtained by consulting sources which contain information about various markers and correlations between the markers and generic/specific disease states. Exemplary sources include experimental results, theoretical or predicted analyses and literary sources, such as journals, books, catalogues and web sites. These various sources may use histology or cytology and may rely on cytogenetics, such as in situ hybridization; proteomics, such as immunohistochemistry; cytometry, such as MACs or DNA ploidy; and/or cytopathology, such as morphology. The markers may be localized anywhere in or on a cell. For example, the markers may be localized in or on the nucleus, the cytoplasm or the cell membrane. The marker may also be localized in an organelle within any of the aforementioned localizations.

In some embodiments, the library may be of an unsuitable size. Therefore, one or more pruning steps may be required prior to initiating the basic method for making a panel. The pruning step may involve one or several successive pruning steps. One pruning step may involve, for example, setting an arbitrary threshold for sensitivity and/or specificity. Therefore, any marker whose experimental or predicted sensitivity and/or specificity falls below the threshold may be removed from the library. Other exemplary pruning steps, which may be performed alone or in sequence with other pruning steps, may rely on detection technology requirements, access constraints and irreproducibility of reported results. With respect to detection technology requirements, it is possible that the machinery required to detect a particular marker is unavailable. With respect to access constraints, it is possible that licensing restrictions make it difficult or impossible to obtain a probe that binds to a particular marker. In some embodiments, a due diligence study is performed on each marker.

In some embodiments, prior to beginning the basic method for making a panel, it may be necessary to perform preparation steps. Exemplary preparation steps include optimizing the protocols for objective quantitative detection of the markers in the library and collecting histology specimens. Optimization of the protocols for objective quantitative detection of the markers is within the skill of an ordinary artisan. For example, the necessary reagents and supplies must be obtained, such as buffers, reagents, software and equipment. It is possible that the concentration of reagents may need to be adjusted. For example, if non-specific binding is observed, a person of ordinary skill in the art may dilute the concentration of the probe solution.

In some embodiments, the histology specimens are Gold Standards. The term "Gold Standard" is known by a person of ordinary skill in the art to mean that the histology and clinical diagnosis of the specimen is known. The gold standards are often referred to as a "training" data set. The gold standards comprise a set of measurements, or reliable estimates, of all the features that may contribute to the discriminating process. Such features are collected from samples collected from a representative number of patients with known disease states. The standard samples can be cytology samples but this is less desireable for panel selection.

The histology samples may be obtained by any technique known to those of skill in the art, for example biopsy. In some embodiments, it is necessary that the size of the specimen per patient be large enough so that enough tissue sections can be obtained to test each marker in the library.

In some embodiments, specimens are obtained from multiple patients diagnosed with each specific disease state. One specimen per patient may be obtained, or multiple specimens per patient may be obtained. In embodiments in which multiple specimens are obtained from individual patients, the expertise of the surgeon is relied upon to establish that each specimen obtained from a single patient is similar to the other specimens obtained from that patient. Specimens are also obtained from a control group of patients. The control group of patients may be healthy patients or patients that are not suffering from the generic or specific disease state that is being tested.

The first step of the basic method is determining the sensitivity and specificity of binding of probes to a library of markers associated with the desired disease state. In this step, a probe that is specific for each marker in the library is applied to a sample of the patients' specimens. Therefore, in some embodiments, if there are, for example, 30 markers in the library, each patient's specimen will be divided into 30 samples and each sample will be treated with a probe that is specific for one of the 30 markers. The probe contains a label that may be visualized. Therefore, the pattern and level of binding of the probe to the marker can be detected. The pattern and level of binding may be detected either quantitatively, i.e., by an analytical instrument, or qualitatively, by a human, such as a pathologist.

In some embodiments, an objective and/or quantitative scoring method is developed to detect the pattern and level of binding of the probe to the markers. The scoring method may be heuristically designed. Scoring methods are used to objectify a subjective interpretation, for example, by a pathologist. It is within the skill of an ordinary artisan to determine a suitable scoring method. In some embodiments, the scoring method may comprise categorizing features, such as the density of a marker probe stain as: none, weak, moderate, or intense. In another embodiment, these features may be measured with algorithms operating on microscope slide images. An exemplary scoring method is one in which the proportions and density are consolidated into a single "H Score" obtained by grading the intensity as: none=0, weak=1, moderate=2, intense=3, and the percentage cells as: 0–5%=0, 6–25%=1, 26–50%=2, 51–75%=3, >75%=4, and then multiplying the two grades together. For example, 50% weakly stained plus 50% moderately stained would score 6=(1×2)+(2×2). The "H score" honors the late Kenneth Hirsch, one of the present inventors.

An ordinary artisan is capable of addressing issues related to minimizing potential biases related to pathologists and samples. For example, randomizing may be used to minimize the chance of having a systematic error. Blinding may be used to eliminate experimental biases by the people conducting the experiments. For example, in some embodiments, pathologist-to-pathologist variation may be minimized by conducting a double blind study. As used herein, the term "double blind study" is a well establish method for avoiding biases, where the data collection and data analysis are done independently. In other embodiments, sample-to-sample variation is minimized by randomizing the samples. For example, the samples are randomized before the pathologist analyzes them. There is also randomization involved in the experimental protocols. In some embodiments, each sample is analyzed by at least two pathologists. For each patient, a reliable assessment of the binding of the probe to the marker is obtained. In one embodiment, this diagnosis is made by qualified pathologists, using two pathologists per patient, to check for reliability.

A sufficient number of samples should be collected to produce reliable designs and reliable statistical performance estimates. It is within the skill of a normal artisan to determine how many samples are sufficient to produce reliable designs and reliable statistical performance estimates. Most standard classifier design packages have methods for determining the reliability of the performance estimates and the sample size should be progressively increased until reliable estimates are achieved. For example, sufficient estimates to produce reliable designs may be achieved with 200 samples collected and 27 different features estimated from each sample.

The second step is selecting a limited plurality of probes. The selecting step may employ statistical analysis and/or pattern recognition techniques. In order to perform the selecting step, the data may be consolidated into a database. In some embodiments, the probes may be numbered to render their method of action as unseen during the analysis of their effectiveness and further minimize biases. Rigorous statistical techniques are used because of the large amount of data that is generated by this method. Any statistical method may be used and an ordinary skilled statistician will be able to identify which and how many methods are appropriate.

Any number of statistical analysis and/or pattern recognition methods may be employed. Since the structure of the data is initially unknown, and since different classifier design methods perform better for different structures, it is preferred to use at least two design methods on the data. In some embodiments, three different methodologies may be used. One of ordinary skill in the art of statistical analysis and/or pattern recognition of data sets would recognize from characteristics of the data set structures that certain statistical methods would be more likely to yield an efficient result than others, where efficient in this case means achieving a certain level of sensitivity and specificity with a desired number of probes. A person of ordinary skill in the art would know that the efficiency of the statistical analysis and/or method is data dependent.

Exemplary statistical analysis and/or pattern recognition methods are described below:

a) A decision tree method, known as C4.5. C4.5 is public domain software available via the internet. This is well suited to data that can be best classified by sequentially applying a decision threshold to specific features in turn. This works best with uncorrelated data; it also copes with data with similar means provided the variances differ. The C4.5 package was used to provide the examples shown herein.

b) Linear Discriminant Analysis. This involves finding weighted combinations of the features that give the best separation of the classes. These methods work well with correlated data, but not in data with similar means and different variances. Several statistical packages were used (SPSS, SAS and R), depending on the performance estimates and graphical outputs required. Fisher's linear discriminant function was used to obtain the classifier that minimized the error rate. A canonical discriminant function was used to compute receiver operating characteristic (ROC) curves showing the trade-off between sensitivity and selectivity as the decision threshold is changed.

c) Logistic Regression. This is a non-linear transformation of the linear regression model: the dependent variable is replaced by a log odds ratio (logit). Linear regression, like discriminant analysis, belongs to a class of statistical methods founded on linear models. Such models are based on linear relationships between the explanatory variables.

With a sufficient number of samples it is possible, using the above techniques and software packages, to search for combinations of features giving good discrimination between the classes. Other exemplary statistical analysis and/or pattern recognition methods are the linear Discriminant Function Method in SPSS and Logistic Regression Method in R and SAS. SPSS is the full product name and is available from SPSS, Inc., located at SPSS, Inc. Headquarters, 233 S. Wacker Drive, 11th floor, Chicago, Ill. 60606 (www.spss.com). SAS is the full product name and is available from SAS Institute, Inc., 100 SAS Campus Drive, Cary, N.C. 27513–2414, USA (www.sas.com). R is the full product name and is available as Free Software under the terms of the Free Software Foundation's GNU (General Public License).

In some embodiments, a correlation matrix is obtained. Correlation measures the amount of linear association between a pair of variables. A correlation matrix is obtained by correlating the data obtained with one marker to data obtained with another marker. A threshold correlation number may be set, for example, 50% correlation. In this case, all markers with a correlation number of 50% or higher would be considered correlate markers.

In some embodiments of the present invention, user supplied weighting factors may be used to obtain optimized panels. Weighting may be related to any factor. For example, certain markers may be weighted higher than others due to cost, commercial considerations, misclassifications or error rates, prevalence of a generic disease state in a geographic location, prevalence of a specific disease state in a geographic location, redundancy and availability of probes. Some factors related to cost that may encourage a user to weight certain markers higher than others is the cost of the probe and commercial access issues, such as license terms and conditions. Some factors related to commercial considerations that may encourage a user to weight certain markers higher than others are Research and Development (R&D) time, R&D cost, R&D risk, i.e., the probability that the probe will work, cost of final analytical instrument, final performance and the time to market. In a detection panel, for example, some factors related to misclassifications or error rates that may encourage a user to weight some markers higher than others is that it may be desirable to minimize false negatives. In a discrimination panel, on the other hand, it may be desirable to minimize false positives. Some factors related to prevalence of a generic or specific disease state in a geographic area that may encourage a user to weight some probes higher than others are that in some geographic locations the incidence of certain generic or specific diseases are more or less prevalent. With respect to redundancies, in some instances it is desirable to have redundancies in the panel. For example, if for some reason one probe fails to be detected, due to the biological variability of the markers in the panel, a disease state will still be detected by the other markers. In some embodiments, markers that are preferred redundant markers may be weighted more heavily.

The invention is flexible in being adaptable to the availability of features where cost or supply problems may not allow the very best combination. In one embodiment, the invention can simply be applied to the available features to find an alternative combination. In another embodiment, the algorithm is used to select features that allow cost weightings to be included in the selection process to arrive at a minimum cost solution. In the examples, marker performance estimates for combinations selected from all the markers collected or for only a group of commercially preferred probes are shown. The examples also demonstrate how the C4.5 package can be used to down weight certain probes on the basis of their high cost. These probe combinations may not perform as well as the optimum combination, but the performance might be acceptable in circumstances where cost is a significant factor.

Some of the methods used allow weightings to be applied to the classes. This is available in C4.5 where the tree design can optimize the cost. Also, the Discriminant Function method gives a single parameter output which can be used to give a desired false positive or false negative probability. A plot of these parameters for different threshold settings is known as the receiver operating characteristic (ROC) curve. An ROC curve shows the estimated percentage of false positive against true positive scores for different threshold levels of a classifier.

Given the heterogeneous nature of many generic disease states, the panels may be constructed with a degree of redundancy to ensure that the tests have sufficient sensitivity, specificity, positive predictive value (Positive Predictive Value=True Positives/(True Positives+False Positives) and negative predictive value (Negative Predictive Value=True negatives/(False Negatives+True Negatives) to justify their use as a population-based screen. However, local and regional differences may dictate specific use of the tests in different segments of the global market, and so may significantly influence the criteria used to construct the final panel test for a given market. While the optimization of clinical utility is of utmost importance, local factors including affordability (cost), technical competence, laboratory and healthcare provider resources, workflow issues, manpower requirements, and availability of the probes and labels will contribute to a final, local selection of the markers used in the panel. Well known linear discriminant function analysis is used to include and assess all potential selection factors, by which each local factor is represented by a term in the equation, and each is weighted according to its locally determined significance. In this way, a panel test optimized for use in one world region may differ from a panel test optimized for use in a different region.

Once detection or discrmination panels have been designed using the above described method, the next step is to validate the panel using known cytology samples. Prior to validation, optional optimization steps may be performed. In some embodiments, the method for collecting cytology samples may be improved. This encompasses methods of obtaining the sample from the patient as well as methods for mixing the cytology sample. In other embodiments, the cytology presentation methods may be improved. For example, identifying optimal fixatives (preservation fluids) or transportation fluids.

The cytology samples used to validate the panels produced using the gold standard histology samples are cytology samples with known diagnoses. These samples may be collected using any method known by those of skill in the art. For example, sputum samples can be collected by spontaneous production, induced production and through the use of agents that enhance sputum production. The sample is contacted with each probe in the panel and the level and pattern of binding of the probes is analyzed to determine the performance of the panel. In some embodiments, it may be necessary to further optimize the panel. For example, it may be necessary to remove a probe from the panel. Or, it may be necessary to add an additional probe to the panel. Additionally, it may be necessary to replace one probe on the panel with another probe. If a new probe is added, this probe may be a correlate marker as determined from a correlation matrix. Alternatively, the probe may be a functionally similar marker. Once the panel is optimized, the panel may proceed for further testing in clinical studies.

In other embodiments, it is not necessary to optimize the panel. If the results with the cytology samples correlate with the results from the histology samples, there may not be a need to optimize the panel and the panel may proceed for further testing in clinical studies.

4. Methods of Use

Once a panel is obtained using the above described method, it may be applied to cytologic samples. To illustrate the method, cancer, especially lung cancer, will be exemplified. Similar steps and procedures will be applied for other disease states. It is to be expected that cells shed from the specified lesions will stain in a similar fashion and show in a cytologic sample, such as a fine need aspiration, sputum, urine, in a similar fashion as in the histologic pathology samples used to obtain the panel.

The basic method of the present invention typically involves two steps. First, a cytological sample suspected of containing diseased cells is contacted with a panel containing a plurality of agents, each of which quantitatively binds to a disease marker. Then, the level or pattern of binding of each agent to a disease marker is detected. The results of the detection may be used to diagnose the presence of a generic disease or to discriminate among specific disease states. An optional preliminary step is identifying an optimized panel of agents that will aid in the detection of a disease or the discrimination between disease states in a cytologic sample.

Cytology specimens may include, but are not limited to, cellular samples collected from body fluids, such as blood, urine, spinal fluids, and lymphatic systems; epithelial cell-based organ systems, such as the pulmonary tract, e.g., lung sputum, urinary tract, e.g., bladder washings, genital tract, e.g., cervical PAP smears, and gastrointestinal tract, e.g., colonic washings; and fine needle aspirations from solid tissue sites in organs and systems such as the breast, pancreas, liver, kidneys, thyroid, bone marrow, muscles, prostate, and lungs; biopsies from solid tissue sites in organs and systems such as the breast, pancreas, liver, kidneys, thyroid, bone marrow, muscles, prostate, and lungs; and histology specimens, such as tissue from surgical biopsies.

An illustrative panel of agents according to the present invention includes any number of agents that allows for accurate detection of malignant cells in a cytological sample. Molecular markers envisioned by the present invention may be any molecule that aids in the detection of malignant cells. Markers may be selected for inclusion in a panel based on several different criteria relating to changes in level or pattern of expression of the marker. Preferred are molecular markers where changes in expression: occur early in tumor progression, are exhibited by a majority of tumor cells, allow for detection of in excess of 75% of a given tumor type, most preferably in excess of 90% of a given tumor type and/or allow for the discrimination between histologic types of cancer.

The first step of the basic method is the detection of changes in the level or pattern of expression of the panel of agents in a cytological sample. This step typically involves contacting the cytologic sample with an agent, such as a labeled polyclonal or monoclonal antibody or fragment thereof or a nucleic acid probe, and observing the signal in individual cells. Detection of cells where there is a change in signal is indicative of a change in the level of expression of the molecular marker to which the label probe is directed. The changes are based on an increase or decrease in the level of expression relative to nonmalignant cells obtained from the tissue or site being examined.

An analysis of the changes in the level or pattern of expression of a panel of agents enables a skilled artisan to determine, with high sensitivity and high specificity, whether malignant cells are present in the cytologic sample. The term "sensitivity" refers to the conditional probability that a person having a disease will be correctly identified by a clinical test, (the number of true positive results divided by the number of true positive and false negative results). Therefore, if a cancer detection method has high sensitivity, the percentage of cancers detected is high e.g., 80%, preferably greater than 90%. The term "specificity" refers to the conditional probability that a person not having a disease will be correctly identified by a clinical test, (i.e., the number of true negative results divided by the number of true negative and false positive results). Therefore, if a cancer detection method has high specificity, 80%, preferably 90%, more preferably 95%, the percentage of false positives the method produces is low. A "cytologic sample" encompasses any sample collected from a patient that contains that patient's cells. Examples of cytological samples envisioned by the present invention include body fluids, epithelial cell-based organ system washings, scrapings, brushings, smears or effusions, and fine-needle aspirates and biopsies.

Use of the markers described in this invention assumes that it is possible to obtain an adequate cytologic sample routinely and that the samples can be adequately preserved for subsequent evaluation. The cytologic sample may be processed and stored in a suitable preservative. Preferably, the cytologic sample is collected in a vial containing the preservative. The preservative is any molecule or combination of molecules known to maintain cellular morphology and inhibit or block degradation of cellular proteins and nucleic acids. To ensure proper fixation, the sample may be mixed at the collection site at high speeds to disaggregate the sample and/or break up obscuring material such as mucus, thereby exposing the cells to the preservative.

Once a specimen is obtained, it is desirable to homogenize it, using an appropriate mixing device. This permits using aliquots for multiple purposes, including the possibility of sending aliquots to more than one testing site, as well as preparing multiple slides and/or multiple depositions on a slide. The initial homogenization of the specimen and of each aliquot before use will ensure that each individual slide will have substantially the same distribution of cells, so that comparisons of results from one slide to another will be meaningful.

Preparation of a specimen for analysis involves applying a sample to a microscope slide using methods including, but not limited to, smears, centrifugation, or deposition of a monolayer of cells. Such methods may be manual, semi-automated, or fully automated. The cell suspension may be aspirated depositing the cells on a filter and a monolayer of cells transferred to a prepared slide that may be processed for further evaluation. By repeating this process additional slides may be prepared as necessary. The present invention encompasses detection of one molecular marker per slide. Detection of several molecular markers per slide is also envisioned. Preferably, 1–6 markers are detected per slide. In some embodiments 2 markers are detected per slide. In other embodiments, 3 markers are detected per slide.

The present invention contemplates detecting changes in molecular marker expression at the DNA, RNA or protein level using any of a number of methods available to an ordinary skilled artisan. Detection of the changes in the level or pattern of expression of the molecular markers in a cytologic sample generally involves contacting a cytologic sample with a polyclonal or monoclonal antibody or fragment thereof or a nucleic acid sequence that is complementary to the nucleic acid sequence encoding a molecular marker in the panel, collectively "probes", and a label. Typically, the probe and label components are operatively linked so that when the probe reacts with the molecular marker a signal is emitted (a "labeled probe"). Labels envisioned by the present invention are any labels that emit or enable a signal and allow for identification of a component in a sample. Preferred labels include radioactive, fluorogenic, chromogenic or enzymatic moieties. Therefore, possible methods of detection include, but are not limited to, immunocytochemistry; proteomics, such as immunochemistry; cytogenetics, such as in situ hybridization, and fluorescence in situ hybridization; radiodetection, cytometry and field effects, such as MACs and DNA ploidy (the quantitation of stoichiometrically-stained nuclear DNA using automated computerized cytometry) and; cytopathology, such as quantitative cytopathology based on morphology. The signal generated by the labeled probe is preferably of sufficient intensity to permit detection by a medical practitioner or technician.

Once the slide is prepared, a medical practitioner conducts a microscopic review of the slides in order to identify cells that exhibit a change in marker expression characteristic of a diagnosis of cancer. The medical practitioner may use an image analysis system and automated microscope to identify cells of interest. Analysis of the data may make use of an information management system and algorithms that will assist the physician in making a definitive diagnosis and select the optimal therapeutic approach. A medical practitioner may also examine the sample using an instrument platform that is capable of detecting the presence of the labeled agent.

A molecular diagnostic panel assay will result in one or more glass microscope slides with labeled cells and/or tissue sections. The challenge for human experts to assess these (cyto)pathology multilabeled-cell preparations objectively and with clinically meaningful results is a virtually insurmountable detection and perception problem for any human being.

Computer-aided imaging systems (i.e., Photonic Microscopes™) can be developed and used to assess quantitatively and reproducibly the amount and location of probe-labeled cells and tissues. Such Photonic Microscopes™ combine robotic slide-handling capabilities, data management systems (e.g., medical informatics), and quantitative digital (optical and electronic) image analysis hardware and software modules to detect and report cell-based probe content and localization data that cannot be obtained by human visualization with comparable sensitivity and accuracy. These probe data can be used to characterize and differentiate cellular samples based upon their related characteristics and differences in their respective cell-based markers for a variety of disease states.

The present methodology is a methodology whereby the molecular diagnostic panels are applied to cell-based specimens and samples, and whereby computer-aided imaging systems are subsequently used to quantify and report the results of the molecular diagnostic panel tests. Such imaging systems can be used to evaluate cell-based samples in which multiple probes are used simultaneously on a given slide-based sample, and in which the probes can be separately analyzed, quantified, and reported because the probes are differentiated by color on the microscope cytology or histology slide.

The signals generated by a labeled agent in the sample may, if they are of appropriate type and of sufficient intensity, be detected by a human reviewer (e.g., pathologist) using a standard microscope or a Computer-Aided Microscope [167]. The Computer-Aided Microscope is an ergonomic, computer-interfaced microscope workstation that integrates mouse-driven control of microscope operation (e.g., stage movement, focusing) with computerized automation of key functions (e.g., slide scanning patterns). A centralized Data Management System stores, organizes and displays relevant patient information as well as results from all specimen screenings and pathologist reviews. An identification number that is imprinted onto barcodes and affixed to each sample slide uniquely identifies each sample in the database, and relates it to the original specimen and the patient.

In a preferred embodiment the signals generated by a labeled agent in the sample will be detected and quantitated using an automated image analysis system, or Photonic Microscope, interfaced to the centralized Data Management System. The Photonic Microscope provides fully automated software control of the microscope operations and incorporates detectors and other components appropriate for quantitation even of signals not detectable by human reviewers, such as very faint signals or signals from radiolabeled moieties. The location of detected signals is stored electronically for rapid relocation by automated instruments, and for human review using a Computer-Aided Microscope [168].

The centralized Data Management System archives all patient and sample data using the bar-coded identification number. The data may be acquired asynchronously, from a multiplicity of sites, and may be derived from multiple reviews and analyses by human cytologists and/or automated analyzers. These data may include results from multiple sample slides representing aliquots from a single previously homogenized patient specimen. Part or all of the data may be transferred to or from a hospital's Laboratory Information System to meet reporting, archiving, billing or regulatory requirements. A single, comprehensive report with integrated results from panel tests and human reviews may be generated and delivered to the physician in hardcopy, or electronically through networked computers or the Internet.

In some embodiments, the instant method allows for differential discrimination of different diseases, such as different histologic types of cancers. The term "histologic type" refers to specific disease states. Depending on the general disease state there can be one or several histologic types. For example, lung cancer includes, but is not limited to, squamous cell carcinoma, adenocarcinoma, large cell carcinoma, small cell carcinoma and mesothelioma. Knowledge of the histologic type of cancer affecting a patient is very useful because it helps the medical practitioner to localize and characterize the disease and to determine the optical treatment strategy.

In order to determine the specific disease state, a panel of markers is selected that allows for discrimination between specific disease states. For example, within a panel of molecular markers, a pattern of expression may be identified that is indicative of a particular histologic type of cancer. The detection of the level of expression of the panel of molecular markers is achieved by the above-described methods. Preferably, a panel of 1–20 molecular markers is employed to discriminate among the various histologic types of lung cancer. However, most preferably, 4–7 markers are used. Decision trees may be developed to aid in discriminating between different histologic types based on patterns of marker expression.

In addition to allowing for the detection of malignant cells in a cytologic sample, the instant invention has utility in the molecular characterization of the disease state. Such information is often of prognostic significance and can assist the physician in the selection of the optimal therapeutic approach for a particular patient. In addition, the panel of markers described in this invention may have utility in monitoring the patient for either recurrence or to measure the efficacy of the therapy being used to treat the disease.

By way of non-limiting example, the presence of lung cancer may be detected by a lung cancer detection panel and the specific type of lung cancer may be detected by a discrimination panel. If the medical practitioner determines that malignant cells are present in the cytologic sample, a further analysis of the histologic type of lung cancer may be performed. The histologic type of lung cancer encompassed by the present invention includes but is not limited to squamous cell carcinoma, adenocarcinoma, large cell carcinoma, small cell carcinoma and mesothelioma. FIG. 1 illustrates molecular markers that are preferable markers to be included in a panel for identifying different histologic types of lung cancer. The column labeled "%" indicates the percentage of tumor specimens that express a particular marker.

In determining the various histologic types of lung cancer, the relative level of expression of a marker is analyzed. FIG. 2 illustrates how different markers may be used to discriminate among different histologic types of cancer. In this table, SQ indicates squamous cell carcinoma, AD indicates adenocarcinoma, LC indicates large cell carcinoma, SC indicates small cell carcinoma and ME indicates mesothelioma. The numbers appearing in each cell represent frequency of marker change in one cell type versus another. To be included in the table, the ratio must be greater than 2.0 or less than 0.5. A number larger than 100 generally indicates that the second marker is not expressed. In such cases the denominator was set at 0.1 for the purpose of the analysis. Finally, empty cells represent either no difference in expression or the absence of expression data.

One method for analyzing the data collected is to construct decision trees. Schemes 1–4 are examples of decision trees that may be constructed to enable a differential determination of a histologic type of lung cancer using the patterns of expression. The present invention is in no way limited to the decision trees presented in Schemes 1–4. The relative level of expression of a marker can be higher, lower, or the same (ND) as the level of expression of the molecular marker in a malignant cell of a different histologic type. Each scheme enables a distinction between five histologic types of lung cancer through the use of the indicated panel of molecular markers.

For example, in Scheme 1 the panel consists of HERA, MAGE-3, Thrombomodulin and Cyclin D1. First the sample is contacted with a labeled probe directed toward HERA. If the expression of HERA is lower than the control, the test indicates that the histologic type of lung cancer is mesothelioma (ME). If, however, the expression is higher or the same as the control, the sample is contacted with a probe directed toward MAGE-3. If the expression of MAGE-3 is lower than the control, the sample is contacted with a labeled probe directed toward Cyclin D1 and a determination of small cell carcinoma (SC) or adenocarcinoma (AD) is possible. If the expression of MAGE-3 is higher than or the same as the control, the sample is contacted with a labeled probe directed toward Thrombomodulin and a determination of squamous cell carcinoma (SC) or large cell carcinoma (LC) is possible.

Scheme 1

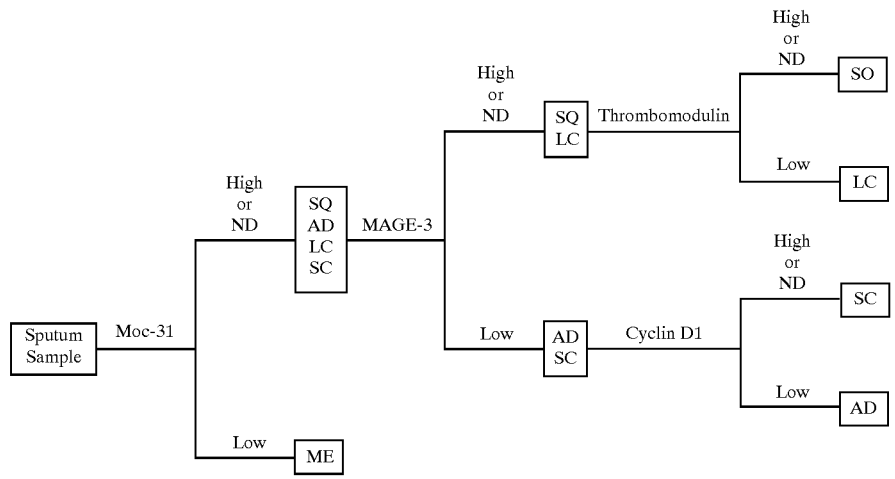

In Scheme 2 the panel consists of E-Cadherin, Pulmonary Surfactant B and Thrombomodulin. First the sample is contacted with a labeled probe directed toward E-Cadherin. If the expression of E-Cadherin is lower than the control, the test indicates that the histologic type of lung cancer is mesothelioma (ME). If, however, the expression is higher or the same as the control, the sample is contacted with a probe directed toward Pulmonary Surfactant B. If the expression of Pulmonary Surfactant B is lower than the control, the sample is contacted with a labeled probe directed toward Thrombomodulin and a determination of squamous cell carcinoma (SQ) or large cell carcinoma (LC) is possible. If the expression of Pulmonary Surfactant B is higher than or the same as the control, the sample is contacted with a labeled probe directed toward CD44v6 and a determination of adenocarcinoma (AD) and small cell carcinoma (SC) is possible. (See Schemes 3 and 4 for more examples of decision trees).

Scheme 2
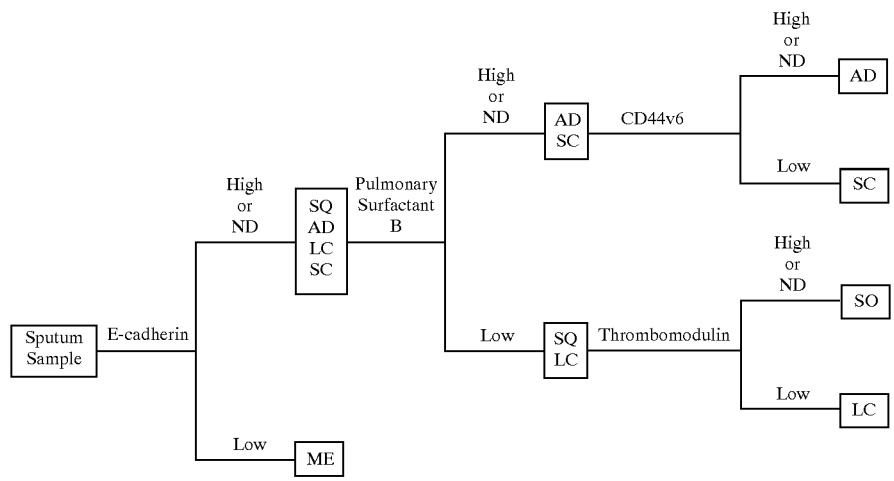
Scheme 3
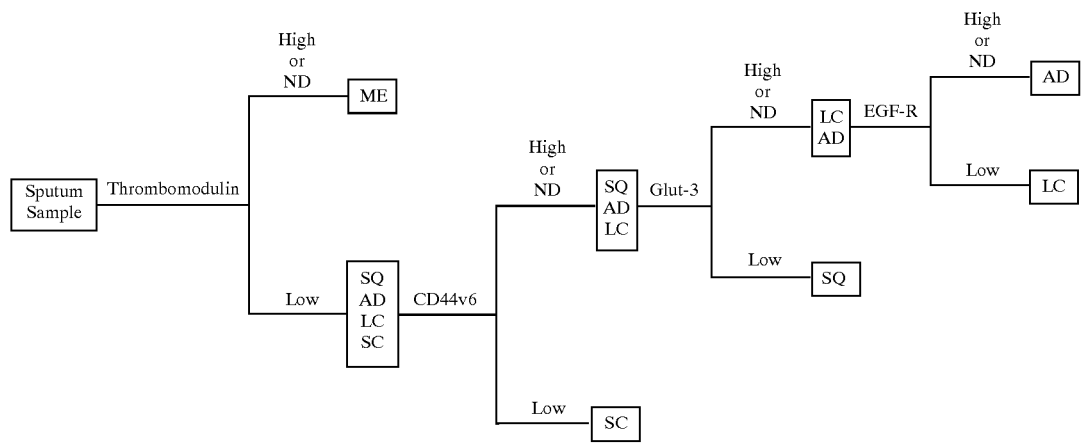
Scheme 4
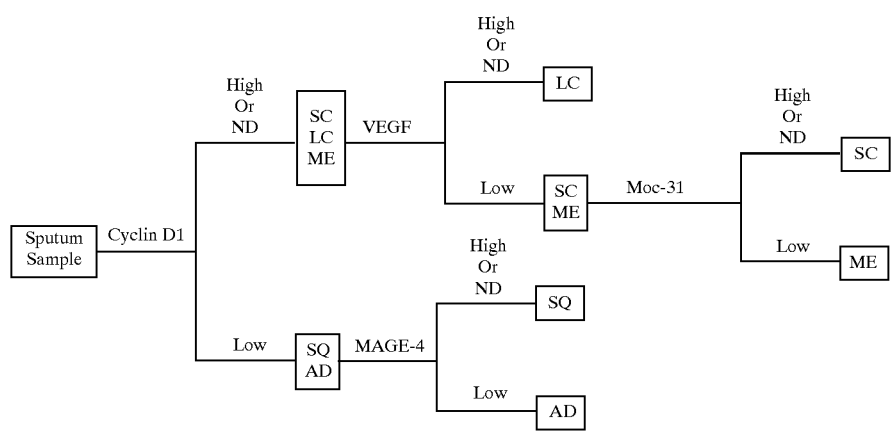

A preferred method involves using panels of molecular markers where differences in the pattern of expression permits the discrimination between the various histologic type of lung cancer.

Many different decision trees may be constructed to analyze the patterns of marker expression. This information may be used by physicians or other healthcare providers to make patient management decisions and select an optimal treatment strategy.

5. Reporting of Results of Panel Analysis

The results from the panel analysis may be reported in several ways. For example, the results may be reported as a simple "yes or no" result. Alternatively, the result may be reported as a probability that the test results are correct. For example, the results from a detection panel study may indicate whether a patient has a generic disease state or not. As the panel also reports the specificity and sensitivity, the results may also be reported as the probability that the patient has a generic disease state. The results from a discrimination panel analysis will discriminate among specific disease states. The results may be reported as a "yes or no" with respect to whether the specific disease state is present. Alternatively, the results may be reported as a probability that a specific disease state is present. It is also possible to perform several discrimination panel analyses on a specimen from one patient and report a profile of the probabilities that the disease state present is a specific disease state with respect to the other possibilities. The other possibilities may also include false positives.

In embodiments in which a profile of the probabilities of each specific disease state being present is produced, there are several possible outcomes. For example, it is possible that all of the probabilities will be a very small probability. In this instance, it is possible that the doctor will conclude that the patient's specimen diagnosis is a false positive. It is also possible that all of the probabilities will be low except for one that is above 80–90%. In this instance, it is possible that the doctor will conclude that the test verifies that the patient has the specific disease state that indicated the high probability. It is also possible that most of the probabilities will be low, but similarly high probabilities are reported for two specific disease states. In this case, a doctor may recommend more extensive panel testing to ensure that the correct disease state is identified. Another possibility is that all of the probabilities reported will be low, with one being slightly higher than the rest but not high enough to be in the 80–90% range. In this case, a doctor may recommend more extensive panel testing to ensure that the correct disease state is identified and/or to rule out metastatic cancer from a remote primary tumor of a different cancer type.

The following Example is illustrative of the method of the invention for selecting a disease detection panel, disease discrimination panels, validation of the panels and use of the panels in the clinic to screen for a disease and to discriminate among different subtypes of the disease. Lung cancer was selected for this illustrative example, in part because of its importance to world health, but it will be appreciated that similar procedures will apply to other types of cancer, as well as to infectious, degenerative and autoimmune diseases, according to the foregoing general disclosure.

ILLUSTRATIVE EXAMPLE

The present method was used to develop lung cancer detection panels as well as single lung cancer type specific discrimination panels. Lung cancer is an extremely complex collection of diseases that can be segregated into two main classes. Non-small cell lung carcinoma (NSCLC) that accounts for approximately 70 to 80% of all lung cancers can be further subdivided into three main histologic types including squamous cell carcinoma, adenocarcinoma, and large cell carcinoma. The remaining 20 to 30% of lung cancer patients present with small cell lung carcinoma (SCLC). In addition, malignant mesothelioma of the pleural space, can develop in individuals exposed to asbestos and will often spread widely invading other thoracic structures. Different forms of lung cancer tend to localize in different regions of the lung, have different prognoses, and respond differently to various forms of therapy.

According to the latest statistics from the World Health Organization (Globocan 2000), lung cancer has become the most common fatal malignancy in both men and women with an estimated 1.24 million new cases and 1.1 million deaths each year. In the U.S. alone, the National Cancer Institute reports that there are approximately 186,000 new cases of lung cancer and each year 162,000 people die of the disease, accounting for 25% of all cancer-related deaths. In the U.S., overall 1-year survival for patients with lung cancer is 40%, however, only 14% live 5 years. In other parts of the world, 5-year survival is significantly lower (5% in the UK). The high mortality of lung cancer can be attributed to the fact that most patients (85%) are diagnosed with advanced disease when treatment options are limited and the disease is likely to have metastasized. In these patients, 5-year survival is between 2–30% depending of the stage at the time of diagnosis. This is in sharp contrast to cases where patients are diagnosed early and 5-year survival is greater than 75%. While it is true that a number of new chemotherapeutic agents have been introduced into clinical practice for the treatment of advanced lung cancer, to date, none have yielded a significant improvement in long-term survival. Even though patients with early stage disease can presumably be cured by surgery, they remain at significant risk, as there is a high probability that they will develop a second malignancy. Thus, for the lung cancer patient, early detection and treatment followed by aggressive monitoring provides the best chance of achieving significant improvements in long-term survival along with a reduction in morbidity and cost.

At the present time, a patient is suspected of having lung cancer either because of a suspicious lesion on X-ray or because the patient becomes symptomatic. As a result, most patients are diagnosed with relatively late stage disease. In addition, because most methods lack sufficient sensitivity with respect to the detection of early stage disease, the current policy of the U.S. National Cancer Institute (NCI), National Institutes of Health, recommends against screening for lung cancer even in populations of patients who are at significant risk. In this embodiment of the present invention, however, sputum cytology is employed to provide a relatively noninvasive, more effective and cost-effective means for the early detection of lung cancer.

The specificity of sputum cytology is relatively high. Recent studies have indicated that experienced cytotechnologists are able to recognize malignant or severely dysplastic cells with a high degree of accuracy and reliability [10]. While the detection rate can be as high as 80 to 90% when samples are collected from patients with a relatively advanced disease [11,12], overall, sputum cytology has a sensitivity of only 30–40% [13,14]. The low sensitivity of sputum cytology is particularly important given that obtaining and preparing the specimen can be relatively expensive. Furthermore, failing to detect a malignancy can significantly delay treatment thereby reducing the chance of achieving a cure.

The selection of an "at-risk" population can also influence the value of sputum cytology as a screening tool. Individuals who are at significant risk include those with a prior diagnosis of lung cancer, long-term smokers or former smokers (>30 pack years) and individuals with long-term exposure to asbestos or pulmonary carcinogens. People with a genetic predisposition or familial history are also included in an "at-risk" population. Such individuals are likely to benefit from testing. While the inclusion of individuals with lower risk may result in an increase in the absolute number of cases detected, it would be hard to justify the substantial increase in healthcare costs.

Other factors that contribute to the relatively poor performance of conventional sputum cytology include the location of the lesion, tumor size, histologic type, and the quality of the sample. Squamous-cell carcinoma accounts for 31% of all primary pulmonary neoplasms. Most of these tumors arise from segmental bronchi and extend to the proximal lobar and distal subsegmental branches [15]. For this reason, sputum cytology is reasonably effective (79%) in detecting these lesions. Currently, squamous cell carcinoma is viewed as the only type of lung cancer that is amenable to cytologic detection in an in situ and radiologically occult stage [15], as sloughed cells are more likely to be available for evaluation. In one large study where patients were followed with both chest X-ray and sputum cytology, 23% of all lung cancers were detected by cytology alone, suggesting that the tumors were early stage and radiologically occult [16]. In another study [17], sputum cytology detected 76% of patients with radiologically occult tumors.

In the case of adenocarcinoma, 70% of tumors occur in the periphery of the lung making it less likely that malignant cells will be found in a conventional sputum specimen. For this reason, adenocarcinomas are rarely detected by sputum cytology (45%) [12,18,19], an important consideration, since the incidence of adenocarcinoma appears to be increasing, particularly in women [20–22].

Tumor size can also affect the likelihood of achieving a correct diagnosis, a factor that is particularly important when considering a screening test for the detection of disease in asymptomatic individuals. While there is only a 50% chance that tumors <24 mm will be read as a true positive, the probability of detecting a larger lesion is in excess of 84% [12].

Recent reports also indicate that the cellularity of the specimen will affect the sensitivity of sputum cytology [14,23]. In general, patients with squamous cell carcinoma produce specimens with significant numbers of tumor cells, thereby increasing the likelihood of a correct diagnosis [14,23]. For patients with adenocarcinoma, the presence of tumor cells in a sputum specimen is reported to be less than 10% in 95% of the specimens and less than 2% in 75% of specimens, making the diagnosis significantly more difficult.

The degree of differentiation can also influence the ability of a pathologist to detect malignant cells, particularly in cases of adenocarcinoma. Well-differentiated tumor cells frequently resemble nonneoplastic respiratory epithelial cells. In the case of small-cell lung carcinoma, sputum samples often contain nests of loosely aggregated cells that have a distinct appearance. However, techniques currently used to process sputum samples tend to disaggregate the cells, making a diagnosis more difficult.

Sample quality is another factor that can contribute to the low sensitivity of sputum cytology. Recent reports suggest that it is possible to obtain adequate samples from 70–85% of subjects. However, achieving this measure of success often requires that patients provide multiple specimens [13]. This procedure is inconvenient, time-consuming and costly. Patient compliance is also generally low, as patients are frequently asked to collect over several days [13]. Of equal importance is the observation that former smokers, while at significant risk for developing lung cancer, often fail to produce an adequate specimen. Sample preservation and processing is another critical factor that can affect the value of sputum cytology as a diagnostic test.

Lastly, even if adequate samples could be obtained and optimally prepared, cytotechnologists generally still have to review 2–4 slides per specimen, each typically taking up to four minutes [24]. Given the low sensitivity, high technical complexity and labor intensity of conventional sputum cytology, it is not surprising that this test has been almost universally rejected as a population-based screen for the early detection of lung cancer [25].

Even if these technical issues were resolved, the low sensitivity of sputum cytology remains a significant problem. The high incidence of false negative results can significantly delay the patient receiving potentially curative therapy. While it may be possible to develop tests with greater sensitivity, such improvements must not come at the cost of specificity. An increase in the number of false positive results would subject patients to unnecessary, often invasive and costly, follow-up and would have a negative impact on the patient's quality of life. The present invention overcomes many of the limitations associated with previous methods of early cancer detection, including those related to the use of sputum cytology for the early detection of lung cancer.

Lung cancer is a heterogeneous collection of diseases. To ensure that a test has the necessary level of sensitivity and specificity to justify its use as a population based screen, the present invention envisions using, for example, a library of 10 to 30 cellular markers to develop panels. Selection of the library of this invention was based on a review and reanalysis of the relevant scientific literature where, in most cases, marker expression was measured in biopsy specimens taken from patients with lung cancer in an attempt to link expression with prognosis.

For example, a preferred panel for early detection, characterization, and/or monitoring of lung cancer in a patient's sputum may include molecular markers for which a change in expression occurred in at least 75% of tumor specimens. An exemplary panel includes markers selected from VEGF, Thrombomodulin, CD44v6, SP-A, Rb, E-Cadherin, cyclin A, nm23, telomerase, Ki-67, cyclin D1, PCNA, MAGE-1, Mucin, SP-B, HERA, FGF-2, C-MET, thyroid transcription factor, Bcl-2, N-Cadherin, EGFR, Glut-1, ER-related (p29), MAGE-3 and Glut-3. A most preferred panel includes molecular markers for which a change in expression occurs in more than 85% of tumor specimens. An exemplary panel includes molecular markers selected from Glut1, HERA, Muc-1, Telomerase, VEGF, HGF, FGF, E-cadherin, Cyclin A, EGF Receptor, Bcl-2, Cyclin D1 and N-cadherin. With the exception of Rb and E-cadherin, a diagnosis of lung cancer is associated with an increase in marker expression. A brief description of the library of probes/markers utilized in the present example is provided below in Table 4. It is noted that the numbering of the antibodies in the table below is consistent with the number of the antibodies/probes/markers throughout this example.

TABLE 4

Probes and Markers for Lung Panel

| No. | Marker Abbreviation | Full Name of Antibody Probe | Target Marker Name/Description |
|---|---|---|---|
| 1 | VEGF | anti-VEGF | Vascular Endothelial Growth Factor protein |
| 2 | Thrombomodulin | anti-Thrombomodulin | trams-membrane glycoprotein |
| 3 | CD44v6 | anti-CD44v6 | cell surface glycoprotein (CD44 variant 6 gene): cell adhesion molecule |
| 4 | SP-A | anti-Surfactant Apoprotein A | pulmonary surfactant apoprotein |
| 5 | Retinoblastoma | anti-Retinoblastoma gene product | phosphoprotein |
| 6 | E-Cadherin | anti-E-Cadherin | transmembrane $Ca^{++}$ dependent cell adhesion molecule |
| 7 | Cyclin A | anti-Cyclin A | protein subunit of cyclin-dependent kinase enzymes: for cell cycle regulatic |
| 8 | nm23 | anti-nm23 | 2 closely related proteins produced by nm23-H1 and -H2 genes |
| 9 | Telomerase | anti-Telomerase | ribonucleoprotein enzyme for chromosome repair |
| 10 | Mib-1 (Ki-67) | anti-Ki-67 | nuclear protein: expressed in proliferating cells |
| 11 | Cyclin D1 | anti-Cyclin D1 | protein subunit of cyclin-dependent kinase enzymes: for cell cycle regulatic |
| 12 | PCNA | anti-Proliferating Cell Nuclear Antigen | protein cofactor for DNA polymerase delta |
| 13 | MAGE-1 | anti-Melanoma-Associated Antigen 1 | cell recognition protein coded by MAGE family of genes |
| 14 | Mucin 1 (MUC-1) | anti-Mucin 1 | cell surface and secreted mucin (highly glycosylated protein) |
| 15 | SP-B | anti-mature Surfactant Apoprotein B | pulmonary surfactant apoprotein |
| 16 | HERA | anti-Human Epithelial Related Antigen (MOC-31) | cell surface antigen (transembrane protein) |
| 17 | FGF-2 (basic FGF) | anti-Fibroblast Growth Factor | protein that binds to cell surface |
| 18 | c-MET | anti-c-MET | trans-membrane receptor protein for Hepatocyte Growth Factor (HGF) |
| 19 | Thyroid Transcription Factor 1 | anti-TTF-1 | regulator of thyroid-specific genes: also expressed in lung |
| 20 | BCL-2 | anti-BCL2 | intracellular membrane-bound protein encoded by BCL2 gene |
| 21 | P120 | anti-p120 | Proliferation-Associated Nucleolar Antigen protein |
| 22 | N-Cadherin | anti-N-Cadherin | transmembrane $Ca^{++}$ dependent cell adhesion molecule |
| 23 | EGFR | anti-EGFR | Epidermal Growth Factor Receptor: transmembrane glycoprotein |
| 24 | Glut 1 | anti-Glut 1 | Glucose-transporting, transmembrane Glut family of proteins |
| 25 | ER-related (p29) | anti-ER-related P29: anti-HSP 27 | Estrogen Receptor-related p29 protein: Heat Shock protein 27 |
| 26 | Mage 3 | anti-Melanoma-Associated Antigen 3 | cell recognition protein coded by MAGE family of genes |
| 27 | Glut 3 | anti-Glut 3 | Glucose-transporting, transmembrane Glut family of proteins |
| 28 | PCNA (higher dilution) | anti-Proliferating Cell Nuclear Antigen | protein cofactor for DNA polymerase delta |

Each molecular marker in the preferred panel is described below. Table 5, reciting the percentage of expression of the markers in tissue for each type of lung cancer is provided at the end of this section.

Glucose Transporter Proteins (Glut 1 and Glut 3) [26–28]

Glucose Transporter-1 (Glut 1) and Glucose Transporter-3 (Glut-3) are a ubiquitously expressed high affinity glucose transporter. Tumor cells often display higher rates of respiration, glucose uptake, and glucose metabolism than do normal cells, and the elevated uptake of glucose in tumor cells is thought to be mediated by glucose transporters. Overexpression of certain types of GLUT isoforms has been reported in lung cancer. The cellular localization of Glut 1 is in the cell membrane. GLUT-1 and GLUT-3 are disease markers useful for detection of a disease state.

Malignant cells exhibit an increase in glucose uptake that appears to be mediated by a family of glucose transporter proteins (Gluts). Oncogenes and growth factors appear to regulate the expression of these proteins as well as their activities. Members of the Glut family of proteins exhibit different patterns of distribution in various human tissues and rapid proliferation is often associated with their overexpression. Recent evidence suggests that Glut1 is expressed by a large percentage of NSCLC and by a majority of SCLC.

While the expression of Glut 3 is relatively low in both NSCLC and SCLC a significant percentage (39.5%) of large cell carcinomas express the protein. In stage I tumors, 83% express Glut1 at some level with 75–100% of cells staining in 25% of cases. These data would suggest that Glut1 overexpression is a relatively early event in tumor progression. Glut1 immunoreactivity has also been detected in >90% of stage II and IIIA cancers. There also appears to be an inverse correlation between Glut1 and Glut3 immunoreactivity and tumor differentiation. Tumors expressing high levels of Glut1 appear to be particularly aggressive that are associate with a poor prognosis. In cases were tumors were negative for the proteins better survival was observed.

Human Epithelial Related Antigen (HERA) [29,30]

HERA is a transmembrane glycoprotein with an, as yet, unknown function. HERA is present on most normal and malignant epithelia. Recent reports suggest that the while HERA expression is high in all histologic types of NSCLC making it useful as a detection marker. In contrast HERA expression is absent in mesothelioma and thus suggesting would have utility as a discrimination marker. The cellular localization of HERA is the cell surface.

Basic Fibroblast Growth Factor (FGF) [31–34]

Basic Fibroblast Growth Factor (FGF) is a polypeptide growth factor with a high affinity for heparin and other glycosaminoglycans. In cancer, FGF functions as a potent mitogen, plays a role in angiogenesis, differentiation, and proliferation, and is involved in tumor progression and metastasis. FGF overexpression frequently occurs in both SCLC and squamous cell carcinoma. In many cases (62%), the cells also express the FGF receptor suggesting the presence of an autocrine loop. Forty-eight percent of Stage 1 tumors overexpress FGF. The frequency of FGF in Stage II lung cancer is 84%. Expression of either the growth factor or its receptor was associated with the poor prognosis. Five-year survival rates for those patients with stage I disease were 73% for those expressing FGF versus 80% for those who were FGF negative. The cellular localization is the cell membrane.

Telomerase [35–42]

Telomerase is a ribonucleoprotein enzyme that extends and maintains telomeres of eukaryotic chromosomes. It consists of a catalytic protein subunit with reverse transcriptase activity and an RNA subunit with reverse transcriptase activity and an RNA subunit that serves as the template for telomere extension. Cells that do not express telomerase have successively-shortened telomeres with each cell division, which ultimately leads to chromosomal instability, aging and cell death. The cellular localization of telomerase is nuclear.

Expression of telomerase appears to occur in immortalized cells and enzyme activity is a common feature of the malignant phenotype. Approximately 80–94% of lung tumors exhibit high levels of telomerase activity. In addition, 71% of hyperplasia, 80% of metaplasia, and 82% of dysplasia express enzyme activity. All the carcinoma in situ (CIS) specimens exhibit enzyme activity. The low levels of expression in premaligant tissues is probably related to the fact that only a small percentage of cells (5 and 20%) in the sample express enzyme activity. This is in contrast to tumors where 20–60% of cells may express enzyme activity. Based on a limited number of samples it would appear expression of telomerase activity is also common in SCLC.

Proliferating Cell Nuclear Antigen (PCNA) [43–51]

PCNA functions as a cofactor for DNA polymerase delta. PCNA is expressed in both S phase of the cell cycle and during periods of DNA synthesis associated with DNA repair. PCNA is expressed in proliferating cells in a wide range of normal and malignant tissues. The cellular localization of PCNA is nuclear.

Expression of PCNA is a common feature of rapidly dividing cells and is detected in 98% of tumors. Immunohistochemical staining is nuclear with moderate to intense staining detected in 83% of NSCLC. Intense PCNA staining was observed in 51% of p53-negative tumors. However, when both PCNA (>50% of cells staining) and p53 are overexpressed (>10% of cells stained) the prognosis tends to be poorer with a shorter time to progression. Although frequently detected in all stages of lung cancer, intense staining for PCNA is more common in metastatic disease. Thirty-one percent of CIS also overexpress PCNA.

CD44 [51–58]

CD44v6 is a cell surface glycoprotein that acts as a cellular adhesion molecule. It is expressed on a wide range of normal and malignant cells in epithelial, mesothelial and hematopoietic tissues. The expression of specific CD44 splice variants has been shown to be associated with metastasis and poor prognosis in certain human malignancies. It is expected to be used for detection and discrimination between squamous cell carcinoma and adenocarcinoma. CD44 is a cell adhesion molecule that appears to play a role in tumor invasion and metastasis. Alternative splicing results in the expression of several variant isoforms. CD44 expression is generally lacking in SCLC and is variably expressed in NSCLC. Highest levels of expression occur in squamous cell carcinoma, thus making it valuable in discriminating between tumor types. In non-neoplastic tissue, CD44 staining is observed in bronchial epithelial cells, macrophages, lymphocytes, and alveolar pneumocytes. There was no significant correlation between CD44 expression and tumor stage, recurrence, or survival particularly when overexpression occurs in early stage disease. In metastatic lesions 100% of squamous cell carcinoma and 75% of adenocarcinoma showed strong CD44v6 positivity. These data would tend to indicate that changes in CD44 expression occur relatively late in tumor progression that could limit its value as an early detection marker. Recent findings suggest that the CD44v8–10 variant is expressed by a majority of NSCLC making it a possible candidate marker.

Cyclin A [59–62]

Cyclin A is a regulatory subunit of the cyclin-dependent kinases (CDK's) which control the transition points at specific phases of the cell cycle. It is detectable in S phase and during progression into G2 phase. The cellular localization of Cyclin A is nuclear.

Protein complexes consisting of cyclins and cyclin-dependent kinases function to regulate cell cycle progression. Changes in cyclin expression are associated with genetic alterations affecting the CCDN1 gene. While -the cyclins act as regulatory molecules, the cyclin-dependent kinases function as catalytic subunits activating and inactivating Rb.

Immunohistochemical analysis has revealed that the overexpression of the cyclins is associated with an increase in cellular proliferation as indicated by a high Ki-67 labeling index. Cyclin overexpression occurs in 75% of NSCLC and appears to occur relatively early in tumor progression. Recent reports indicate that 66.7% of stage I/II and 70.9% of stage III tumors overexpress Cyclin A. Nuclear staining is common in poorly differentiated tumors. Expression of cyclin A is often associated with a decrease in mean survival time and a tendency towards the development of drug resistance. However, increased expression has also been associated with a greater response to doxorubicin.

Cyclin D1 [63–73]

Cyclin D1, as with Cylcin A, is a regulatory subunit of the cyclin-dependent kinases (CDK's) which control the transition points at specific phases of the cell cycle. Cyclin D1 regulates the entry of cells into S phase of the cell cycle. This gene is frequently amplified and/or its expression deregulated in a wide range of human malignancies. The cellular localization of Cyclin D1 is nuclear.

Like Cyclin A, cyclin D1 functions to regulate cell cycle progression. Staining of cyclin D1 is predominately cytoplasmic and independent of histologic type. Reports suggest that cyclin D1 overexpression occurs in 40–70% of NSCLC and 80% of SCLC. Cyclin D1, staining was observed in 37.9% of stage I, 60% stage II, and 57.9% of stage III tumors. Cyclin D1 expression has also been seen in dysplastic and hyperplastic tissue providing evidence that these changes occur relatively early in tumor progression. Patients who overexpress cyclin D1 exhibit shorter mean survival time and lower five-year survival rate.

Hepatocyte Growth Factor Receptor (C-MET) [74–77]

C-MET is a proto-oncogene that encodes a transmembrane receptor tyrosine kinase for HGF. HGF is a mitogen for hepatocytes and endothelial cells, and exerts pleitrophic activity on several cell types of epithelial origin. The cellular localization of C-MET is the cell surface.

Hepatocyte growth factor/scatter factor (HGF/SF) stimulates a broad spectrum of epithelial cells causing them to proliferate, migrate, and carry out complex differentiation programs including angiogenesis. HGF/SF binds to a receptor encoded by the c-MET oncogene. While both normal and malignant tissues express the HGF receptor, expression of HGF/SF appears to be limited to malignant tissue.

While the human lung generally expresses low levels of HGF/SF, expression increases markedly in NSCLC. Using Western blot analysis, 88.5% of lung cancers exhibited an increase in the protein expression. All histologic types of tumors expressed the protein at increased concentrations. While increased levels of protein occur in all stages of the disease, recent evidence suggests that in addition to the cancer cells, stromal cells and/or inflammatory cells may be responsible for the production of the growth factor.

Mucin—MUC-1 [78–82]

Mucin-1 comes from a family of highly glycosylated secretory proteins which comprise the major protein constituents of the mucous gel which coats and protects the tracheobronchial tree, gastrointestinal tract and genitourinary tract. Mucin-1 is a typically expressed in epithelial tumors. The cellular localization of Mucin-1 is cytoplasm and the cell surface.

Mucins are a family of high molecular weight glycoproteins that are synthesized by a variety of secretory epithelial cells that are either membrane bound or secreted. Within the respiratory tract, these proteins contribute to the mucus gel that coats and protects that tracheobronchial tree. Changes in mucin expression commonly occur in conjunction with malignant transformation including lung cancer. Evidence exists suggesting at these changes may contribute to alterations in cell growth regulation, recognition by the immune system, and the metastatic potential of the tumor.

Although normal lung tissue expresses MUC-1, significantly higher levels of expression are found in lung cancer with highest levels occurring in adenocarcinoma. Staining appears to occur independently of stage and is more common in smokers than in former smokers or nonsmokers. Some premalignant lesions also exhibit increased MUC-1 expression.

Thyroid Transcription Factor-1 (TTF-1) [83,84]

TTF-1 belongs to a family of homeodomain transcription factors that activate thyroid-specific and pulmonary-specific differentiation genes. The cellular localization of TTF-1 is nuclear.

TTF-1 is a protein originally found to mediate the transcription of thyroglobulin. Recently, TTF-1 expression was also found in the diencephalon and brohchioloalveolar epithelium. Within the lung TTF-1 functions as a transcription factor regulating the synthesis of surfactant proteins and clara secretory protein. Overexpression of TTF-1 occurs in a large proportion of lung adenocarcinomas and can aid in distinguishing between primary lung cancer and cancers that metastasize to the lung. Adenocarcinomas that express TTF-1 and are cytokeratin 7 positive and cytokeratin 20 negative can be detected with 95% sensitivity.

Vascular Endothelial Growth Factor (VEGF) [33,61, 85–89]

VEGF plays an important role in angiogenesis, which promotes tumor progression and metastasis. There are multiple forms of VEGF; the two smaller isoforms are secreted proteins and act as diffusible agents, whereas the larger two remain cell associated. The cellular localization of VEGF is cytoplasmic, cell surface, and extracellular matrix.

Vascular Endothelial Growth Factor (VEGF) is an important angiogenesis factor and endothelial cell-specific mitogen. Angiogenesis is an important process in the latter stages of carcinogenesis, tumor progression and is particularly important in the development of distant metastasis. VEGF binds to a specific receptor Flt that is often present in the tumors expressing the growth factor suggesting the presence of an autocrine loop.

Immunohistochemical analysis reveals that cells expressing VEGF exhibit a pattern of staining that is diffuse and cytoplasmic. While not expressed by nonneoplastic cells, VEGF is present in the majority of NSCLC and in a smaller percentage of SCLC. Several reports have shown high levels of VEGF in early stage lung cancer.

Expression of VEGF has been associated with an increased frequency of metastasis. Studies have shown that VEGF expression is indicative of a poor prognosis and shorter disease-free interval in adenocarcinoma but not in squamous cell carcinoma. Three year and five year survival rates in the group expressing high levels of VEGF were 50% and 16.7% as compared to 90.9 and 77.9% respectively for the low VEGF group.

Epidermal Growth Factor Receptor (EGFR) [90–104]

Epidermal Growth Factor Receptor (EGFR) is a transmembrane glycoprotein, which can bind and become activated by various ligands. Binding initiates a chain of events that result in DNA synthesis, cell proliferation, and cell differentiation. EGFR has been demonstrated in a broad spectrum of normal tissues, and EGFR overexpression is found in a variety of neoplasms. Increased expression has been observed in adenocarcinomas of the lung and large cell carcinomas but not in small cell lung carcinomas. The cellular localization of EGFR is the cell surface.

The EGFR plays an important role in cell growth and differentiation. The EGFR is uniformly present in the basal cell layer but not in more the superficial layers of histologically normal bronchial epithelium. With this exception, there is no consistent staining of normal tissue. Recent evidence suggests that the overexpression of the EGF receptor may not be an absolute requirement for the development of invasive lung cancer. However, it appear that in cases where EGFR overexpression occurs it is a relatively early event with greater staining intensity in more advanced disease.

For patients with invasive carcinomas, 50–77% of tumors stain for EGF. Overexpression of the EGFR is more common in squamous cell carcinoma than in adenocarcinoma and common in SCLC. Highest levels of EGFR occur in conjunction with late stage and metastatic disease that have approximately twice the concentration of EGFR as that seen in stage I/II tumors. Estimates suggest that the level of the EGFR observed in stage I tumors is approximately twice that seen in normal tissue. In addition, 48% of bronchial lesions also show EGFR staining including, metaplasia, atypia, dysplasia, and CIS. In the "normal" bronchial mucosa, of these same cancer patients, overexpression of the EGFR was observed in 39% of cases but was absent in the bronchial epithelium of the non-cancer. In addition, overexpression of the EGFR occurs more frequently in the tumors of smokers than in nonsmokers, particularly in the case of squamous cell carcinoma.

While several studies have suggested that overexpression of the EGFR is associated with the poor prognosis, other studies have failed to make this correlation.

Nucleoside Diphosphate Kinase/nm23 [105–111]

Nucleoside diphosphate kinase (NDP kinase)/nm23 is a nucleoside diphosphate kinase. Tumor cells with high metastatic potential often lack or express only a low amount of nm23 protein, hence the nm23 protein has been described as a metastasis suppressor protein. The cellular localization of nm23 is nuclear and cytoplasmic.

Expression of nm23/nucleoside diphosphate/kinase A (nm23) is a marker of tumor progression where there is an inverse relationship between expression and metastatic potential. In cases where stage I tumors overexpress nm23, no evidence of metastasis was seen during an average follow-up period of 35 months. Immunohistochemical analysis reveals staining that is diffuse, cytoplasmic and generally limited to malignant cells. Alveolar macrophages also express the protein. Given that high levels of expression are associated with a low metastatic potential, there is currently no explanation as to why normal epithelial cells do not express nm23.

Intense staining has been observed in high percentage of NSCLC particularly large cell lung cancer and 74% of SCLC suggesting that this protein plays an important role in tumor progression. With the exception of squamous cell carcinoma, staining intensity tends to increase with stage. Based on the available evidence, it would appear that nm23 is a prognostic factor in both SCLC and NSCLC.

Bcl-2 [101,112–125]

Bcl-2 is a mitochondrial membrane protein that plays a central role in the inhibition of apoptosis. Overexpression of bcl-2 is a common feature of cells in which programmed cell death has been arrested. The cellular localization of Bcl-2 is the cell surface.

Bcl-2 is a protooncogene believed to play a role in promoting the terminal differentiation of cells, prolonging the survival of non-cycling cells and blocking apoptosis in cycling cells. Bcl-2 can exist as a homodimers or can form a heterodimer with Bax. As a homodimer, Bax functions to induce apoptosis. However, the formation of a Bax-bcl-2 complex blocks apoptosis. By blocking apoptosis, bcl-2 expression appears to confer a survival advantage upon affected cells. Bcl-2 expression may also play a role in the development of drug resistance. The expression of bcl-2 is negatively regulated by p53.

Immunohistochemistry analysis of bcl-2 reveals a heterogeneous pattern of cytoplasmic staining. In adenocarcinoma, expression of bcl-2 was significantly associated with smaller tumors (<2 cm) and lower proliferative activity. The expression of bcl-2 appears to be more closely associated with neuroendocrine differentiation and occurs in a large percentage of SCLC.

Overexpression of bcl-2 is not present in preneoplastic lesions suggesting that changes in bcl-2 occur relatively late in tumor progression. In addition to tumor cells, bcl-2 immunostaining also occurs in basal cells and on the luminal surfaces of normal bronchioles but is generally not detected in more differentiated cell types.

Association of bcl-2 immunoreactivity with improved prognosis in NSCLC is controversial. Several reports of suggested that patients with tumors expressing bcl-2 have a superior prognosis and a longer time to recurrence. Several reports indicate that bcl-2 expression tends to be lower in those patients who develop metastatic disease. For patients with squamous cell carcinoma, expression of bcl-2 has been linked to an improvement in 5-year survival. However, in three relatively large studies there was no survival benefit linked to bcl-2 expression, particularly for patients with early stage disease.

Estrogen Receptor-Related Protein (p29) [126]

ER related protein p29 is an estrogen-related heat shock protein that has been found to correlate with the expression of estrogen-receptor. The cellular localization of p29 is cytoplasmic.

Estrogen-dependent intracellular processes are important in the growth regulation of normal tissue and may play a role in the regulation of malignancies. In one study expression of p29 was detected in 109 (98%) of 111 lung cancers. The relation between p29 expression and survival time was different for men and women. Expression of p29 was associated with poorer survival particularly in women with Stage I and II disease. There was no correlation between p29 expression and long-term survival in men.

Retinoblastoma Gene Product (Rb) [68,73,123,127–141]

Retinoblastoma Gene Product (Rb) is a nuclear DNA-binding phosphoprotein. Under phosphorylated Rb binds oncoproteins of DNA tumor viruses and gene regulatory proteins thus inhibiting DNA replication. Rb protein may act by regulating transcription; loss of Rb function leads to uncontrolled cell growth. The cellular localization of Rb is nuclear.

Retinoblastoma protein (pRb) is a protein that is encoded by the retinoblastoma gene and is phosphorylated and dephosphorylated in a cell cycle dependent manner. pRb is considered an important tumor suppressor gene that functions to regulate the cell cycle at G0/G1. In its hypophosphorylated state, pRb inhibits the transition from G1 to S. During G1, inactivation of the growth suppressive properties of pRb occurs when the cyclin dependent kinases (CDK's) phosphorylate the protein. The hyperphosphorylation of pRb prevents it from forming a complex with E2F that functions as a transcription factor proteins that are required for DNA synthesis.

Inactivation of the retinoblastoma (Rb) gene has been documented in various types of cancer, including lung cancer. Small-cell carcinomas fail to stain for pRb indicating loss of Rb function. Overall, 17.6% of the tumors fail to express pRb with no correlation being seen with respect to stage or nodal status. A reduction in staining has also seen in 31% dysplastic bronchial biopsies. However, there appears to be no correlation between pRb expression and the severity of dysplasia. In contrast, normal bronchial epithelium and cells taken from areas adjacent to tumors expressed pRb positive nuclei. These data suggest that alterations in the expression of the Rb protein may arise early in the development of some lung cancers.

Patients with Rb-positive carcinomas tend to have a somewhat better prognosis but, in most studies, the difference is not significant. However, patients with adenocarcinoma whose tumors are both pRb negative and either p53 or ras positive exhibit a decrease in 5-year survival. A similar relationship does not occur in squamous cell carcinoma. pRb negative tumors have been reported to be more likely to exhibit resistant to doxorubicin than Rb-positive carcinomas.

Thrombomodulin [142–147]

Thrombomodulin is a transmembrane glycoprotein. Through its accelerated activation of protein C (which in turn acts as an anticoagulant by binding protein S and thrombin), synthesis of TM is one of several mechanisms important in reducing clot formation on the surface of endothelial cells. The cellular localization of thrombomodulin is the cell surface.

Aggregation of host platelets by circulating tumor cells appears to play an important role in the metastatic process. Thrombomodulin plays an important role in the activation of the anticoagulant protein C by thrombin and is an important modulator of intravascular coagulation. In addition to its expression in normal squamous epithelium, expression of thrombomodulin also occurs in squamous metaplasia, carcinoma in situ, and invasive squamous cell carcinomas. Although present in 74% of primary squamous cell carcinomas, only 44% of metastatic lesions stained for thrombomodulin. These data suggest that, with progression, there is a decrease in thrombomodulin expression. Higher levels of expression tend to occur in well and moderately differentiated tumors when compared to poorly differentiated tumors.

Patients with thrombomodulin-negative squamous cell carcinoma tend to have a worse prognosis. Eighteen percent of patients with thrombomodulin-negative have a five-year survival as compared to 60% in cases where the tumors stained positive for the protein. Progression to metastatic disease was also more common in thrombomodulin-negative tumors (69% vs. 37%) and there was a greater tendency for these tumors to develop at extrathorasic sites. Thus, loss of thrombomodulin expression appears to be prognostic in cases of squamous cell carcinoma. The observation that changes in thrombomodulin expression occur in later stages of NSCLC and that the protein is expressed by normal bronchial epithelial cells would tend to limit its utility as a marker for early detection. However, since a majority of mesotheliomas and only a small percentage of adenocarcinomas express thrombomodulin, the marker has potential utility in discriminating between these two tumor types.

E-cadherin & N-cadherin [148–151]

E-cadherin is a transmembrane Ca2+ dependent cell adhesion molecule. It plays an important role in the growth and development of cells via the mechanisms of control of tissue architecture and the maintenance of tissue integrity. E-cadherin contributes to intercellular adhesion of epithelial cells, the establishment of epithelial polarization, glandular differentiation, and stratification. Down-regulation of E-cadherin expression has been observed in a number of carcinomas and is usually associated with advanced stage and progression. The cellular localization of E-cadherin is the cell surface.

E-cadherin is a calcium-dependent epithelial cell adhesion molecule. A decrease in E-cadherin expression has been associated with tumor dedifferentiation and metastasis and decreased survival. Reduced expression has been observed in moderately and poorly differentiated squamous cell carcinoma and in SCLC. There was no change in E-cadherin expression in adenocarcinoma. Furthermore, while adenocarcinomas express E-cadherin theses tumors fail to express N-cadherin which is in contrast to mesotheliomas that express N-cadherin but not E-cadherin. Thus, these markers can be used to discriminate between adenocarcinoma and mesothelioma.

Expression of E-cadherin can also be used to assess the prognosis of patients with squamous cell carcinoma. Whereas 60% of patients with tumors expressing E-cadherin survived three-year survival, only 36% of patients exhibiting a reduction in expression survived 3 years.

MAGE-1 and MAGE-3 [152–156]

Melanoma Antigen-1 (MAGE-1) and Melanoma Antigen-3 (MAGE-3) are members of a family of genes that are normally silent in normal tissues but when expressed in malignant neoplasms are recognized by autologous, tumor-directed and specific cytotoxic T cells (CTL's). The cellular localization of MAGE-1 and MAGE-3 is cytoplasmic.

MAGE-1, MAGE-3 and MAGE 4 gene products are tumor-associated antigens that are recognized by cytotoxic T lymphocytes. As such, they could have utility as targets for immunotherapy in NSCLC. MAGE proteins are also expressed by some SCLCs but not by normal cells. While the frequency of MAGE expression falls below the level necessary for use as a detection marker, differences in the pattern of expression between histologic types suggest that MAGE expression may have utility as differentiation markers. This utility is also supported by the observation that, in 50% of squamous cell carcinoma greater than 90% of tumor cells showed evidence of MAGE-3 overexpression with 30% to tumors exhibiting overexpression in at least 50% of cells.

Nucleolar Protein (p120) [157]

p120 (proliferation-associated nucleolar antigen) is found in the cells of nucleoli of rapidly proliferating cells during early G1 phase. The cellular localization of p120 is nuclear.

Nucleolar protein p120 is a proliferation-associated protein whose function has yet to be elucidated. Strong staining has been detected in tumor tissue but not in macrophages or normal tissue. Overexpression of p120 was more common in squamous cell carcinoma that in adenocarcinoma or large cell carcinoma raising the possibility that this marker may have utility in discriminating between tumor types.

Pulmonary Surfactants [83,158–166]

Pulmonary surfactants are a phospholipid-rich mixture that functions to reduce the surface tension at the alveolar-liquid interface, thus providing the alveolar stability necessary for ventilation. Surfactant proteins appear to be expressed exclusively in the airway and are produced by alveolar type II cells. In the non-neoplastic lung, pro-surfactant-B immunoreactivity is detected in normal and hyperplastic alveolar type II cells and some non-ciliated bronchiolar epithelial cells. Sixty percent of adenocarcinomas contained strong cytoplasmic immunoreactivity with 10–50% of tumor cells exhibiting staining the majority of cases. Squamous cell carcinoma and large cell carcinoma failed to stain for pro-surfactant-B.

Surfactant Apoprotein B (SP-B) is one in four hydrophobic proteins that make up the pulmonary surfactant, which is a phospholipid and protein complex secreted by type II alveolar cells. Squamous cell and large cell carcinomas of the lung and nonpulmonary adenocarcinomas do not express SP-B. The cellular localization of SP-B is cytoplasmic.

SP-A is a pulmonary surfactant protein that plays an essential role in keeping alveoli from collapsing at the end of expiration. SP-A is a unique differentiation marker of pulmonary alveolar epithelial cells (type II pneumocytes); the antigen is preserved even in the neoplastic state. The cellular localization of SP-A is cytoplasmic.

Pulmonary surfactant A appears to be specific for non-mucinous bronchoiolo-alveolar carcinoma with 100% staining as compared to none of the of mucinous type. Pulmonary surfactants potentially have utility in discriminating lung cancer from other cancers metastasized to lung. In addition to tumor cells, non-neoplastic pheumocytes also stain for pulmonary surfactant A. As with pulmonary surfactant B staining for pulmonary surfactant A is relatively common in adenocarcinoma but not in other forms of NSCLC or in SCLC. Mesothelioma also fails to express pulmonary surfactant A leading to the suggestion that pulmonary surfactant A may have utility in the discrimination between adenocarcinoma and mesothelioma.

Ki-67

Ki-67 is a nuclear protein that is expressed in proliferating normal and neoplastic cells and is down-regulated in quiescent cells. It is present in G1, S, G2, and M phases of the cell cycle, but is absent in Go phase. Commonly used as a marker of proliferation. The cellular localization of Ki-67 is nuclear.

TABLE 5

| Marker | Squamous Cell Carcinoma | Adenocarcinoma | Large Cell Carcinoma | Small Cell Carcinoma | Mesothelioma |
|---|---|---|---|---|---|
| Glut1 | 100.0+ | 64.5 | 80.5 | 64.0 | NDA* |
| Glut3 | 17.5 | 16.0 | 39.5 | 9.0 | NDA* |
| HERA | 100.0 | 100.0 | 100.0 | NDA | 4.5 |
| Basic FGF | 83.0 | 48.7 | 50.0 | 100.0 | NDA |
| Telomerase | 82.3 | 86.3 | 93.0 | 66.7 | NDA |
| PCNA | 80.0 | 69.8 | 87.7 | 51.0 | NDA |
| CD44v6 | 79.3 | 34.8 | 44.2 | 0.0 | NDA |
| Cyclin A | 79.0 | 68.0 | 83.5 | 97.0 | NDA |
| Cyclin D1 | 42.7 | 36.0 | 62.0 | 90.0 | NDA |
| Hepatocyte Growth Factor/Scatter Factor | 75.5 | 78.3 | 100.0 | NDA | 100.0 |
| MUC-1 | 55.5 | 90.0 | 100.0 | 100 | NDA |
| TTF-1 | 38.0 | 76.0 | NDA | 83.0 | NDA |
| VEGF | 61.8 | 68.3 | 100.0 | 43.5 | NDA |
| EGF Receptor | 63.1 | 45.3 | 96.0 | Frequently | NDA |
| nm23 | 68.0 | 52.6 | 83.5 | 73.5 | NDA |
| Bcl-2 | 45.5 | 43.3 | 42.5 | 92.0 | NDA |
| Loss of pRb Expression | 20.1 | 25.8 | 35.4 | 85.3 | NDA |
| Thrombomodulin | 66.8 | 12.2 | 4.0 | 0.0 | 81.0 |
| E-cadherin | 69.0 | 85.0 | NDA | 100.0 | 0.0 |
| N-cadherin | NDA | 4.0 | NDA | NDA | 94.0 |
| MAGE 1 | 45.0 | 35.0 | NDA | 16.5 | NDA |
| MAGE 3 | 72.0 | 33.3 | NDA | 33.5 | NDA |
| MAGE 4 | 45.5 | 11.0 | NDA | 50.0 | NDA |
| Nucleolar Protein (p120) | 68.0 | 35.0 | 30.0 | NDA | NDA |
| Pulmonary Surfactant B | 0.0 | 61.5 | 0.0 | NDA | NDA |
| Pulmonary Surfactant A | 12.0 | 52.9 | 17.5 | 20 | 0.0 |

+percent of tumors exhibiting a change in marker expression
*No Data Available a. Obtaining a Library of Marker of a Suitable Size Preliminary pruning steps were required in order to obtain a suitable size library of markers that were correlated with lung cancer. More than a hundred markers correlated to lung cancer are known in the literature. A partial listing of candidate probes identified in the literature and evaluated for potential inclusion in panels tests include antibodies to: bax, Bcl-2, c-MET (HGFr), CD44S, CD44v4, CD44v5, CD44v6, cdk2 kinase, CEA (carcino-embryonic antigen), Cyclin A, Cyclin D1 (bcl-1), E-cadherin, EGFR, ER-related (p29), erbB-1, erbB-2, FGF-2 (bFGF), FOS, Glut-1, Glut-2, Glut-3, Glut-4, Glut-5, HERA (MOC-31), HPV-16, HPV-18, HPV-31, HPV-33, HPV-51, integrin VLA2, integrin VLA3, integrin VLA6, JUN, keratin, keratin 7, keratin 8, keratin 10, keratin 13, keratin 14, keratin 16, keratin 17, keratin 18, keratin 19, A-type lamins (A; C), B-type lamins (B1; B2), MAGE-1, MAGE-3, MAGE-4, melanoma-associated antigen clone NKI/C3, mdm2, mib-1 (Ki-67), mucin 1 (MUC-1), mucin 2 (MUC-2), mucin 3 (MUC-3), mucin 4 (MUC-4), MYC, N-cadherin, NCAM (neural cell adhesion molecule), nm23, p120, p16, p21, p27, p53, P-cadherin, PCNA, Retinoblastoma, SP-A, SP-B, Telomerase, Thrombomodulin, Thyroid Transcription Factor 1, VEGF, vimentin, and waf1. The initial list of markers was pruned by initially assessing, from the literature, the apparent effectiveness of the probes in detecting early stage cancer cells, discriminating between cells of differing cancer states, and localizing the label to the target cancer cells. This list of markers was further pruned by removing markers whose utilization would be difficult to reduce to practice because they are difficult to produce or obtain, have unsuitable detection technology requirements or poor reproducibility of reported results. After all of the pruning steps were complete, a library of 27 markers was obtained.

b. Optimizing Protocols and Obtaining Gold Standard Lung Cancer Samples

Preliminary preparation steps were also required prior to obtaining the panels. The probes containing appropriate labels were available from commercial vendors. The protocols of the probes were analyzed for optimum objective quantitative detection. For example, it was determined that the concentration of PCNA was too low. Originally, PCNA was diluted 1:4000 in S809 buffer. A second dilution was made, which was 1:3200 in S809. The optimized protocols for each marker is shown in below. It is noted that the second column is labeled "Antibody Name". Except for MOC-31, the probes in this list are listed by the marker name because many of the vendors refer to the antibody by the name of the marker. It is noted that an alternative way these reagents might be listed is, for example, anti-VEGF, anti-Thrombomodulin, anti-CD44v6, etc.

Gold standard tissue specimens were obtained from UCLA. Tissue specimens were received from two sources. Cases had been diagnosed using standard procedures including review of hematoxylin and eosin (H&E)-stained slides and the clinical history. Specimen slides were coded and labeled with arbitrary numbers to blind the study pathologists to the historical diagnosis and antibody marker and to protect patient confidentiality.

Specimen slides with tissue sections from cancerous and non cancerous (control) tissues were used. A total of 175 separate cases were analyzed. Within this set, the following diagnoses, located in Table 6 were present with the following frequencies:

TABLE 6

| | Diagnosis | Number of occurrences |
|---|---|---|
| Cancer | Adenocarcinoma | 25 |
| | Large Cell Carcinoma | 18 |
| | Mesothelioma | 26 |
| | Small Cell Lung Cancer | 20 |
| | Squamous Cell Carcinoma | 24 |
| Control | Emphysema | 34 |
| | Granulomatous Disease | 3 |
| | Interstitial Lung Disease | 25 | c. Determination of the Level of Expression of the Panel of Molecular Markers

Sufficient specimen slides were prepared for each case so that only one probe was tested per slide. In general, a microscope slide is prepared which contains the cytologic sample contacted with one or more labeled probes that are directed at particular molecular markers. Independently, each study pathologists examined an H&E-stained slide to make a diagnosis for each case, and then examined each probe-reacted and immunochemically-stained slide to assess the level of probe binding, recording the results on a standardized data form.

In greater detail, the immunohistochemical staining was performed on formalin fixed, paraffin embedded (FFPE) tissue. Tissue sections were cut at 4 microns thick on poly-L-Lysine coated slides and dried at room temperature overnight. De-paraffinization and rehydration of the tissue sections were performed as follows: To completely remove all of the embedding medium from the specimen the slides were incubated in two consecutive Xylene-substitute (Histoclear) baths for five minutes each. All liquid was tapped off the slides before incubation in two consecutive baths of 100% reagent grade alcohol for three minutes each. Once again all excess liquid was tapped off the slides before being incubated in two final baths of 95% reagent grade alcohol for three minutes each. After the last bath of 95% the slides were rinsed in tap water and held in wash buffer (Tris-buffered saline wash buffer containing 0.05% Tween 20 corresponding to a 1:10 dilution of DAKO Autostainer Wash buffer, code S3306). Table 7, below, presents a complete list of the reagents used in this study along with corresponding product code numbers. Detection systems used in the study were DAKO EnVision+HRP mouse (code K4007) or rabbit (code K4003) and LSAB+ HRP (code K0690). The protocols for immunoassaying were followed according to the package inserts. The kits contained liquid two component DAB+ substrate chromogen (code K3468).

TABLE 7

| Reagents used in the Study | |
|---|---|
| Reagents | Code # |
| National Diagnostics HistoClear | HS-200 |
| Mallinckrodt Reagent Alchohol Absolute | 7019-10 |
| DAKO Antibody Diluent | S809 |

TABLE 7-continued

| Reagents used in the Study | |
|---|---|
| DAKO Background Reducing Antibody Diluent | S3022 |
| DAKO Autostainer Buffer 10X | S3306 |
| DAKO Target Retrieval Solution | S1700 |
| DAKO Hi pH Target Retrieval Solution | S3307 |
| DAKO Proteinase K | S3020 |
| Rite Aid Hydrogen Peroxide 3% | None |
| DAKO Protein Block Serum Free | X0909 |
| DAKO Goat Serum | X0501 |
| DAKO Swine Serum | X0901 |
| DAKO EnVision+ Mouse | K4007 |
| DAKO EnVision+ Rabbit | K4003 |
| DAKO LSAB+ | K0690 |
| DAKO DAB+ | K3468 |
| DAKO Hematoxylin | S3302 |
| Dakomount Mounting Media | S3025 |
| Instruments | Serial Numbers |
| DAKO Autostainers | 3400-6613-03 |
| | 3400-6142R-03 |
| Autostainer IHC Software Version V3.0.2 | |

Pretreatments were critical in optimizing these antibodies on lung tissue. For antibodies requiring enzyme digestion, DAKO Proteinase K (code S3020) was used for 5 minutes at room temperature. Antibodies requiring heat induced target retrieval received pretreatment using either DAKO Target Retrieval Solution (code S1700) or DAKO High pH Target Retrieval Solution (code S3307). Tissues were placed in a pre-heated Target Retrieval Solution and incubated in a 95° C. water bath for 20 or 40 minutes depending on the specific protocol. Tissue sections were then allowed to cool at room temperature for an additional 20 minutes.

After de-paraffinization, rehydration and tissue pretreatment, all specimens were incubated in a solution of 3% hydrogen peroxide to quench endogenous peroxidase activity. Blocking reagents were used specifically for the two antibodies FGF and Telomerase in order to minimize non-specific background.

As shown in Table 8, below, tissue specimens were incubated for a specified length of time with 200 micro liters of the optimally diluted primary antibody. It is noted that the numbering of the markers/antibodies in Table 8 is consistent with the numbering of the antibody probes and markers throughout this document. Slides were then washed in DAKO 1× Autostainer Buffer (code S3306). Depending on the antibody, the correct detection system applied. The steps and total incubation times for the DAKO EnVision+ HRP and LSAB+ HRP detection systems are shown in Table 9, below. The color reaction is developed using 3,3'-aminobenzidine (DAB) resulting in a brown color precipitate at the site of the reaction.

TABLE 8

Antibodies for Lung Panel

| # | Antibody to Marker: | Pretreatment | Block | Dilution | Primary Inc | Detection Sys | Clone | Vendor | Code# |
|---|---|---|---|---|---|---|---|---|---|
| 1 | VEGF | Hi pH TRS 20 min S3307 | None | 1:15 in S809 | 30 minutes | EnV + mouse | JH121 | NeoMarkers | MS-350-P |
| 2 | Thrombomodulin | None | None | 1:100 in S809 | 30 minutes | EnV + mouse | 1009 | DAKO | M0617 |
| 3 | CD44v6 | TRS 20 min S1700 | None | RTU | 30 minutes | EnV + mouse | VFF-7 | NeoMarkers | MS-1093-R7 |
| 4 | SP-A | None | None | 1:200 in S809 | 30 minutes | EnV + mouse | PE10 | DAKO | M4501 |
| 5 | Retinoblastoma | TRS 40 min S1700 | None | 1:25 in S809 | 30 minutes | EnV + mouse | Rb1 | DAKO | M7131 |
| 6 | E-Cadherin | TRS 20 min S1700 | None | 1:100 in S809 | 30 minutes | EnV + mouse | NCH-38 | DAKO | M3612 |
| 7 | Cyclin A | TRS 20 min S1700 | None | 1:25 in S809 | 30 minutes | EnV + mouse | 6E6 | Novocastra | NCL 117205 |
| 8 | nm23 | Hi pH TRS 20 min S3307 | None | 1:50 in S809 | 30 minutes | EnV + rabbit | Polyclonal | DAKO | A0096 |
| 9 | Telomerase | TRS 20 min S1700 | Prot Block X0909, 30 min w/5% goat serum X0501 | 1:400 in S809 | Overnight | EnV + rabbit | Polyclonal | Alpha Diagnostic | EST21-A |
| 10 | Ki-67 | TRS 40 min S1700 | None | 1:200 in S809 | 30 minutes | EnV + mouse | IVAK-2 | DAKO | M7240 |
| 11 | Cyclin D1 | Hi pH TRS 20 min S3307 | None | 1:200 in S3022 | 30 minutes | EnV + mouse | DCS-6 | DAKO | M7155 |
| 12 | PCNA Dilution 1 | TRS 20 min S1700 | None | 1:4000 in S809 | 30 minutes | EnV + mouse | PC10 | DAKO | M0879 |
| 13 | MAGE-1 | Hi pH TRS 20 min S3307 | None | 1:250 in S809 | 30 minutes | EnV + mouse | MA454 | NeoMarkers | MS 1067 |
| 14 | Mucin 1 | TRS 20 min S1700 | None | 1:40 in S809 | 30 minutes | EnV + mouse | VU4H5 | Santa Cruz Biotech | Sc-7313 |
| 15 | SP-B | TRS 20 min S1700 | None | 1:100 in S809 | 30 minutes | EnV + mouse | SPB02 | NeoMarkers | MS-1300-P1 |
| 16 | HERA | TRS 40 min S1700 | None | 1:50 in S809 | 30 minutes | EnV + mouse | MOC-31 | DAKO | M3525 |
| 17 | FGF-2 | None | Prot Block X0909, 30 min w/5% swine serum X0901 | 1:50 in S809 | Overnight | EnV + mouse | bFM-2 | Upstate Biotech | #05-118 |
| 18 | C-Met | Incomplete | None | Incomplete | Incomplete | EnV + mouse | 8F11 | Novocastra | 118406 |
| 19 | TTF-1 | TRS 40 min S1700 | None | 1:25 in S809 | 30 minutes | EnV + mouse | 8G7G3/1 | DAKO | M3575 |
| 20 | Bcl-2 | Hi pH TRS 20 min S3307 | None | 1:75 in S809 | 30 minutes | EnV + mouse | 124 | DAKO | M0887 |
| 21 | p120 | TRS 20 min S1700 | None | 1:10 in S809 | 30 minutes | EnV + mouse | FB-2 | Biogenex | MU196-UC |
| 22 | N-Cadherin | TRS 40 min S1700 | None | 1:75 in S809 | 30 minutes | EnV + mouse | 6G4 & 6G11 | DAKO | N/A |
| 23 | EGFR | Prot K 1:25 for 5 min | None | 1:1500 in S809 | 30 minutes | EnV + mouse | 2-18C9 | DAKO | K1492 |
| 24 | Glut 1 | TRS 40 min S1700 | None | 1:200 in S809 | 30 minutes | LSAB+ | Polyclonal | Santa Cruz Biotech | SC 1605 |
| 25 | ER-related (p29) | TRS 40 min S1700 | None | 1:200 in S809 | 30 minutes | EnV + mouse | G3.1 | Biogenex | MU171-UC |
| 26 | Mage 3 | TRS 40 min S1700 | None | 1:20 in S809 | 30 minutes | EnV + mouse | 57B | G. Spagnoli | N/A |
| 27 | Glut 3 | TRS 20 min S1700 | None | 1:80 in S809 | 30 minutes | LSAB+ | Polyclonal | Santa Cruz Biotech | SC 7581 |
| 28 | PCNA Dilution 2 | TRS 20 min S1700 | None | 1:3200 in S809 | 30 minutes | EnV + mouse | PC10 | DAKO | M0879 |

TABLE 9

Detection Systems Used in the Study

Steps

1  Deparafinization and rehydration 2 baths of Histoclear for 5 mins each
   2 baths of 100% alchohol for 3 mins each
   2 baths of 95% alchohol for 3 mins each
   Water Rinse
2  Pretreatments TRS 40 or 20 mins
   High pH TRS 20 mins
   Proteinase K for 5 mins
   Water Rinse
3  Peroxidase block Peroxide bath for 5 mins
   Water Rinse
   Buffer for 5 mins
   Protein Block for 30 mins after H2O2 Block
4  Primary Ab 30 mins or Overnight at room temp
5  Detection System EnV + Systems                Labelled Polymer OR LSAB+ System    Secondary Reagent
                                30 mins                             15 mins Secondary Ab link
                                                                    Tertiary Reagent
                                                                    15 mins SA-HRP
6  Chromogen Chromogen                           Chromogen
                                10 mins DAB+                        5 mins DAB+

Following immunostaining all slides were incubated in DAKO Hematoxylin (code S3302) for 3 minutes and coverslipped using DAKOMount Mounting Media (S3025). All protocols were run on DAKO Autostainers (serial #'s 3400-6612-03 & 3400-6142R-03) using the IHC software version 3.0.2.

Immunostaining was viewed under a light microscope to determine that controls were correctly stained and tissues were intact. Slides were labeled, boxed and sent to designated pathologists for results interpretation. Trained pathologists identified the type of cancer or other lesion seen in the samples. Trained pathologists assessed the sensitivity to the marker probe by estimating the staining density and proportion of cells stained. These scores were entered in a data sheet for that patient. The pathologists were blinded to the original diagnosis and antibody marker used in the immunostaining. Each slide was read by at least two pathologists and results recorded on a data collection form. To provide additional integrity to the process, the method is repeated with a second or third pathologist. The scores obtained can then be matched to identify data entry errors. The additional data also facilitates a better classifier design.

For each case, up to 27 slides were analyzed, each stained for a marker coded with numbers 1 through to 17, 19 through to 28. Staining for marker 18 (C-MET) could not be optimized and the marker/probe was therefore not used. Pathologist 1 scored slides from all 175 cases. Pathologist 2 scored slides from 99 of the cases. Pathologist 3 scored slides from 80 of the cases.

Table 10 below shows how many cases of each diagnosis each pathologist scored slides from:

TABLE 10

|  | Diagnosis | Pathologist 1 | Pathologist 2 | Pathologist 3 |
|---|---|---|---|---|
| Cancer | Adenocarcinoma | 25 | 12 | 14 |
|  | Large Cell Carcinoma | 18 | 9 | 9 |
|  | Mesothelioma | 26 | 14 | 8 |
|  | Small Cell Lung Cancer | 20 | 12 | 6 |
|  | Squamous Cell Carcinoma | 24 | 13 | 11 |
| Control | Emphysema | 34 | 23 | 13 |
|  | Granulomatous Disease | 3 | 3 | 2 |
|  | Interstitial Lung Disease | 25 | 13 | 17 |

For the purposes of some selected statistical analysis techniques, it was necessary to consider only those cases that had scores for all 27 slides present. Table 11 below shows how many cases of each diagnosis were complete in terms of having scores from all 27 slides.

TABLE 11

|  | Diagnosis | Pathologist 1 | Pathologist 2 | Pathologist 3 |
|---|---|---|---|---|
| Cancer | Adenocarcinoma | 14 | 10 | 8 |
|  | Large Cell Carcinoma | 12 | 9 | 3 |
|  | Mesothelioma | 17 | 13 | 3 |
|  | Small Cell Lung Cancer | 7 | 9 | 1 |
|  | Squamous Cell Carcinoma | 12 | 13 | 4 |
| Control | Emphysema | 32 | 21 | 1 |
|  | Granulomatous Disease | 2 | 1 | 0 |
|  | Interstitial Lung Disease | 23 | 7 | 3 |

From this table, it can be calculated that each pathologist scored the following total number of complete cases. Pathologist 1 scored all 27 slides for 119 of the cases Pathologist 2 scored all 27 slides for 83 of the cases. Pathologist 3 scored all 27 slides for 23 of the cases.

The total number of cancer data points is 172. This comprises 113 data points from Pathologist 1 and 60 data points from Pathologist 2. The total number of control data points is 101. This comprises 62 data points from Pathologist 1 and 39 data points from Pathologist 2.

FIG. 3 shows a comparisons between H-scores for probes 7 and 15 in control tissue and in cancerous tissue. The x-axis shows the H-scores while the y-axis shows the percent of cases with that particular H-score. The difference in H-scores is apparent.

For each patient the scores were entered electronically into a Pathology Review Form which consolidates the scores into a data base showing the patient identifier together with diagnosis, proportion of cells stained, and staining density. The proportions and density were consolidated into a single "H-Score" obtained by grading the intensity as: none=0, weak=1, moderate=2, intense=3, and the percentage cells as: 0–5%=0, 6–25%=1, 26–50%=2, 51–75%=3, >75%=4, and then multiplying the two grades together. For example, 50% weakly stained plus 50% moderate stained would score 10=2×2+2×3. This is the standard scoring system throughout the analysis, except for the section 3(f), below, titled "Effect of Using other (non-H-score) objective scoring parameters", which investigates alternative scoring systems.

Standard classification procedures were used to find the best combination of probes. Typically these use a search procedure such as the "Branch and Bound Algorithm" to find a hierarchy of the best features, ranked according to a test of discriminating power, and truncated according to a test of significance. This process also defines the decision rule or rules for best classification.

The performance of a classifier designed with these features can be estimated from the data used to design the classifier. The straightforward application of all the design data to the classifier gives a very unsound estimate of performance.

The analysis of the data collected in the present example provide the optimum selection of probes which provided the best separation of classes. Therefore, panels were obtained that only needed a few probes to perform the analysis. However the data showed that near-optimum performance could be obtained with other combinations of probes. Hence, the invention is flexible in being adaptable to the availability of probes where cost or supply problems may not allow the very best combination. In some cases, the invention can simply be applied to the available features to find an alternative combination. In other cases, the algorithm may be used to select features which allows cost weightings to be included in the selection process to arrive at a low cost solution.

The design of data collection and analysis experiment was chosen to avoid biases through the well established double blind procedures where data collection and data analysis were done independently.

In the first case the pathologists reviewed slides with conventional staining to allow a diagnosis to be made. This diagnosis was entered on the Pathology Review form. The pathologists were then presented, in random order, with slides stained by the marker probes for scoring the percentage of cells stained and the relative intensity of the staining. The slides were numbered to exclude information about the probe from the pathologist. To allow data integrity to be checked two pathologists reviewed all patients.

Data were consolidated into a database that was then reviewed by a team of statisticians. Probes were numbered to render their method of action as unseen during the analysis of their effectiveness.

The first stage of the analysis was to check the integrity of the data by comparing entries for each patient. Where large differences were found, the data entries were checked and any obvious errors were corrected. Unexplained differences were left in the data.

The data were then separately analyzed by four statisticians, using different techniques in recognition of the fact that different statistical methodologies are suited to different types of discriminating information in the data.

The first step in the process of selecting the best probe combination is to divide the data into two sets, one for designing a classifier and one for testing the performance of the classifier. By selecting the design made with the design (train) set, but showing the best performance evaluated on the test set, it can be concluded with confidence that the classifier has generalized to the structure of the data and not adapted to particular cases seen in the training set.

In order to test for reliability the analysis was typically repeated with many randomly selected sets of training data and test data. This approach is generally accepted as giving good estimates of the classifier performance. Where these tests showed inconsistent selections of probes such probe selections were discounted as unreliable.

d. Statistical Analysis and/or Pattern Recognition
1. Introduction to Data Analysis
 a. Input Data
 i. Raw Data For each patient the scores were entered electronically into a Pathology Review Form that consolidates the scores into a database showing the patient identifier together with diagnosis, proportion of cells stained, and staining density.
 ii. Computed Data The efficiency of the score for each probe used in the analysis is computed from the intensity/percentage tables. The proportions and density are consolidated into a single "H-Score" with a simple rule H=proportion stained x (3 if intense+2 if moderate+1 if weakly stained). This is the feature value associated with that probe.
 iii. Alternative Computed Data Parameters The H-score described above was heuristically derived, a simple analysis to find a better way of combining percentages and intensity failed to show a significant improvement over H-score (Section 3(f), titled "Effect of Using other (non-H-score) objective scoring parameters"). A larger data base may allow the extraction of a better rule in future.

iv. User Supplied Weighting Criteria Per Marker

The invention is flexible in being adaptable to the availability of features where cost or supply problems may not allow the very best combination. For example, the invention can simply be applied to the available features to find and alternative combination. Alternatively, the algorithm used to select features allows cost weightings to be included in the selection process to arrive at a minimum cost solution. Marker performance estimates are shown for combinations selected from all the markers collected or only those from one supplier. It is also shown how the C4.5 package can be used to down weight certain probes, say on the basis of their high cost. These probe combinations do not perform as well as the optimum combination, but the performance might be acceptable in circumstances where cost is a significant factor.

V. User Supplied Weighting Criteria Per Class

Some of the methods used allow weightings to be applied to the classes. This is available in C4.5 where the tree design can optimize the cost. Also the Discriminant Function method gives a single parameter output which can be used to give a desired false positive or false negative probability. A plot of these parameters for different threshold settings is known as the Receiver Operating Curve.

vi. Detection Panels—Assumptions

A low probability of a false negatives was assumed to be desirable for the cancer detection process (to avoid positive patients being missed at the cost of an increased number of false positives who would require re-screening). It was also assumed that the cancer discrimination process would require a lower false positive score (to minimize patients receiving the wrong treatment).

It was assumed that detection panels requiring 6 or more probes to achieve an acceptable performance would not be cost effective. It was also assumed that a detection panel with a false negative error rate of more than 5% would not be acceptable. Panels falling outside this box are not accepted. This assumption acknowledges that cytometric panels are likely to have a worse performance than the histology based panels analyzed here. The ultimate aim will be a cytometric panel which performs better than 20% error rate, this being approximately the performance of cervical PAP smear screeners.

vii. Discrimination Panels—Assumptions

It was assumed that panels requiring 6 or more probes are not cost effective and it was assumed that an error rate of better than 20% is required. Panels falling outside this box were not accepted.

b. Output Data

Outputs provided by the present analysis included:

Confusion Matrices, showing how data from the test set was classified as either true positive, false positive, true negative or false negative. These may be shown as actual counts or as percentages. Confusion matrices are discussed in section 2(d) titled "Performance Metrics". A confusion matrix shows how data from a test set was classifiefd as either true positive, false positive, true negative or false negative. An exemplary confusion matrix, obtained from data analyzed by decision trees, is shown below in table 12 for simultaneous discrmination of adenocarcinoma, squamous cell carcinoma, large cell carcinoma, mesothelioma and small cell carcinoma

TABLE 12

|  | Adeno | Squamous | Large Cell | Mesothelioma | Small Cell |
| --- | --- | --- | --- | --- | --- |
| Adeno | 67.74% | 6.45% | 19.40% | 0.00% | 6.45% |
| Squamous Cell | 2.94% | 76.47% | 11.67% | 0.00% | 8.82% |
| Large Cell | 28.00% | 8.00% | 44.00% | 8.00% | 12.00% |
| Mesothelioma | 0.00% | 25.64% | 51.28% | 89.74% | 2.56% |
| Small Cell | 0.00% | 3.85% | 23.08% | 3.85% | 69.23% |

Error Rates, summarizing data in the confusion matrix as the sum of all false classifications divided by the total number of classifications made expressed as a percentage Receiver Operating Characteristic (ROC) curves show the estimated percentage (or per unit probability) of false positive and false negative scores for different threshold levels in the classifier. An indifferent classifier, unable to discriminate better than random choice would present a ROC curve with equal true and false readings. The area under this curve would be 50% (0.5 probability).

Area Under the Curve (AUC) is often used as an overall estimate of classifier performance and most standard discriminant function packages provide this AUC figure. A perfect classifier would have 100% Area Under the Curve, and a useless classifier would have an AUC near 50% (0.5).

Sensitivity and specificity (can be derived from the confusion matrix). See section 2(d)(iii) titled "Sensitivity and Specificity".

Figure 4:
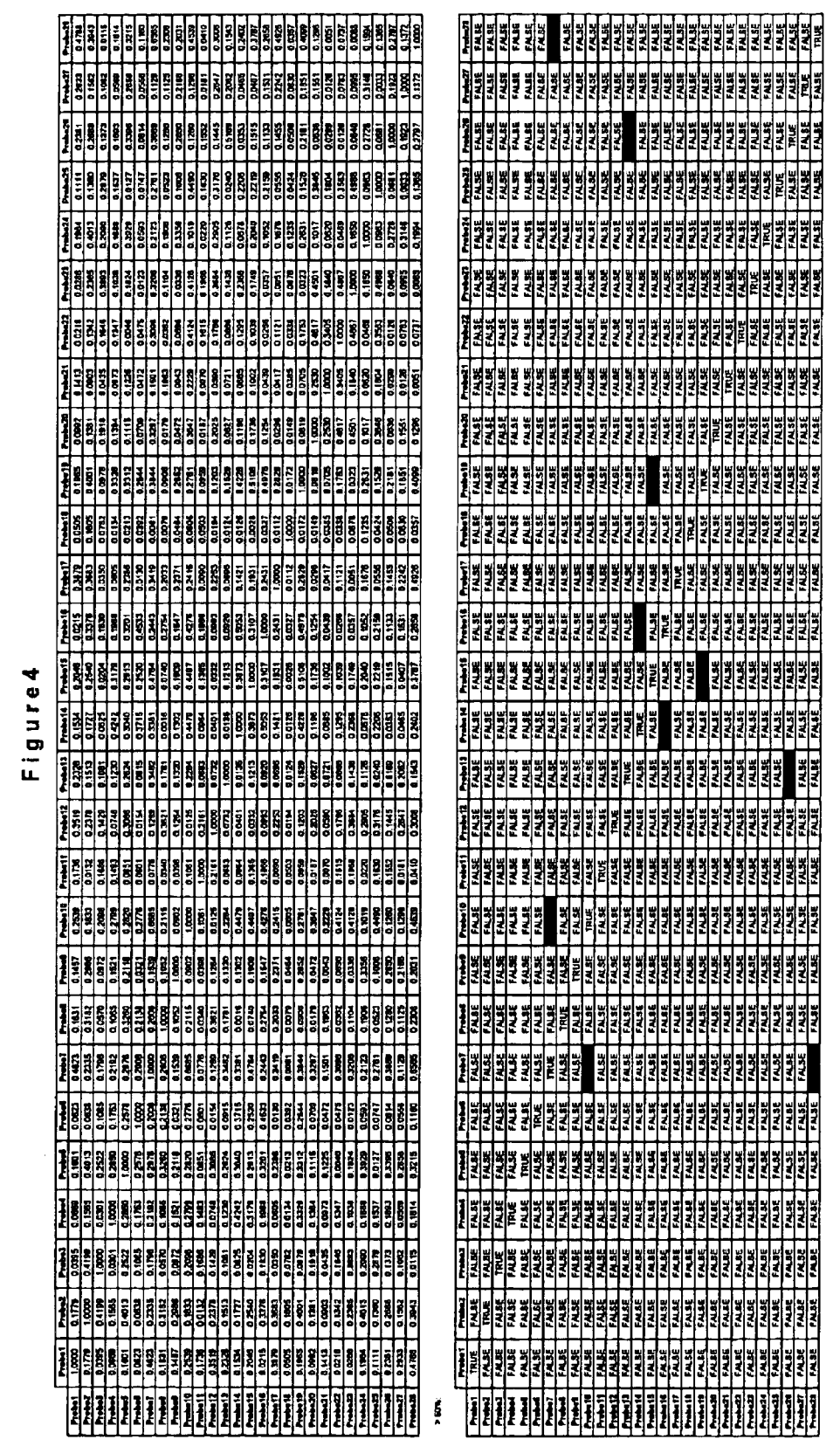

Marker correlation matrices. See FIG. 4.

i. Detection Panels: Composition

These panels are trained on data divided into two classes, patients with any of the five cancers and patients with none of the cancers. Not all probes were present for all patients. Where one or more probes were missing for a particular analysis these cases were excised from the data. Hence, where analysis was undertaken on reduced numbers of probes the data set might include slightly more cases.

The number of probes included in the analysis was 27. Although in many cases a false probe was added where the data entered for that probe was from a random number generator set to generate numbers uniformly between zero and 12. This false probe was included in much of the early analysis to ensure integrity in the probe selection process. This false probe was also used in one approach to progressively eliminate probes from the analysis. Probes that contributed less information than the false probe could be readily identified and excluded from the selection process. Early elimination of such probes speeds the analysis and renders the analysis less vulnerable to variations in results (noise) caused by these probes.

ii. Detection Panel Performance

As outputs from this study, the probe combinations selected by the different methodologies and their performance estimates in terms of the confusion matrix, % error rate, and AUC are reported.

iii. Detection Panels—Alternative Compositions

Detection panels were also selected from reduced sets of probes. In one set of panels, performance measures of panels weighted for commercially preferred markers were obtained. The performances obtained when the best probe was removed from the analysis to find a new combination of discriminating probes was also analyzed. The performance of a single probe acting on its own was found to be very high (probe 7). However, as shown below in the performance diagrams, Table 13, evaluated using linear discriminant analysis, the performance was improved as more markers were added. The best subsets of probes were determined using best subsets logistic regression. The improvement is statistically significant.

TABLE 13

|  |  | Cancer | Control |
|---|---|---|---|
| Probe 7 | Cancer | 87.93% | 12.07% |
|  | Control | 0.00% | 100.00% |
| Probes 7 and 16 | Cancer | 93.10% | 6.90% |
|  | Control | 1.16% | 98.84% |
| Probes 7, 15 and 16 | Cancer | 90.52% | 9.48% |
|  | Control | 1.16% | 98.84% |
| Probes 1, 7, 15, and 16 | Cancer | 90.52% | 9.48% |
|  | Control | 0.00% | 100.00% |
| Probes 1, 4, 7, 15, and 16 | Cancer | 92.24% | 7.76% |
|  | Control | 1.16% | 98.84% |

The best and second best subsets of probes (determined using best subsets logistic regression) and evaluated using logistic regression is shown below. AUC=Area under ROC curve. It is noted that mean AUC is the average from 100 trials on random train and test partitions (70%:30%). The results are shown below, in Table 14.

TABLE 14

| Probes | Mean AUC |
|---|---|
| 7 | 94.28 |
| 28 | 80.14 |
| 7, 16 | 95 |
| 7, 15 | 94.59 |
| 7, 15, 16 | 95.94 |
| 1, 7, 16 | 95.33 |
| 1, 7, 15, 16 | 95.61 |
| 4, 7, 15, 16 | 95.34 |
| 1, 4, 7, 15, 16 | 95.3 |
| 1, 7, 11, 15, 16 | 95.57 | iv. Discrimination Panels—Composition

For this part of the study five classifiers were designed and tested, each designed to detect the presence of one of the cancer from all patients with cancer. The application of this five way pair-wise system allows doubtful cases to appear more than once in the analysis, or not at all. Such cases can be identified and subjected to closer scrutiny, re-testing or alternative testing regimes.

Again the number of probes in the study was 27, with a false probe used in the early stage to reduce the numbers in the analysis v. Discriminant Panels—Performance The performance estimators described above were used to show the performance of the best probe combinations discovered by the different techniques vi. Discriminant Panels—Alternative Composition The analysis was repeated for a probe combination comprising commercially preferred probes. Performance was degraded, but not unusable for several reduced-set classifiers. Below, the best subsets of probes without probe 7, determined using best subsets logistic regression), is shown, as Table 15. The data was evaluated using linear discriminat analysis.

TABLE 15

|  |  | Cancer | Control |
|---|---|---|---|
| Probe 28 | Cancer | 0.706897 | 0.293103 |
|  | Control | 0.093023 | 0.906977 |
| Probes 10 and 28 | Cancer | 0.793103 | 0.206897 |
|  | Control | 0.034884 | 0.965116 |
| Probes 10, 15 and 28 | Cancer | 0.810345 | 0.189655 |
|  | Control | 0.011628 | 0.988372 |
| Probes 1, 10, 15 and 28 | Cancer | 0.827586 | 0.172414 |
|  | Control | 0.011628 | 0.988372 |
| Probes 1, 10, 15, 16 and 28 | Cancer | 0.827586 | 0.172414 |
|  | Control | 0.011628 | 0.988372 |

The best and second best subsets of probes with probe 7 (determined using best subsets logistic regression) and evaluated using logistic regression is shown below. AUC=Area under ROC curve. It is noted that mean AUC is the average from 100 trials on random train and test partitions (70%:30%). The results are shown below, in Table 16.

TABLE 16

| Probes | Mean AUC |
|---|---|
| 28 | 79.36% |
| 10 | 82.28% |
| 10, 28 | 94.21% |
| 15, 28 | 88.68% |
| 10, 15, 28 | 92.90% |
| 1, 10, 28 | 93.59% |
| 1, 10, 15, 28 | 92.99% |
| 8, 1, 15, 28 | 93.20% |
| 1, 10, 15, 16, 28 | 93.13% |
| 1, 8, 10, 15, 28 | 93.57% |

2. Data Analysis Methodology

In this section, the process of gaining an initial understanding of the structure of the data as a guide to interpreting results from the different methodologies used is described.

a. Analysis of Variance i. Pathologist-to-Pathologist Variability and Pooling Pathologist Scores.

(1) t—Test

Two pathologists reviewed each patient's slides in this clinical trial. Pathologist 1 reviewed all patients, Pathologist 2 also reviewed approximately half of this set and Pathologist 3 reviewed the remainder. With two independent estimates of the H-score, the consistency of pathologist performance could be tested.

A readily available statistical tool was used to test the variability between pathologists. This is the paired-sample t-test. This takes the difference between each pair of estimates, averages these and expresses this as a proportion of the overall variances. The t-test then converts this ratio into a probability estimating the likelihood that the two samples sets came from the same population (the P value).

This test was applied to the scores for each marker probe, for all cases reviewed by Pathologist 1 and Pathologist 2, and also for all cases reviewed by Pathologist 1 and Pathologist 3. Since there were 27 tests applied (to cover all probes) a low value of P=0.01 was selected as the "significant threshold". Results, showing the P scores for each probe, and for the two pairs of pathologists, are shown below, in Tables 17, 18,19 and 20. It is clear that Pathologist 1 and Pathologist 2 were more consistent than Pathologist 1 and Pathologist 3.

TABLE 17

| Pathologist 1, Pathologist 2 scores: | | | | | | |
|---|---|---|---|---|---|---|
| X1 | X2 | X3 | X4 | X5 | X6 | X7 |
| 0.5875446 | 0.01051847 | 0.4659704 | 0.4659704 | 0.3772894 | 0.2307273 | 0.01001357 |
| X8 | X9 | X10 | X11 | X12 | X13 | X14 |
| 0.004131056 | 0.7703014 | 0.1640003 | 0.2374452 | 0.9580652 | 0.1587876 | 0.001200265 |
| X15 | X16 | X17 | X18 | X19 | X20 | X21 |
| 0.19742 | 0.3860899 | 0.3829022 | NA | 0.544601 | 0.08873848 | 0.1686243 |
| X22 | X23 | X24 | X25 | X26 | X27 | X28 |
| 0.5428451 | 0.1912477 | 0.4031977 | 0.2477236 | 0.5673386 | 0.9174037 | 0.00339071 |

TABLE 18

| Pathologist 1, Pathologist 2 scores thresholded at 0.01 ($\alpha$ = 1% level of significance): | | | | | | |
|---|---|---|---|---|---|---|
| X1 | X2 | X3 | X4 | X5 | X6 | X7 |
| TRUE | TRUE | TRUE | TRUE | TRUE | TRUE | TRUE |
| X8 | X9 | X10 | X11 | X12 | X13 | X14 |
| FALSE | TRUE | TRUE | TRUE | TRUE | TRUE | FALSE |
| X15 | X16 | X17 | X18 | X19 | X20 | X21 |
| TRUE | TRUE | TRUE | NA | TRUE | TRUE | TRUE |
| X22 | X23 | X24 | X25 | X26 | X27 | X28 |
| TRUE | TRUE | TRUE | TRUE | TRUE | TRUE | FALSE |

TABLE 20

| Pathologist 1, Pathologist 3 scores thresholded at 0.01 ($\alpha$ = 1% level of significance):: | | | | | | |
|---|---|---|---|---|---|---|
| X1 | X2 | X3 | X4 | X5 | X6 | X7 |
| FALSE | TRUE | FALSE | FALSE | TRUE | TRUE | TRUE |
| X8 | X9 | X10 | X11 | X12 | X13 | X14 |
| FALSE | FALSE | FALSE | FALSE | TRUE | TRUE | FALSE |
| X15 | X16 | X17 | X18 | X19 | X20 | X21 |
| FALSE | TRUE | FALSE | FALSE | FALSE | FALSE | TRUE |
| X22 | X23 | X24 | X25 | X26 | X27 | X28 |
| TRUE | FALSE | FALSE | TRUE | TRUE | FALSE | TRUE |

TABLE 19

| Pathologist 2, Pathologist 3 scores: | | | | | | |
|---|---|---|---|---|---|---|
| X1 | X2 | X3 | X4 | X5 | X6 | X7 |
| 3.814506e−09 | 0.0399131 | 0.1954867 | 5.671062e−05 | 0.01856276 | 0.2757166 | 0.2292583 |
| X8 | X9 | X10 | X11 | X12 | X13 | X14 |
| 2.044038e−12 | 0.004166467 | 0.00983267 | 0.003710155 | 0.01461007 | 0.03312421 | 0.0003367823 |
| X15 | X16 | X17 | X18 | X19 | X20 | X21 |
| 0.0005162036 | 0.2276537 | 0.002987705 | | 4.267708e−06 | 0.007287372 | 0.1654067 |
| X22 | X23 | X24 | X25 | X26 | X27 | X28 |
| 0.02400127 | 0.0009497766 | 2.478456e−07 | 0.1591684 | 0.08318303 | 3.122143e−05 | 1 |

Because the H score is subjective it is prone to scale factor differences and noise at marginal cases. So, in spite of the three features which showed statistically different scores between Pathologist 1 and Pathologist 2, this joint data was accepted as representative of a measuring instrument.

Pathologist 1 and Pathologist 2 were combined into a single data set for the analysis process. The results for Pathologist 3 were withheld for independent testing purposes. Such tests using the Pathologist 3 data would be biased towards showing an under-performance because of the significant differences.

The data from Pathologist 1 and Pathologist 2 were combined by considering them as separate cases, with the variability giving a degree of independence between the results for any one case. When testing with such data the performance estimates will be biased towards a more optimistic value. This is because samples coming from the same patient may occur simultaneously in the training a test subsets. This does not however invalidate the processes used to find the best combination of features, it merely biases the estimate of performance.

(2) Analysis of Variance of H-Scores (a) Background

Within each probe, the H-scores may vary due to many reasons. To the extent they vary consistently due to the type of disease this is useful, variation due to which pathologist read the slide is instructive, whereas random variation sets a limit on the detection of the previous two sources of variation.

Analysis of Variance (ANOVA) is a standard technique for splitting up the sources of variation in data and for testing its statistical significance. ANOVA summarizes the total variation of a set of data as a sum of terms which can be attributed to specific sources, or causes, of variation.

ANOVA is available in many statistical packages. The public domain package "R" was chosen ("The R Project for Statistical Computing", http://www.R-project.org/).

(b) Aim

To perform ANOVA analyses on the H-score data from pathologists 1 and 2 and to consider whether this data can be safely merged into a single consistent set for further analysis for the selection of panels.

(c) Methodology

From the database, data was selected from pathologists 1 and 2. Only data which was complete for a given probe was used in the ANOVA for that probe.

The control categories of Emphysema, Granulomatous Disease, and Interstitial Lung Disease were grouped together and called "Normal" giving 6 levels within factor Disease.

Pathologist was coded as a factor with 2 levels (Pathologist 1, Pathologist 2).

An R script was written to perform a standard ANOVA analysis for each probe in turn, using the factors: Disease, Pathologist, and the interaction term Disease:Pathologist. The results are shown in below, in Table 21. "Df" is defined as the degrees of freedom. In a dataset of n observations, knowing n-1 deviations from the mean, the nth is automatically determined. N-1 is the number of degrees of freedom. Sum Sq and mean Sq are measures of variation. F is a test statistic concerning the equality of two variances based on the F distribution. Pr(>F) is the probability used to determine whether or not the variability is statistically significant.

TABLE 21

Analysis of Variance of H-Scores

| | Df | Sum Sq | Mean Sq | F value | Pr(>F) | |
|---|---|---|---|---|---|---|
| Probe1 | | | | | | |
| Disease | 5 | 443.56 | 88.71 | 15.8202 | 3.690e−13 | *** |
| Pathologist | 1 | 0.66 | 0.66 | 0.1174 | 0.7323 | |
| Disease:Pathologist | 5 | 15.34 | 3.07 | 0.5470 | 0.7405 | |
| Residuals | 204 | 1143.93 | 5.61 | | | |
| Probe2 | | | | | | |
| Disease | 5 | 1067.39 | 213.48 | 24.1234 | <2e−16 | *** |
| Pathologist | 1 | 13.02 | 13.02 | 1.4709 | 0.2263 | |
| Disease:Pathologist | 5 | 27.98 | 5.60 | 0.6324 | 0.6752 | |
| Residuals | 249 | 2203.50 | 8.85 | | | |
| Probe3 | | | | | | |
| Disease | 5 | 1098.49 | 219.70 | 21.0751 | <2e−16 | *** |
| Pathologist | 1 | 6.73 | 6.73 | 0.6458 | 0.4224 | |
| Disease:Pathologist | 5 | 29.72 | 5.94 | 0.5703 | 0.7227 | |
| Residuals | 243 | 2533.16 | 10.42 | | | |
| Probe4 | | | | | | |
| Disease | 5 | 631.8 | 126.4 | 9.3707 | 3.454e−08 | *** |
| Pathologist | 1 | 6.6 | 6.6 | 0.4869 | 0.4860 | |
| Disease:Pathologist | 5 | 13.1 | 2.6 | 0.1939 | 0.9647 | |
| Residuals | 246 | 3317.1 | 13.5 | | | |
| Probe5 | | | | | | |
| Disease | 5 | 754.30 | 150.86 | 25.2826 | <2e−16 | *** |
| Pathologist | 1 | 14.25 | 14.25 | 2.3875 | 0.1236 | |
| Disease:Pathologist | 5 | 7.54 | 1.51 | 0.2528 | 0.9381 | |
| Residuals | 248 | 1479.80 | 5.97 | | | |
| Probe6 | | | | | | |
| Disease | 5 | 721.91 | 144.38 | 11.8515 | 2.771e−10 | *** |
| Pathologist | 1 | 1.91 | 1.91 | 0.1568 | 0.6925 | |
| Disease:Pathologist | 5 | 47.82 | 9.56 | 0.7850 | 0.5613 | |
| Residuals | 246 | 2996.93 | 12.18 | | | |
| Probe7 | | | | | | |
| Disease | 5 | 1171.47 | 234.29 | 77.6802 | <2e−16 | *** |
| Pathologist | 1 | 8.84 | 8.84 | 2.9294 | 0.08847 | . |
| Disease:Pathologist | 5 | 46.36 | 9.27 | 3.0742 | 0.01063 | * |
| Residuals | 209 | 630.37 | 3.02 | | | |
| Probe8 | | | | | | |
| Disease | 5 | 209.82 | 41.96 | 6.4352 | 1.201e−05 | *** |
| Pathologist | 1 | 12.66 | 12.66 | 1.9407 | 0.16483 | |
| Disease:Pathologist | 5 | 71.20 | 14.24 | 2.1838 | 0.05654 | . |
| Residuals | 251 | 1636.76 | 6.52 | | | |
| Probe9 | | | | | | |
| Disease | 5 | 197.21 | 39.44 | 8.4348 | 2.015e−07 | *** |
| Pathologist | 1 | 7.33 | 7.33 | 1.5681 | 0.2116 | |
| Disease:Pathologist | 5 | 24.56 | 4.91 | 1.0505 | 0.3884 | |
| Residuals | 265 | 1239.17 | 4.68 | | | |

TABLE 21-continued

Analysis of Variance of H-Scores

| | Df | Sum Sq | Mean Sq | F value | Pr(>F) | |
|---|---|---|---|---|---|---|
| Probe10 | | | | | | |
| Disease | 5 | 1113.46 | 222.69 | 39.0730 | <2e−16 | *** |
| Pathologist | 1 | 1.01 | 1.01 | 0.1778 | 0.67371 | |
| Disease:Pathologist | 5 | 62.45 | 12.49 | 2.1916 | 0.05635 | . |
| Residuals | 213 | 1213.96 | 5.70 | | | |
| --- | | | | | | |
| Probe11 | | | | | | |
| Disease | 5 | 320.15 | 64.03 | 9.5553 | 2.416e−08 | *** |
| Pathologist | 1 | 1.28 | 1.28 | 0.1918 | 0.6618 | |
| Disease:Pathologist | 5 | 10.04 | 2.01 | 0.2996 | 0.9128 | |
| Residuals | 245 | 1641.76 | 6.70 | | | |
| --- | | | | | | |
| Probe12 | | | | | | |
| Disease | 5 | 832.26 | 166.45 | 27.8793 | <2e−16 | *** |
| Pathologist | 1 | 0.18 | 0.18 | 0.0307 | 0.8610 | |
| Disease:Pathologist | 5 | 15.16 | 3.03 | 0.5079 | 0.7701 | |
| Residuals | 248 | 1480.68 | 5.97 | | | |
| --- | | | | | | |
| Probe13 | | | | | | |
| Disease | 5 | 46.594 | 9.319 | 7.8408 | 8.674e−07 | *** |
| Pathologist | 1 | 0.044 | 0.044 | 0.0368 | 0.8481 | |
| Disease:Pathologist | 5 | 10.143 | 2.029 | 1.7069 | 0.1343 | |
| Residuals | 210 | 249.584 | 1.188 | | | |
| --- | | | | | | |
| Probe14 | | | | | | |
| Disease | 5 | 1305.69 | 261.14 | 23.9460 | <2e−16 | *** |
| Pathologist | 1 | 28.66 | 28.66 | 2.6279 | 0.10630 | |
| Disease:Pathologist | 5 | 142.90 | 28.58 | 2.6208 | 0.02492 | * |
| Residuals | 243 | 2649.98 | 10.91 | | | |
| --- | | | | | | |
| Probe15 | | | | | | |
| Disease | 5 | 401.02 | 80.20 | 21.268 | <2e−16 | *** |
| Pathologist | 1 | 13.17 | 13.17 | 3.493 | 0.0630 | . |
| Disease:Pathologist | 5 | 6.17 | 1.23 | 0.327 | 0.8963 | |
| Residuals | 214 | 807.02 | 3.77 | | | |
| --- | | | | | | |
| Probe16 | | | | | | |
| Disease | 5 | 2520.26 | 504.05 | 65.5572 | <2e−16 | *** |
| Pathologist | 1 | 0.15 | 0.15 | 0.0194 | 0.8892 | |
| Disease:Pathologist | 5 | 24.29 | 4.86 | 0.6318 | 0.6757 | |
| Residuals | 247 | 1899.12 | 7.69 | | | |
| --- | | | | | | |
| Probe17 | | | | | | |
| Disease | 5 | 530.64 | 106.13 | 13.0178 | 2.426e−11 | *** |
| Pathologist | 1 | 8.42 | 8.42 | 1.0325 | 0.31050 | |
| Disease:Pathologist | 5 | 109.96 | 21.99 | 2.6975 | 0.02131 | * |
| Residuals | 266 | 2168.55 | 8.15 | | | |
| --- | | | | | | |
| Probe19 | | | | | | |
| Disease | 5 | 1670.86 | 334.17 | 29.1960 | <2e−16 | *** |
| Pathologist | 1 | 2.17 | 2.17 | 0.1895 | 0.6637 | |
| Disease:Pathologist | 5 | 32.61 | 6.52 | 0.5698 | 0.7231 | |
| Residuals | 248 | 2838.56 | 11.45 | | | |
| --- | | | | | | |
| Probe20 | | | | | | |
| Disease | 5 | 964.71 | 192.94 | 34.2760 | <2e−16 | *** |
| Pathologist | 1 | 8.83 | 8.83 | 1.5687 | 0.2116 | |
| Disease:Pathologist | 5 | 19.60 | 3.92 | 0.6963 | 0.6267 | |
| Residuals | 245 | 1379.12 | 5.63 | | | |
| --- | | | | | | |
| Probe21 | | | | | | |
| Disease | 5 | 6.927 | 1.385 | 2.0604 | 0.07076 | |
| Pathologist | 1 | 0.464 | 0.464 | 0.6906 | 0.40670 | |
| Disease:Pathologist | 5 | 1.576 | 0.315 | 0.4687 | 0.79945 | |
| Residuals | 263 | 176.830 | 0.672 | | | |
| --- | | | | | | |
| Probe22 | | | | | | |
| Disease | 5 | 640.16 | 128.03 | 31.7250 | <2e−16 | *** |
| Pathologist | 1 | 1.64 | 1.64 | 0.4058 | 0.5247 | |
| Disease:Pathologist | 5 | 18.78 | 3.76 | 0.9305 | 0.4617 | |
| Residuals | 247 | 996.81 | 4.04 | | | |
| --- | | | | | | |
| Probe23 | | | | | | |
| Disease | 5 | 1915.62 | 383.12 | 46.5565 | <2e−16 | *** |
| Pathologist | 1 | 10.77 | 10.77 | 1.3092 | 0.2537 | |
| Disease:Pathologist | 5 | 20.92 | 4.18 | 0.5084 | 0.7698 | |
| Residuals | 246 | 2024.39 | 8.23 | | | |
| --- | | | | | | |
| Probe24 | | | | | | |
| Disease | 5 | 516.06 | 103.21 | 24.0786 | <2e−16 | *** |
| Pathologist | 1 | 9.52 | 9.52 | 2.2210 | 0.1376 | |
| Disease:Pathologist | 5 | 12.48 | 2.50 | 0.5823 | 0.7135 | |
| Residuals | 216 | 925.87 | 4.29 | | | |
| --- | | | | | | |
| Probe25 | | | | | | |
| Disease | 5 | 1761.26 | 352.25 | 34.5245 | <2e−16 | *** |
| Pathologist | 1 | 11.51 | 11.51 | 1.1285 | 0.2891 | |
| Disease:Pathologist | 5 | 41.49 | 8.30 | 0.8134 | 0.5411 | |
| Residuals | 248 | 2530.33 | 10.20 | | | |
| --- | | | | | | |
| Probe26 | | | | | | |
| Disease | 5 | 399.85 | 79.97 | 13.6548 | 1.428e−11 | *** |
| Pathologist | 1 | 0.30 | 0.30 | 0.0517 | 0.8204 | |
| Disease:Pathologist | 5 | 14.81 | 2.96 | 0.5056 | 0.7719 | |
| Residuals | 214 | 1253.31 | 5.86 | | | |
| --- | | | | | | |
| Probe27 | | | | | | |
| Disease | 5 | 117.92 | 23.58 | 6.2551 | 1.956e−05 | *** |
| Pathologist | 1 | 0.64 | 0.64 | 0.1695 | 0.6810 | |
| Disease:Pathologist | 5 | 25.52 | 5.10 | 1.3539 | 0.2431 | |
| Residuals | 212 | 799.31 | 3.77 | | | |
| --- | | | | | | |
| Probe28 | | | | | | |
| Disease | 5 | 1634.60 | 326.92 | 38.171 | <2e−16 | *** |
| Pathologist | 1 | 8.40 | 8.40 | 0.981 | 0.3229 | |
| Disease:Pathologist | 5 | 16.15 | 3.23 | 0.377 | 0.8643 | |
| Residuals | 267 | 2286.76 | 8.56 | | | |
| --- | | | | | | |

Signif. codes: 0 `*' 0.001 `' 0.01 `*' 0.05 `.' 0.1 ` ' 1

(d) Analysis of Results

In all cases (except for probe 21) the response of the probes was related to disease. This is not surprising since the probes have presumably been selected for this purpose. In no case is the response of the probe related to pathologist (at the p=0.05 level). This indicates that it would be safe to merge this data and use the two pathologists as two measurements on the data In a few cases, probes 7, 14, 17, there is some evidence of an interaction term gaining significance. This indicates that there may be some difference between pathologists in their scoring of some diseases. Some of these cases may well be due to an occasional outlier in the data.

(e) Conclusions

The results indicate that it is safe to merge this data for further analysis. The data indicate that the slight interactions in some cases between pathologist and disease appear to be attributed to random sources.

ii. Patient to Patient Variability

The variability from patient to patient was measured by the disease:disease variability of section 2(a)(i)(2) (see above, "Analysis of Variance of H-Scores").

iii. Marker-to-Marker Variability

Histograms were plotted (PathologistData.xls, worksheet: Histograms) showing the distribution of marker scores for each probe for Control vs. Cancer.

b. Marker Correlation Matrix Analyses

The population correlation coefficient ("Applied Mulitvariate Statistical Analysis", R. A. Johnson and D. W. Wichern, 2nd Ed,1988, Prentice-Hall, N.J.) measures the amount of linear association between a pair of random variables. Typically the distributions and associated parameters of the random variables are not known and the population correlation coefficient cannot be directly computed. In this case it is possible to compute the sample correlation coefficient from sample data. See FIG. 4. The sample correlation coefficient is, however, only an estimate of the population correlation coefficient. Moreover, because it is calculated on the basis of sample data it is possible, purely by chance, that it may indicate a strong positive or negative correlation when in reality there may be no actual relationship between the corresponding random variables ("Modern Elementary Statistics", J. E. Freund, 6th Ed, 1984, Prentice-Hall, N.J.).

The correlation coefficient measures the ability of one variable to predict the other. A strong linear association does not, however, imply a causal relationship. The square of the correlation coefficient is called the coefficient of determination. The coefficient of determination computed for a bivariate data set measures the proportion of the variability in one variable that can be accounted for by its linear relationship to the other. When dealing with several variables, the correlation coefficient can be calculated for each pair in turn and the set of coefficients can be written as a matrix called the correlation matrix. See FIG. 4.

The H-scores for the individual markers can be modeled as random variables. The sample correlation matrix for this multivariate data set can be computed from the input data described in the section titled "Input Data", above.

c. Pattern Recognition

Statistical pattern recognition is an approach to classifying signals or geometric objects on the basis of quantitative measurements (called features). Statistical pattern recognition essentially reduces to the problem of dividing the n-dimensional feature space into regions that correspond to the categories or classes of interest.

Three different classifier methodologies employed in this study are sensitive to different structural forms within the data.

For the Decision Tree method a preliminary analysis of different data combinations identified markers which were never used by C4.5 for the detection panel. These were removed from the analysis and this resulted in more consistent results, symptomatic of the left-out probes only contributing noise to the selection process.

Similarly a preliminary analysis of probes used in the detection panels identified the noisy probes for removal prior to the detailed analysis.

The Linear Discriminant Function method in SPSS has built-in stepwise processes for reducing the numbers of markers in the analysis. Typically, this reduced the probes used in the analysis to between 2 and 7.

The Logistic Regression method in R and SAS implement stepwise procedures for variable selection. In SAS, a best subsets variable selection option is also provided. In R, the stepwise methodology was used in conjunction with multiple random trials to develop a heuristic method for selecting variables based on the number of times a given feature was used in 100 random selections of training and test data (split 70%:30% respectively). Features with counts comparable to the count for artificial random feature were progressively eliminated until a minimal consistent set of features was obtained over 100 runs.

i. Statistical Methods

From the point of view of multivariate statistical analysis, the problem is one of estimating density functions in high-dimensional space (and partitioning this space into the regions of interest). Assuming that the distributions of random (feature) vectors are known, the theoretically best classifier is the Bayes classifier because it minimizes the probability of classification error (K. Fukunaga, "Statistical Pattern Recognition", $2^{nd}$ Ed., Academic Press 1990, p.3). Unfortunately the implementation of the Bayes classifier is difficult because of its complexity, especially when the dimensionality of the feature space is high. In practice, simpler parametric classifiers are used. Parametric classifiers are based on assumptions about the underlying density or discriminant functions. The most common such classifiers are linear and quadratic classifiers. In multivariate statistical analysis such classifiers fall under the heading of discriminant analysis. Discriminant analysis techniques are closely related to multivariate linear regression models and generalized linear models (encompassing logistic and multinomial regression).

(1) Logistic Regression with a Binomial Response (a) Background

The problem of selecting a set of markers to be used on a detection panel can be formulated as a logistic regression problem with a binomial response. The response variable is a factor with two levels: normal (no cancer) and abnormal (cancer). The explanatory variables are the marker H-scores.

The problem of selecting a set of markers to be used on a cancer discrimination panel can also be formulated as a logistic regression problem with a binomial response. The response variable is a factor with two levels: normal (not the cancer of interest) and abnormal (cancer of interest). The explanatory variables are the marker H-scores.

Stepwise variable selection can be used to select a subset of the original variables (markers) for use in discriminating between the two classes. This is a computationally expensive exercise and is best suited to a computer. Several commercial and public domain software packages—e.g., R, S-plus, and SAS—implement stepwise logistic regression.

Two different approaches to feature selection were investigated based on the stepwise variable selection procedures found in R and SAS respectively.

(b) Experimental Data

The data used for the present analysis consists of the H-scores for markers 1–17, and 19–28 for the cases examined by Pathologist 1 and Pathologist 2 and described elsewhere in this report. In addition, a dummy marker, 18, was added to the data set. The dummy marker consists of integer values from 0 to 12 selected at random from a uniform distribution.

(c) Method 1: Using the R Package (Version 1.4.1)

Computerized model fitting procedures generally cannot deal with missing data. This is the case for the glm (glm stands for generalized linear model) procedure used in R. Consequently when fitting a model using glm it was necessary to exclude all the cases for which there are one or more missing values. When fitting the initial full model, containing the 27 real markers and the single dummy marker, this reduces the data set to only 202 cases. With so few observations it was decided that the best way to perform variable selection, to train a classifier using the selected variables, and to assess its performance was to undertake 100 trials on random partitions of the data into train and test sets.

(i) Partitioning the Data into Train and Test Sets

At the start of each trial, the data is partitioned into a test set and a training set. This is done by randomly choosing 30% of the abnormals and 30% of the normals to form the test set, and using the remaining observations to form the training set.

(ii) Variable (Marker) Selection

At the start of each trial, the full model, which includes all of the variables (markers), is fitted to the training data. In R the logistic regression model is fitted using glm. The code fragment used is as follows:

my.model<-Class~X1+X2+X2+X3+X4+X5+X6+X7+X8+ X9+X10+X11+X12+X13+X14+X15+X16+X17+X18+ X19+X20+X21+X22+X23+X24+X25+X26+X27+X28 my.glm<-glm(my.model, family=binomial(link=logit), data=training.data)

The procedure stepAIC is then used to perform stepwise variable selection based on the Akaike Information Criterion (AIC). This procedure is part of the publicly available MASS library. The library and the procedure are described in "Modern Applied Statistics with S-PLUS" (W. N. Venables and B. D. Ripley, Springer-Verlag, Pathologist 3ew York, 1999). The R code fragment to do this is as follows:

my.step<-stepAIC(my.glm, direction=both)

The resulting model is then assessed on the test data. The code fragment used is as follows:

probability_is_abnormal<-predict(my.step,testing.data, type="response")

The performance of the classifier is recorded in terms of the actual error rate of misclassification (AER) and the area under the ROC curve (AUC). After the 100 trials, 100 models and their associated AERs and AUCs remain. A frequency table is constructed, recording the number of times each variable made an appearance in the 100 models. An example is shown in Table 22:

TABLE 22

| Variable | 1 | 2 | 3 | 4 | 5 | 6 | 7 | 8 | 9 | 11 | 12 | 14 |
|---|---|---|---|---|---|---|---|---|---|---|---|---|
| Frequency | 2 | 6 | 4 | 1 | 4 | 16 | 100 | 40 | 3 | 10 | 43 | 1 |
| Variable | 15 | 16 | 17 | 18 | 19 | 20 | | 22 | 23 | 24 | 25 | 28 |
| Frequency | 4 | 28 | 2 | 1 | 3 | 2 | | 2 | 18 | 10 | 84 | 4 |

This table is used to decide which markers to discard. First, all of the markers that have a frequency less than or equal to 10 are discarded. Next a cut-off frequency is chosen based on the frequency of the dummy marker (typically this is 1 or 1.5 times that of the dummy marker). All markers with a frequency less than this cut-off value are discarded. The remaining markers, along with the dummy marker, are then used as the full model for another 100 trials and the pruning process is repeated. If necessary, the severity of the pruning can be increased to force one or more markers out of the model. If necessary, the remaining markers can be used as the full model for yet another 100 trials. Pruning stops when the desired number of panel members is reached or the average AUC for the current model is less than that for the preceding model.

To illustrate the pruning process consider the table above. The table was obtained using the detection panel data. The shaded entries indicate those markers that are retained after pruning. Another 100 trials is performed using the following full model:

my.model<-Class~X6+X7+X8+X12+X16+X18+X23+X25

Again, a frequency table, Table 23 is constructed:

TABLE 23

| Variable | 6 | 7 | 8 | 12 | 16 | 18 | 23 | 25 |
|---|---|---|---|---|---|---|---|---|
| Frequency | 63 | 100 | 51 | 48 | 30 | 47 | 66 | 98 |

The shaded entries show the markers retained after pruning (using a cutoff of 47). Another 100 trials is performed using the following full model:

my.model<-Class~X6+X7+X8+X12+X18+X23+X25

Again, a frequency table, Table 24 is constructed:

TABLE 24

| Variable | 6 | 7 | 8 | 12 | 18 | 23 | 25 |
|---|---|---|---|---|---|---|---|
| Frequency | 96 | 100 | 23 | 73 | 3 | 88 | 98 |

At this point a cut-off of 50 is chosen. The shaded entries show the remaining markers for use on a 5 member panel. In each step, the average AUC increases: 94.37% → 95.45% → 95.78%.

(iii) Assessing the Performance of the Panel

To assess the performance of the panel, 100 trials were performed, as before, but without the stepwise selection procedure. For each trial, the AUC, sensitivity, and specificity are recorded. For the detection panel example above, the results are:

>my.model<-Class~X7+X25+X6+X23+X12
>summary(AUC)
  Min. 1st Qu. Median Mean 3rd Qu. Max.
  0.9289 0.9590 0.9615 0.9601 0.9630 0.9630
>summary(sensitivity)
  Min. 1st Qu. Median Mean 3rd Qu. Max.
  0.8519 0.9630 0.9630 0.9737 1.0000 1.0000
>summary(specificity)
  Min. 1st Qu. Median Mean 3rd Qu. Max.
  0.8378 0.9730 0.9730 0.9749 1.0000 1.0000

In summary, the panel has a sensitivity of 97.37% and a specificity of 97.49%. The area under the ROC is 96.01%.

(d) Method 2: Using SAS (Version 8.2)

Logistic regression can be performed in SAS using the procedure LOGISTIC. When the response variable is a two-level factor, the procedure fits a binary logit model (equivalent to glm in R with family=binomial and link=logit). SAS automatically excludes all of the missing multivariate observations for the model specified. Unlike R, SAS is able to perform a best subsets variable selection procedure. The code fragment in SAS needed to do this is as follows:

PROC LOGISTIC DATA=WORK.panel;
  CLASS Class;
  MODEL Class=X1 X2 X3 X4 X5 X6 X7 X8 X9 X10 X11 X12 X13 X14 X15 X16 X17 X18 X19 X20 X21 X22 X23 X24 X25 X26 X27 X28/SELECTION=SCORE BEST=28;
RUN;

This procedure is applied to the entire data set. The parameter BEST=28 directs SAS to find the best 28 single-variable models, the best 28 two-variable models, the best 28 three-variable models, up to the best 28 28-variable models.

(i) Assessing the Performance of the Panels

The procedure described in method 1 is used to assess the performance of each of the panels. The following, Table 25, was generated from the detection panel data. It lists results only for the two best one-, two-, three-, four-, and five-marker panels.

TABLE 25

| Panel | Panel members | Sensitivity | Specificity | Area under ROC |
|---|---|---|---|---|
| 1 | 7 | | | 94.28% |
| 2 | 28 | | | 80.14% |
| 3 | 7, 16 | | | 95.00% |
| 4 | 7, 15 | | | 94.59% |
| 5 | 7, 15, 16 | | | 95.94% |
| 6 | 1, 7, 16 | | | 95.33% |
| 7 | 1, 7, 15, 16 | | | 95.61% |
| 8 | 4, 7, 15, 16 | | | 95.34% |
| 9 | 1, 4, 7, 15, 16 | | | 95.30% |
| 10 | 1, 7, 11, 15, 16 | | | 95.57% |

(2) Linear Discriminant Analysis (a) Background

The commercial statistical package SPSS has procedures allowing simple linear discriminant functions to be design and tested.

A commonly used method is Fisher's Linear discriminant function. This finds the hyper-plane in feature space which gives a good separation of classes. For a two class problem where the class distributions have different means, but similar multivariate Gaussian distributions, this classifier gives optimum performance. The method can be extended heuristically to multi-class problems, but this was not applied in the study.

The method is simplistic in its approach but robust to problems associated with data sets containing a large number of features (the probes in our case number 27, giving problem for a data set comprising only some two hundred exemplars (cases)).

This package has a procedure for identifying the features which contribute well to the discrimination process. This "stepwise method" first finds the most discriminating feature. Other features are then sequentially added and evaluated against the classifier. Combinations are explored so the final solution may exclude features initially selected if better combinations are found. The number of features is gradually increased until a statistical test shows the remaining features do not contribute reliably to the classification process.

An estimate of the performance is gained by using the leave one out method. This removes one sample from the data set to form the training set. The left out sample is retained as the test set, applied to the classifier, and the resulting classification accumulated in the confusion matrix. The procedure is repeated for case in the data. This procedure gives an unbiased estimate of performance, but the estimate will have a high variance.

Method

In SPSS select the appropriate data set for analysis, select "Analyze", select "Classify", select "Discriminant . . . ", on the table select "Fishers method", "leave one out testing" and "use stepwise method". Enter the diagnosis as the grouping variable and enter all the features as the independents. Enter "OK" to complete the analysis. Pre-set values for other parameters were left as set.

The analysis output includes a list of the features used in the analysis, the canonical discriminant function and a confusion matrix and the correct-classification rate (1-error rate).

In order to compute an ROC curve the Canonical discriminant function is applied to the selected features to generate a new feature. In SPSS use Graphs, ROC to plot this curve ii. Hierarchical Methods: Decision Trees (1) Background Decision tree learning is one of the most widely used and practical methods for inductive inference. It is a method for classification that is robust to noisy data and capable of learning disjunctive expressions (Tom M. Mitchell, "Machine Learning", McGraw-Hill, New York, N.Y., 1997.)

The most popular and accessible machine learning package is "C4.5" the source code of which is published in: (J. Ross Quinlan, "C4.5: Programs for Machine Learning", Morgan Kaufmann, San Mateo Calif., 1993).

When a decision tree is being trained (on training data), the algorithm decides at each node of the tree which single attribute of the data to use at this node to best make a decision. Therefore when the tree is completely constructed, it will have selected some set of attributes to use and ignored others. In our application, using decision trees to process measurements gained from molecular probes, the decision tree has effectively chosen a panel of probes, and a method of combining the probe scores, which best explains the classification of the data. To obtain an unbiased estimate of the panel performance, the resulting tree must be evaluated on data which was not used in the training. One standard technique for doing this is cross-validation. A 10-fold cross-validation was employed.

Cross-validation is a technique for making the very best use of limited data. In 10-fold cross-validation the data is randomly split into 10 nearly-equal sized partitions, taking care to have approximately the same number of cases in a class across each partition. Then, the decision tree is trained on partitions 2–9 combined and tested on partition 1, then trained on partitions 1,3–9 combined and tested on partition 2, and so on for 10 trials rotating the held-out test set through the data once. In this manner tests are only ever performed on held-out data and so are unbiased, and all data is tested exactly once so an aggregate error rate across the whole data set can be computed.

Trees are usually constructed until they are a very good fit to the training data, then they are "pruned" back by clipping off "noisy" branches and leaves. This improves the generalization ability of the decision tree on unseen data and is essential to obtain good performance. The C4.5 package includes two methods for pruning trees first a standard tree pruning algorithm, second a rule extraction algorithm. In general, the tree based method was found to give superior results on this data. Therefore, the rule-based method is not reported.

(2) Data Preparation

Data on the response of various probes to normal tissue and five different cancers (Adenocarcinoma, Large Cell Carcinoma, Mesothelioma, Small Cell Lung Cancer, and Squamous Cell Carcinoma) was obtained as described elsewhere. The H-scores for probes 1–28, and pathologists Pathologist 1 and Pathologist 2 were extracted from the database and put into a flat data file. For the decision tree analysis each data point (even by two pathologists on a same physical slide) was taken to be an independent observation of the effect of disease on staining. This may slightly positively bias the performance of classification but should have no effect on panel selection.

The control categories of Emphysema, Granulomatous Disease, and Interstitial Lung Disease were grouped together and called "Normal".

For the detection panel all the cancers were grouped together and called "Abnormal" making this a 2-class problem.

For the single discrimination panel, the Normal cases were removed from the data to form a 5-class problem.

For the hold-out discrimination panels, each cancer was held out in turn and the remaining cancers grouped into "Other" to give a set of five 2-class problems.

C4.5 requires a ".names" file which describes the data and the attributes to be included in the analysis. An example names file for the discrimination panel is, Table 26:

TABLE 26

C4.5 Names file for MonoGen ZF21 diag data
Adenocarcinoma, Large Cell Carcinoma, Mesothelioma, Small Cell
Lung Cancer, Squamous Cell Carcinoma. | classes

| | |
|---|---|
| P1 | continuous. |
| P2 | continuous. |
| P3 | continuous. |
| P4 | continuous. |
| P5 | continuous. |
| P7 | continuous. |
| P8 | continuous. |
| P9 | continuous. |
| P10 | continuous. |
| P11 | continuous. |
| P12 | continuous. |
| P13 | continuous. |
| P14 | continuous. |
| P15 | continuous. |
| P16 | continuous. |
| P17 | continuous. |
| P18 | ignore. |
| P19 | continuous. |
| P20 | continuous. |
| P21 | continuous. |
| P22 | continuous. |
| P23 | continuous. |
| P24 | continuous. |
| P25 | continuous. |
| P26 | continuous. |
| P27 | continuous. |
| P28 | continuous. |

Probe 18 was missing from the data and was set to "ignore" in all the designs. Setting attributes to "ignore" in the names file is an easy and effective way of trimming probes from the panels and is used in the data analysis.

(3) Data Analysis

Ten-fold cross validation was run on each data set using the "xval.sh" script supplied with C4.5. Standard (default) parameters for the package were used. Cross validation is a technique developed for classifier training and testing on small data sets. It involves randomly splitting the data into N equal sized partitions. The clasifier is then trained on N-1 partitions together and tested on the remianing partition. This is repeated N times.

Since the decision tree trained in one cross-validation (CV) trial may differ from the tree obtained in another (different in both probes selected, and tree coefficients) the number of times each probe was selected by the tree in 10 trials was computed.

The first cull of probes was done by setting to ignore any probe which did not occur in a pruned tree 5 or more times out of the 10 CV trials.

Then the cross-validation was repeated with this smaller set of candidate probes. The second cull of probes was done by setting to ignore any probe which did not occur in a pruned tree 5 or more times out of the 10 CV trials. If any further probes dropped out, a third CV run was done.

The panels were selected by the various runs, and their estimated error performance are shown in the results tables. The panel performance for decision tree analysis is shown below, in Table 27.

TABLE 27

Panel Performance - Decision Trees

| | | Cancer | Control |
|---|---|---|---|
| Detection Panel | Cancer | 99.42% | 0.58% |
| Probes: 3, 7, 19, 25 and 28 | Control | 17.82% | 82.18% |
| | | Adeno | Others |
| Pair-wise Discrimination | Adeno | 67.74% | 32.26% |
| 4, 6, 14, 19 and 23 | Others | 11.20% | 88.80% |
| | | Squamous | Others |
| Pair-wise Discrimination | Squamous | 70.59% | 29.41% |
| 3, 6, 17, 19 and 25 | Others | 4.07% | 95.93% |
| | | Large Cell | Others |
| Pair-wise Discrimination | Large Cell | 36.36% | 63.64% |
| 1, 5, 10, 13, 21, 27 and 28 | Others | 7.37% | 92.63% |
| | | Mesothelioma | Others |
| Pair-wise Discrimination | Mesothelioma | 82.05% | 17.95% |
| 3, 12 and 16 | Others | 5.00% | 95.00% |
| | | Small Cell | Others |
| Pair-wise Discrimination | Small Cell | 69.23% | 30.77% |
| 12, 17, 20, 23 and 25 | Others | 1.49% | 98.51% |
| | | Cancer | Control |
| Detection (without probe 7) | Cancer | 89.60% | 10.40% |
| 6, 10, 16 and 19 | Control | 3.30% | 96.70% |
| | | Cancer | Control |
| Detection (only commercially preferred probes) | Cancer | 92.80% | 7.20% |
| 5, 6, 10, 16, 19 and 23 | Control | 5.49% | 94.51% |

An example decision tree structure is shown in below, in Tables 28 and 29, for discriminating between Small Cell Lung Cancer and the remaining four types of cancer.

C4.5 Output Format:

TABLE 28

P23 <= 3 :
| P25 <= 2 : Small Cell Lung Cancer (18.0)
| P25 > 2 :
| | P17 <= 5 : Small Cell Lung Cancer (2.0)
| | P17 > 5 :
| | | P20 <= 11 : Other (9.0)
| | | P20 > 11 : Small Cell Lung Cancer (2.0)
P23 > 3 :
| P12 > 7 : Other (120.0)
| P12 <= 7 :

TABLE 28-continued

| | P20 <= 2 : Other (5.0)
| | P20 > 2 : Small Cell Lung Cancer (4.0)
Tree saved Evaluation on training data (160 items):

| Before Pruning | | After Pruning | | |
|---|---|---|---|---|
| Size | Errors | Size | Errors | Estimate |
| 13 | 0(0.0%) | 13 | 0(0.0%) | (5.2%) << |

TABLE 29

Pictorial format:

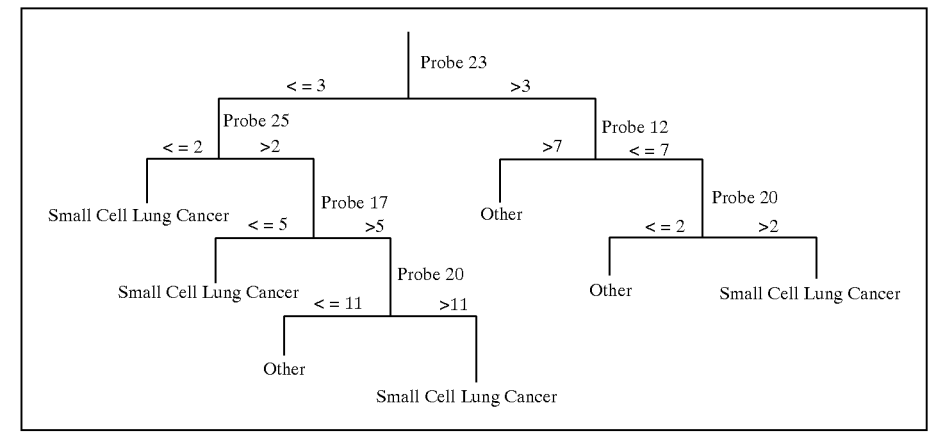

The panel performance for stepwise linear discrminant is shown below, in Table 30:

TABLE 30

| Panel Performance - Stepwise LD | | | |
|---|---|---|---|
| | | Cancer | Control |
| Detection Panel 1, 4, 7, 15 and 16 | Cancer | 92.24% | 7.76% |
| | Control | 1.16% | 98.84% |
| | | Adeno | Others |
| Pair-wise Discrimination 4, 5, 14, 19, 20, 25 and 27 | Adeno | 91.67% | 8.33% |
| | Others | 5.43% | 94.57% |
| | | Squamous | Others |
| Pair-wise Discrimination 1, 2, 3, 24, 25 and 26 | Squamous | 88.00% | 12.00% |
| | Others | 6.59% | 93.41% |
| | | Large Cell | Others |
| Pair-wise Discrimination 1 and 7 | Large Cell | 80.95% | 19.05% |
| | Others | 26.32% | 73.68% |
| | | Mesothelioma | Others |
| Pair-wise Discrimination 3, 12 and 16 | Mesothelioma | 96.67% | 3.33% |
| | Others | 4.65% | 95.35% |

TABLE 30-continued

Panel Performance - Stepwise LD

|  |  | Small Cell | Others |
|---|---|---|---|
| Pair-wise Discrimination 12, 19, 22 and 23 | Small Cell | 93.75% | 6.25% |
|  | Others | 5.00% | 95.00% |
|  |  | Cancer | Control |
| Detection (without probe 7) 1, 2, 3, 4, 10, 11, 15, 16, 23, 24, 27 and 28 | Cancer | 85.34% | 14.66% |
|  | Control | 2.33% | 97.67% |
|  |  | Cancer | Control |
| Detection (only commercially preferred probes) 8, 10, 11, 19, 23 and 28 | Cancer | 81.20% | 18.80% |
|  | Control | 1.16% | 98.84% |

The panel performance for stepwise logistic regression analysis is shown below, in Table 31:

TABLE 31

Panel Performance - Stepwise LR

|  |  | Cancer | Control |
|---|---|---|---|
| Detection Panel 6, 7, 12, 23 and 24 | Cancer | 97.49% | 2.63% |
|  | Control | 2.51% | 97.49% |
|  |  | Adeno | Others |
| Pair-wise Discrimination 14, 19, 20, 25 and 27 | Adeno | 96.39% | 3.61% |
|  | Others | 12.29% | 87.71% |
|  |  | Squamous | Others |
| Pair-wise Discrimination 3 and 10 | Squamous | 94.93% | 5.07% |
|  | Others | 35.86% | 64.14% |
|  |  | Large Cell | Others |
| Pair-wise Discrimination 1, 4, 6, 16 and 21 | Large Cell | 95.11% | 4.89% |
|  | Others | 61.00% | 39.00% |
|  |  | Mesothelioma | Others |
| Pair-wise Discrimination 3, 7, 12 and 16 | Mesothelioma | 95.07% | 4.93% |
|  | Others | 10.89% | 89.11% |
|  |  | Small Cell | Others |
| Pair-wise Discrimination 12, 13 and 23 | Small Cell | 98.90% | 1.10% |
|  | Others | 4.00% | 96.00% |
|  |  | Cancer | Control |
| Detection (without probe 7) 1, 10, 19, 23 and 28 | Cancer | 94.00% | 6.00% |
|  | Control | 5.80% | 94.20% |
|  |  | Cancer | Control |
| Detection (only commercially preferred probes) 10, 19, 20, 23 and 28 | Cancer | 93.88% | 6.12% |
|  | Control | 6.39% | 93.61% | iii. Neural Networks and Alternative Methods

Artificial neural networks ANN's are candidate pattern recognition techniques which could readily be applied to select features and design classifiers in association with this invention. However such techniques give little insight to the structure of the data and the influence of particular probes in the way that LDF gives. For this reason this class of algorithm was not used in this study. LDF stands for linear discriminant function, a linear combination of features whose result is thresholded to determine the classification.

This class of techniques includes algorithms such as Multi-Layer Perceptron MLP, Back-Prop, Kohonen's Self-Organizing Maps, Learning Vector Quantization, K-nearest neighbors and Genetic Algorithms.

iv. Special Topics
(1) Assumptions
Linear Discriminant Analysis
   Assumes the covariance matrices for the two classes are equal.
   Minimizes the cost of misclassification only when the two classes are multivariate normal.
   Assumes that the explanatory variables are continuous rather than categorical (in this study, the H-scores are categorical while in practice (i.e., in an automated system) intensity can be measured on a continuous scale).
Logistic Regression (Binomial Generalized Linear Models)
   See Venerables and Ripley, chapter 7 ("Modern Applied Statistics with S-PLUS" (W. N. Venables and B. D. Ripley, Springer-Verlag, N.Y., 1999)).

(2) Marker Rejection (De-Selection)

Computerized implementations of discriminant analysis and regression procedures include stepwise variable selection procedures; e.g., stepAIC in R. These procedures are designed to select the best subset of variables for use as explanatory variables. In reality, because of the step-by-step nature of these procedures, there is no guarantee that the best variables are selected for prediction (Johnson and Wichern, p. 299). Nevertheless such procedures do provide the basis for marker selection and de-selection.

(3) Pairwise Tests

Inherent problems in designing multiclass classifiers is discussed in "Applied Mulitvariate Statistical Analysis", R. A. Johnson and D. W. Wichern, 2nd Ed,1988, Prentice-Hall, N.J. This is motivation for developing several separate two-class classifiers (discrimination panel).

(4) Redundancy Consideration in Panel Composition

"Linear models form the core of classical statistics and are still the basis of much of statistical practice" "Modern Applied Statistics with S-PLUS" (W. N. Venables and B. D. Ripley, Springer-Verlag, N.Y., 1999. Linear models are the foundation for the t-test, analysis of variance (ANOVA), regression analysis, as well as a variety of multivariate methods including discriminant analysis. Explanatory variables may or may not enter the model as first-order terms. This is true also of (non-linear) logistic regression. The logistic regression model is simply a non-linear transformation of the linear regression model: the dependent variable is replaced by a log odds ratio (logit). In summary these statistical methods are based on linear relationships between the explanatory variables. Consequently, one avenue for seeking redundancy in panels is to identify highly correlated variables (markers). It may be possible to replace one marker with the other in a panel to achieve similar performance.

Another avenue for seeking redundancy in panels is to undertake a "best subsets" regression analysis. Given a starting model with all of the explanatory variables of interest, the aim is to find the best single-variable regression models, the best two-variable regression, etc. This methodology is implemented in the SAS statistical package.

(5) Use of Weighting Scores (a) Commercial and Clinical Considerations

For many reasons, including strategic and commercial factors; cost; availability; ease of use, it may be preferred to encourage the selection of certain probes in a panel and penalize the selection of others, at the same time trading this off against panel size or performance.

(b) Attribute Costing

Methods for such attribute weighting (in decision trees) have been proposed in the machine learning literature in other contexts such as the incorporation of background knowledge (M. Nunez, "The Use of Background Knowledge", Machine Learning 6: 231–250, 1991.), and the differential cost of obtaining information from robotic sensors (M. Tan, "Cost-sensitive Learning of Classification Knowledge and its Applications in Robotics", Machine Learning. 13: 7–33, 1993.)

Both of these cost-sensitive algorithms have been implemented in the literature by minor changes to the standard machine learning software package known as "C4.5 (J. Ross Quinlan, "C4.5: programs for machine learning", Morgan Kaufmann, CA. 1993.) For convenience, this approach was followed to implement the "EG2" algorithm of Nunez.

In the C4.5 decision tree construction phase, the algorithm compares each available attribute to split on and chooses the single one which maximizes the information gain, Gi. In the EG2 algorithm, $(2^{Gi}-1)/(C_i+1)$ is maximized which incorporates the cost of information for attribute i, Ci. The vector of weights need to be set a priori by the user.

(i) Code Modifications

The C4.5 source code was modified to implement the economic generalizer "EG2" algorithm proposed by M. Nunez (The Use of Background Knowledge, Machine Learning 6: 231–250, 1991.)

The exact modifications to the C4.5 package are as follows.

After the following lines in file "R8/Src/contin.c". (J. Ross Quinlan, "C4.5: programs for machine learning", Morgan Kaufmann, CA. 1993)

```
ForEach (i, Xp, Lp - 1)
    {
        if ( (Val = SplitGain[i] - ThreshCost) > BestVal )
        {
            BestI = i;
            BestVal = Val;
        }
    }
The new line:
BestVal = (powf(2.0, BestVal) - 1.0) / (AttributeCosts[Att] + 1.0);
``` is inserted. Where the vector of attribute costs has been previously read in from a text file maintained by the user.

(ii) Experimental Methodology.

The commercially preferred probes are: 2,4,5,6,8,10,11, 12,16,19,20,22,23,28.

For the sake of example, suppose the above probes are commercially preferred due to cost and it is desired to reselect the detection panel taking this cost into account.

The modified C4.5 decision tree software was used to give the commercially preferred probes a penalty of zero and non-commercially preferred probes a penalty of two. The 10-fold cross validated panel selection methodology (as described elsewhere) was run using the modified C4.5 algorithm (iii) Results The standard decision tree detection panel consists of probes 3, 7, 19, 25, 28. Resulting Panel Members: are 2, 6, 7, 10, 19, 25, 28 which used only 2 commercially preferred probes, P7 and P25. Note these probes have been selected by the method in spite of their increased cost due to their superior performance on this data. The panel is now larger: 7 probes versus 5 originally. There is no demonstratable drop in panel performance on this data although the performance will now be sub-optimal as a trade off against the reduced cost of probes.

(iv) Conclusion

A straightforward way has been established for incorporating costs of using probes into the panel selection methodology.

(c) Misclassification Costing (i) Background

For many reasons it may be desired to select an optimal panel bearing in mind that the costs of the different kinds of classification errors may vary. For example, it may be desired to select a panel which has an increased sensitivity to one disease (say Large Cell Carcinoma) and be willing to trade this off against reduced specificity and sensitivity elsewhere in the confusion matrix.

In theory a matrix of misclassification costs (of the same dimensions as the confusion matrix) to incorporate all the possible combinations of costs may be needed. In practice, only those costs which are non unity (the default) are entered.

The commercial decision tree software See5. (RuleQuest Research Pty Ltd, 30 Athena Avenue, St Ives Pathologist 3SW 2075, Australia. (http://www.rulequest.com)) incorporates this capability and was used in the following demonstration.

(ii) Aim

The standard joint discrimination panel (described elsewhere) consists of the members P2, 3, 4, 5, 12, 14, 16, 19, 22, 23, 28. And gives the following estimated confusion matrix:

| (a) | (b) | (c) | (d) | (e) | <-classified as |
|-----|-----|-----|-----|-----|-----------------|
| 24  | 4   | 2   | 5   | 2   | (a): class Adenocarcinoma |
| 8   | 7   | 3   | 5   | 4   | (b): class Large Cell Carcinoma |
| 1   | 1   | 33  | 1   | 4   | (c): class Mesothelioma |
| 6   | 2   | 1   | 23  |     | (d): class Small Cell Lung Cancer |
| 4   | 4   | 3   | 2   | 24  | (e): class Squamous Cell Carcinoma |

The sensitivity of Large Cell Carcinoma is low at 26 percent. If one wished to increase this sensitivity in a newly designed panel, the following method may be employed.

(iii) Methodology

The following costs file was generated:

| costs file for ZF21Discrim<br>Increase sensitivity for "Large Cell Carcinoma" | |
|---|---|
| Mesothelioma, Large Cell Carcinoma: | 10 |
| Adenocarcinoma, Large Cell Carcinoma: | 10 |
| Mesothelioma, Large Cell Carcinoma: | 10 |
| Small Cell Lung Cancer, Large Cell Carcinoma: | 10 |
| Squamous Cell Carcinoma, Large Cell Carcinoma: | 10 |

This file upweights the misclassification of Large Cell Carcinoma as any of the other cancers by a factor of 10. This will tend to increase the sensitivity of detection in this class (with reduced performance elsewhere) but no weighting can ensure perfect classification.

The standard decision tree panel selection methodology was applied (using See5 instead of C4.5).

(iv) Results

The new panel members are: P2, 3, 4, 5, 6, 9, 12, 14, 16, 17, 25, 28. With an estimated performance of:

| (a) | (b) | (c) | (d) | (e) | <-classified as |
|-----|-----|-----|-----|-----|-----------------|
| 20  | 13  | 1   | 1   | 2   | (a): class Adenocarcinoma |
| 3   | 13  | 3   | 2   | 6   | (b): class Large Cell Carcinoma |
| 1   | 9   | 27  | 2   | 1   | (c): class Mesothelioma |
| 2   | 9   |     | 21  |     | (d): class Small Cell Lung Cancer |
| 1   | 15  | 2   | 1   | 18  | (e): class Squamous Cell Carcinoma |

The above demonstrates that the estimated sensitivity of Large Cell Carcinoma has now increased to 48%.

(v) Conclusion

A straightforward way has been demonstrated for incorporating the differential costs of misclassification into the panel selection methodology.

d. Performance Metrics

Outputs provided by the analysis indicating the estimated performance of each method include:

i. ROC Analyses

Receiver Operating Characteristic (ROC) curves show the estimated percentage (or per unit probablility) of false positive and false negative scores for different threshold levels in the classifier. An indifferent classifier, unable to discriminate better than random choice, would present a ROC curve with equal true and false readings. The area under this curve would be 50% (0.5 probability).

Area Under the Curve (AUC) is often used as an overall estimate of classifier performance and most commercial discriminant function packages compute this figure. A perfect classifier would have 100% Area Under the Curve, a useless classifier would have an AUC near 50% (0.5).

ii. Confusion Matrices: Counts and Percentages

Confusion matrices show how data from the test set was classified. For pair wise tests these are counts of true positive, false positive, true negative or false negative scores. These may be shown as actual counts or as percentages. For the multi-way Panel, which attempts to give a unique diagnosis with one panel only, the confusion matrix would show counts for each correct classification. For instance, each time Small Cell carcinoma is detected as such it would be entered in one diagonal of the matrix. Incorrect scores; for instance how often a small cell carcinoma is incorrectly identified as squamous cell cancer would be entered in the appropriate off-diagonal element of the matrix. Error Rates are used to summarize data in the confusion matrix as the sum of all false classifications divided by the total number of classifications made, expressed as a percentage.

iii. Sensitivity and Specificity

Specificity refers to the extent to which any definition excludes invalid cases. If a definition has poor specificity, it is high in false positives. This means that it labels individuals as having a disorder when there is really no disorder present. Sensitivity refers to the extent to which any definition includes all valid cases. If a definition has poor sensitivity, it is high in false negatives (individuals who have a disorder present are falsely being diagnosed as not having one).

3. Data Analysis and Results a. Sample Size and Variability

Of the 354 cases in the combined Pathologist 1 and Pathologist 2 data set, only 202 cases possessed an H score for every marker (variable or feature).

The small number of complete observations and the large number of variables leads to estimation problems (curse of dimensionality). Hence it is necessary to prune severely back the number of variables used to build a classifier.

Due to the small number of observations it is not prudent to divide the data into separate training and testing sets (necessary for the robust estimation of classifier performance). For this reason, it was necessary to use resampling methods (such as cross-validation and multiple random trials).

The design of a multiclass classifier for cancer discrimination is difficult because there are so few observations for each type of cancer.

b. De-Selected Markers

Markers were de-selected using the methodology described above. Markers that were de-selected are represented by non-selection in the panels.

c. Detection Panel(s) Composition i. Selected Marker Probes

The selected marker probes for all three methods are summarized in FIG. 5.

ii. Minimum Selected Marker Set

For the detection panel it is clear that probe 7 delivered the best detection performance for a single marker. Combinations of probes were analyzed to see if a reliable panel could be obtained with more probes.

(1) Method

The Logistic Regression method allows best subsets to be ranked in terms of a performance measure (Fisher'score). This analysis was used to select the combinations from 1 through 5 probes. Fishers linear discriminant function and logit models (logistic regression) were used to illustrate the performance of these combinations. Data shown above.

(2) Conclusions

Probe 7 performs well on its own as a classifier; however, a drawback to using probe 7 alone is that probe 7 has a high false negative score. The best performance using Fishers linear discriminant function as a classifier was with probes 7 and 16. The variability of results amongst panels using other combinations suggests the noise added by more features is outweighing any potential to improve classification scores. The small number of incorrectly scored samples gives a poor representation of the statistics of these rarer events. A classifier designed with a larger number of cases may allow a better classifier to be designed. Techniques to select best combinations of probes using different classifiers may produce a different best panel, depending on the structure of the data.

iii. Supplemental Markers

It is shown that panels can be designed to suit the availability of different probes. Different methodologies can be used for selecting these subsets: Decision Trees, Logistic Regression, and Linear Discriminant Functions. Data are shown above.

Method

Using SPSS a Fisher's Linear Discriminant function was applied to the scores obtained from the panel in which constrains were applied due to access constraints. For example, all of the probes come from one vendor. Again, the stepwise option was selected to find the best combination of features. Performance was estimated using the Leave-One-Out cross validation test.

iv. Alternative Markers: Biological Mechanisms of Action (Functionally Equivalent Markers)

A person of ordinary skill in the art is able to determine functionally equivalent markers. The functional behaviors of the markers used in the panel are described throughout this document.

v. Marker Localization

The localizations of the various markers used in this study are described elsewhere in this document.

vi. Panel Performance

The performance of the three methods is shown above.

vii. Limitations on Interpretation of Panel Performance

Due to small data set and the need to employ resampling methods, there is the danger that the classifiers have been over-trained (made to fit the data too closely).

The panel performance using cytology specimens is difficult to forecast accurately since it is not clear whether sputum cytology samples will contain adequate numbers of cells that are representative of the cells analyzed in the histological validation studies. Nevertheless, given an adequate cellular sample size, one would expect the optimized panel to behave similarly with cytological specimens.

d. Discriminant Panel Composition i. A Single 5-Way Panel for all Cancers

Of the three analysis techniques, only a decision tree is amenable to a single 5-way panel. A single decision tree was therefore constructed to simultaneously classify all types of lung cancer. The panel members are shown FIG. 5. The panel performance is shown above in the panel performance tables.

ii. Panels for Discriminating a Single Type of Lung Cancer Against All Others

Linear discriminant functions are not well suited to performing simultaneous multi-class discrimination. The performance of five separate classifiers, each designed separately to discriminate one of the cancers from a pooled set of all the cancers, was analyzed. Such combinations have the potential to classify none of the cases as having one of the candidate cancers, or classify a single case as having two or more of the candidate cancers. This has a potential advantage in identifying inconsistent cases for further review.

It has been seen that the overall error rate of a single discriminant panel for all cancer types has a fairly high error rate (a five way classifier). In the panel performance data shown above, the performance of five pair-wise classifiers, each designed to identify one cancer from the four other possible cancers is shown. This approach is amenable to analysis using Decision Trees, and Linear Discriminant functions. The technique has the potential to deliver an ambiguous finding when applied, giving two or more diagnoses for a single patient, suggesting further clinical investigation. The technique has the potential to deliver no finding, again suggesting further investigation (perhaps a re-test with the detection panel).

iii. Panels to Account for Possibility of False Positive Cases From Detection Panels A further panel can be trained to discriminate among the false positive cases (from the detection panel) and the five cancer types. This involves selecting those individual cases from the detection panel that were incorrectly classified as abnormal. This trains a dedicated classifier on the 'harder' problem of detecting these 'special' cases. However, while this is a theoretically sound task, the data set only yielded four of these cases and the population was deemed to be under-represented for analysis.

iv. Selected Markers

The selected marker probes for all three methods are summarized in FIG. 5.

v. Minimum Selected Marker Set

This topic is addressed below under "Robustness of Approach Demonstrated by Similar Results Using Different Methods."

vi. Supplemental Markers

This topic is addressed below under "Robustness of Approach Demonstrated by Similar Results Using Different Methods."

vii. Alternative Markers: Biological Mechanisms of Action

A person of ordinary skill in the art is able to determine functionally equivalent markers. The functional behaviors of the markers used in the panel are described throughout this document.

viii. Marker Localization

The localization of the various markers used in this study are described throughout this document.

ix. Panel Performance

The performance of the three methods is summarized in FIG. 5.

e. Effect of Weighting Parameters

In addition to user-supplied weighting criteria for markers and also for disease states (classes) as discussed earlier, one can also use a binary weighting scheme. For example, if all non-DAKO supplied probes are weighted "0" and all DAKO-supplied probes are weighted "1", then the optimized panel will contain only DAKO-supplied probes. This is an improtant product design capability for any vendor who intends to develop and market molecular diagnostic panel kits using only their supplies.

f. Effect of Using Other (Non H-score) Objective Scoring Parameters i. Background The Pathology Review sheet contains a set of boxes as follows, in Table 32:

TABLE 32

| Intensity | None | Weak | Moderate | Intense |
|---|---|---|---|---|
| 0–5% | 0 | 0 | 0 | 0 |
| 6–25% | 1 | 1 | 1 | 1 |
| 26–50% | 2 | 2 | 2 | 2 |
| 51–75% | 3 | 3 | 3 | 3 |
| >75% | 4 | 4 | 4 | 4 |

The standard scoring system uses the "H score" which is obtained by grading the intensity as: none=0, weak=1, moderate=2, intense=3, and the percentage cells as: 0–5%=0, 6–25%=1, 26–50%=2, 51–75%=3, >75%=4, and then multiplying the two grades together. For example, 50% weakly stained plus 50% moderate stained would score 10=2×2+2×3.

ii. Method

An alternative scoring method was analyzed in which the response was divided into low, medium and high as follows:
(a) if more than 50% of cells had moderate or above stain HIGH
(b) if more than 50% of cells had no stain LOW
(c) otherwise MEDIUM The decision tree detection panel selection methodology was repeated using this 3-level factor instead of H-score. This caused the tree to split into 3 branches at each node, if required.

iii. Results

The panel selected was: Probes 3, 7, 10, 11, 16, 19, 20, 28

With an estimated performance of:

| Classified as -> | (a) | (b) | |
|---|---|---|---|
| Control (a) | 79 | 22 | Specificity = 78% |
| Cancer (b) | 24 | 149 | Sensitivity = 86% |

This should be compared to the reference performance with H-scores of:

| Classified as -> | (a) | (b) | |
|---|---|---|---|
| Control (a) | 85 | 6 | Specificity = 93% |
| Cancer (b) | 5 | 120 | Sensitivity = 96% | iv. Conclusions

There is a substantial loss of performance (larger panels, lower sensitivity and lower specificity when the proposed alternative scoring system is used.

Treating the H-score as a continuous variable (in the range 0 to 12) seems to be near optimal for panel selection on the data examined.

The many other possible scoring systems have not been examined, but may be feasible and applicable to the experimentally tested panel design and development methodology.

4. Lung Cancer Detection and Discrimination Panels

Listed below are exemplary lung cancer detection and discrimination panels determined by the above illustrative example. It is noted that although the panels listed below recite specific probes, each specific probe may be substituted by a correlate probe or a functionally related probe.

Detection (No Constraints)
    anti-Cyclin A combined with one or more additional probes
    anti-Cyclin A, anti-human epithelial related antigen (MOC-31)
    anti-Cyclin A, anti-ER-related P29
    anti-Cyclin A, anti-mature surfactant apoprotein B
    anti-Cyclin A, anti-human epithelial related antigen (MOC-31), anti-VEGF
    anti-Cyclin A, anti-human epithelial related antigen (MOC-31), anti-mature surfactant apoprotein B
    anti-Cyclin A, anti-mature surfactant apoprotein B, anti-human epithelial related antigen (MOC-31), anti-VEGF
    anti-Cyclin A, anti-mature surfactant apoprotein B, anti-human epithelial related antigen (MOC-31), anti-surfactant apoprotein A
    anti-Cyclin A, anti-mature surfactant apoprotein B, anti-human epithelial related antigen (MOC-31), anti-VEGF, anti-surfactant apoprotein A
    anti-Cyclin A, anti-mature surfactant apoprotein B, anti-human epithelial related antigen (MOC-31), anti-VEGF, anti-Cyclin D1
    anti-Cyclin A, anti-human epithelial related antigen (MOC-31) combined with one or more additional probes
    anti-Cyclin A, anti-ER-related P29 combined with one or more additional probes
    anti-Cyclin A, anti-mature surfactant apoprotein B combined with one or more additional probes anti-Cyclin A, anti-human epithelial related antigen (MOC-31), anti-VEGF combined with one or more additional probes anti-Cyclin A, anti-human epithelial related antigen (MOC-31), anti-mature surfactant apoprotein B combined with one or more additional probes anti-Cyclin A, anti-mature surfactant apoprotein B, anti-human epithelial related antigen (MOC-31), anti-VEGF combined with one or more additional probes anti-Cyclin A, anti-mature surfactant apoprotein B, anti-human epithelial related antigen (MOC-31), anti-surfactant apoprotein A combined with one or more additional probes anti-Cyclin A, anti-mature surfactant apoprotein B, anti-human epithelial related antigen (MOC-31), anti-VEGF, anti-surfactant apoprotein A combined with one or more additional probes anti-Cyclin A, anti-mature surfactant apoprotein B, anti-human epithelial related antigen (MOC-31), anti-VEGF, anti-Cyclin D1 combined with one or more additional probes Detection (W/O Anti-Cyclin A)

anti-Ki-67 combined with one or more additional probes.

anti-Ki-67 combined with any one probe selected from the group consisting of anti-VEGF, anti-human epithelial related antigen (MOC-31), anti-TTF-1, anti-EGFR, anti-proliferating cell nuclear antigen and anti-mature surfactant apoprotein B.

anti-Ki-67 combined with any two probes selected from the group consisting of anti-VEGF, anti-human epithelial related antigen (MOC-31), anti-TTF-1, anti-EGFR, anti-proliferating cell nuclear antigen and anti-mature surfactant apoprotein B.

anti-Ki-67 combined with any three probes selected from the group consisting of anti-VEGF, anti-human epithelial related antigen (MOC-31), anti-TTF-1, anti-EGFR, anti-proliferating cell nuclear antigen and anti-mature surfactant apoprotein B.

anti-Ki-67 combined with any four probes selected from the group consisting of anti-VEGF, anti-human epithelial related antigen (MOC-31), anti-TTF-1, anti-EGFR, anti-proliferating cell nuclear antigen and anti-mature surfactant apoprotein B.

anti-Ki-67 combined with any five probes selected from the group consisting of anti-VEGF, anti-human epithelial related antigen (MOC-31), anti-TTF-1, anti-EGFR, anti-proliferating cell nuclear antigen and anti-mature surfactant apoprotein B.

anti-Ki-67, anti-VEGF, anti-human epithelial related antigen (MOC-31), anti-TTF-1, anti-EGFR, anti-proliferating cell nuclear antigen and anti-mature surfactant apoprotein B anti-Ki-67 combined with any one probe selected from the group consisting of anti-VEGF, anti-human epithelial related antigen (MOC-31), anti-TTF-1, anti-EGFR, anti-proliferating cell nuclear antigen and anti-mature surfactant apoprotein B, and with one or more additional probes.

anti-Ki-67 combined with any two probes selected from the group consisting of anti-VEGF, anti-human epithelial related antigen (MOC-31), anti-TTF-1, anti-EGFR, anti-proliferating cell nuclear antigen and anti-mature surfactant apoprotein B, and with one or more additional probes.

anti-Ki-67 combined with any three probes selected from the group consisting of anti-VEGF, anti-human epithelial related antigen (MOC-31), anti-TTF-1, anti-EGFR, anti-proliferating cell nuclear antigen and anti-mature surfactant apoprotein B, and with one or more additional probes.

anti-Ki-67 combined with any four probes selected from the group consisting of anti-VEGF, anti-human epithelial related antigen (MOC-31), anti-TTF-1, anti-EGFR, anti-proliferating cell nuclear antigen and anti-mature surfactant apoprotein B, and with one or more additional probes.

anti-Ki-67 combined with any five probes selected from the group consisting of anti-VEGF, anti-human epithelial related antigen (MOC-31), anti-TTF-1, anti-EGFR, anti-proliferating cell nuclear antigen and anti-mature surfactant apoprotein B, and with one or more additional probes.

anti-Ki-67, anti-VEGF, anti-human epithelial related antigen (MOC-31), anti-TTF-1, anti-EGFR, anti-proliferating cell nuclear antigen, anti-mature surfactant apoprotein B and one or more additional probes.

Detection With Commerically Preferred Probes anti-Ki-67 combined with one or more additional probes.

anti-TTF-1 combined with one or more additional probes.

anti-EGFR combined with one or more additional probes.

anti-proliferating cell nuclear antigen combined with one or more additional probes.

two probes selected from the group consisting of anti-Ki-67, anti-TTF-1, anti-EGFR and anti-proliferating cell nuclear antigen.

three probes selected from the group consisting of anti-Ki-67, anti-TTF-1, anti-EGFR and anti-proliferating cell nuclear antigen.

anti-Ki-67, anti-TTF-1, anti-EGFR and anti-proliferating cell nuclear antigen two probes selected from the group consisting of anti-Ki-67, anti-TTF-1, anti-EGFR and anti-proliferating cell nuclear antigen, and one or more additional probes.

three probes selected from the group consisting of anti-Ki-67, anti-TTF-1, anti-EGFR and anti-proliferating cell nuclear antigen, and one or more additional probes.

anti-Ki-67, anti-TTF-1, anti-EGFR, anti-proliferating cell nuclear antigen, and one or more additional probes.

Discrimination Between Adenocarcinoma And Other Lung Cancers anti-mucin 1 and anti-TTF-1 anti-mucin 1 and anti-TTF-1 combined with any one probe selected from the group consisting of anti-VEGF, anti-surfactant apoprotein A, anti-BCL2, anti-ER-related P29 and anti-Glut 3 anti-mucin 1 and anti-TTF-1 combined with and two probes selected from the group consisting of anti-VEGF, anti-surfactant apoprotein A, anti-BCL2, anti-ER-related P29 and anti-Glut 3 anti-mucin 1 and anti-TTF-1 combined with any three probes selected from the group consisting of anti-VEGF, anti-surfactant apoprotein A, anti-BCL2, anti-ER-related P29 and anti-Glut 3 anti-mucin 1 and anti-TTF-1 combined with any four probes selected from the group consisting of anti-VEGF, anti-surfactant apoprotein A, anti-BCL2, anti-ER-related P29 and anti-Glut 3 anti-VEGF, anti-surfactant apoprotein A, anti-mucin 1, anti-TTF-1, anti-BCL2, anti-ER-related P29 and anti-Glut 3 anti-mucin 1, anti-TTF-1 and one or more additional probes anti-mucin 1 and anti-TTF-1 combined with any one probe selected from the group consisting of anti-VEGF, anti-surfactant apoprotein A, anti-BCL2, anti-ER-related P29 and anti-Glut 3, and with one or more additional probes anti-mucin 1 and anti-TTF-1 combined with and two probes selected from the group consisting of anti-VEGF, anti-surfactant apoprotein A, anti-BCL2, anti-ER-related P29 and anti-Glut 3, and with one or more additional probes anti-mucin 1 and anti-TTF-1 combined with any three probes selected from the group consisting of anti-VEGF, anti-surfactant apoprotein A, anti-BCL2, anti-ER-related P29 and anti-Glut 3, and with one or more additional probes anti-mucin 1 and anti-TTF-1 combined with any four probes selected from the group consisting of anti-VEGF, anti-surfactant apoprotein A, anti-BCL2, anti-ER-related P29 and anti-Glut 3, and with one or more additional probes anti-VEGF, anti-surfactant apoprotein A, anti-mucin 1, anti-TTF-1, anti-BCL2, anti-ER-related P29, anti-Glut 3 and one or more additional probes Discrimination Between Squamous Cell Carcinoma And Other Lung Cancers anti-CD44v6 combined with one or more additional probes anti-CD44v6 combined with any one probe selected from the group consisting of anti-VEGF, anti-thrombomodulin, anti-Glut 1, anti-ER-related P29 and anti-melanoma-associated antigen 3 anti-CD44v6 combined with any two probes selected from the group consisting of anti-VEGF, anti-thrombomodulin, anti-Glut 1, anti-ER-related P29 and anti-melanoma-associated antigen 3 anti-CD44v6 combined with any three probes selected from the group consisting of anti-VEGF, anti-thrombomodulin, anti-Glut 1, anti-ER-related P29 and anti-melanoma-associated antigen 3 anti-CD44v6 combined with any four probes selected from the group consisting of anti-VEGF, anti-thrombomodulin, anti-Glut 1, anti-ER-related P29 and anti-melanoma-associated antigen 3 anti-CD44v6, anti-VEGF, anti-thrombomodulin, anti-Glut 1, anti-ER-related P29 and anti-melanoma-associated antigen 3 anti-CD44v6 combined with any one probe selected from the group consisting of anti-VEGF, anti-thrombomodulin, anti-Glut 1, anti-ER-related P29 and anti-melanoma-associated antigen 3, and with one or more additional probes anti-CD44v6 combined with any two probes selected from the group consisting of anti-VEGF, anti-thrombomodulin, anti-Glut 1, anti-ER-related P29 and anti-melanoma-associated antigen 3, and with one or more additional probes anti-CD44v6 combined with any three probes selected from the group consisting of anti-VEGF, anti-thrombomodulin, anti-Glut 1, anti-ER-related P29 and anti-melanoma-associated antigen 3, and with one or more additional probes anti-CD44v6 combined with any four probes selected from the group consisting of anti-VEGF, anti-thrombomodulin, anti-Glut 1, anti-ER-related P29 and anti-melanoma-associated antigen 3, and with one or more additional probes anti-CD44v6, anti-VEGF, anti-thrombomodulin, anti-Glut 1, anti-ER-related P29, anti-melanoma-associated antigen 3 and one or more additional probes Discrimination Between Large Cell Carcinoma And Other Lung Cancers anti-VEGF combined with one or more additional probes.

anti-VEGF and anti-p120 anti-VEGF and anti-Glut 3 anti-VEGF, anti-p120 and anti-Cyclin A anti-VEGF, anti-p120 and one or more additional probes anti-VEGF, anti-Glut 3 and one or more additional probes anti-VEGF, anti-p120, anti-Cyclin A and one or more additional probes Discrimination Between Mesothelioma And Other Lung Cancers anti-CD44v6 combined with one or more additional probes.

anti-proliferating cell nuclear antigen combined with one or more additional probes.

anti-human epithelial related antigen (MOC-31) combined with one or more additional probes.

two probes selected from the group consisting of anti-CD44v6, anti-proliferating cell nuclear antigen and anti-human epithelial related antigen (MOC-31), combined with one or more additional probes anti-CD44v6, anti-proliferating cell nuclear antigen, anti-human epithelial related antigen (MOC-31) and one or more additional probes.

Discrimination Between Small Cell And Other Lung Cancers anti-proliferating cell nuclear antigen combined with one or more additional probes.

anti-BCL2 combined with one or more additional probes.

anti-EGFR combined with one or more additional probes.

two probes selected from the group consisting of anti-proliferating cell nuclear antigen, anti-BCL2 and anti-EGFR anti-proliferating cell nuclear antigen, anti-BCL2, anti-EGFR two probes selected from the group consisting of anti-proliferating cell nuclear antigen, anti-BCL2 and anti-EGFR, combined with one or more additional probes anti-proliferating cell nuclear antigen, anti-BCL2, anti-EGFR and one or more additional probes Simultaneous Discrimination Of Adenocarcinoma, Squamous Cell Carcinoma, Large Cell Carcinoma, Mesothelioma And Small Cell Carcinoma two or more probes selected from anti-VEGF, anti-thrombomodulin, anti-CD44v6, anti-surfactant apoprotein A, anti-proliferating cell nuclear antigen, anti-mucin 1, anti-human epithelial related antigen (MOC-31), anti-TTF-1, anti-N-cadherin, anti-EGFR and anti-proliferating cell nuclear antigen anti-VEGF, anti-thrombomodulin, anti-CD44v6, anti-surfactant apoprotein A, anti-proliferating cell nuclear antigen, anti-mucin 1, anti-human epithelial related antigen (MOC-31), anti-TTF-1, anti-N-cadherin, anti-EGFR and anti-proliferating cell nuclear antigen two or more probes selected from anti-VEGF, anti-thrombomodulin, anti-CD44v6, anti-surfactant apoprotein A, anti-proliferating cell nuclear antigen, anti-mucin 1, anti-human epithelial related antigen (MOC-31), anti-TTF-1, anti-N-cadherin, anti-EGFR and anti-proliferating cell nuclear antigen, combined with one or more additional probes anti-VEGF, anti-thrombomodulin, anti-CD44v6, anti-surfactant apoprotein A, anti-proliferating cell nuclear antigen, anti-mucin 1, anti-human epithelial related antigen (MOC-31), anti-TTF-1, anti-N-cadherin, anti-EGFR and anti-proliferating cell nuclear antigen, combined with one or more additional probes 5. Conclusions a. Validity of Panel Approach to Molecular Diagnostics i. Non-Intuitive Solutions Histograms were plotted (PathologistData.xls, worksheet: Histograms) showing the distribution of marker scores for each probe for Control vs. Cancer. It is clear from these histograms that an intuitive selection of probes for specific panels is certainly not obvious and the invention described does allow effective combinations to be found in the absence of an obvious method.

ii. Optimization for Varied Product Applications iii. Robustness of Approach Demonstrated by Similar Results Using Different Methods Detailed scrutiny of the results obtained by the various analyses in the body of this report, and as summarized in the tables and figures, shows the following findings.

1. Careful scrutiny of the performance of individual probes does not make apparent probe combinations that might perform better than any one probe alone.

2. All three classification methodologies evaluated hone in on similar sets of features. The small differences can be attributed to the data structure that may favor one classifier over another.

3. All the classifiers designed with one of these methods were shown to give good performance when tested on data from an independent pathologist, unseen during the design process. This gives high confidence in the invention.

4. A detection panel based on probe 7 alone gives a high performance.

5. If probe 7 is combined with probe 16 or 25 then a better performance is obtained.

6. While combinations of other probes with probe 7 appear to improve performance further, the number of extra cases captured is so low that they may be unrepresentative and the classifier so designed may not generalize.

7. The performance of panels selected from probes excluding probe 7 provided some discrimination, good enough in comparison with current practice using human screening, but perhaps not good enough for an automated cytometer in tomorrow's clinical diagnostic cytology world (see FIG. 6).

8. Other combinations of probes can provide a useful, but lesser, performance.

9. If some probes become unavailable this invention allows the selection of other combinations of probes. This was illustrated by classifier designs based on a commercially preferred set of probes only. See FIG. 7.

10. The invention allows a weighting to be applied against costly probes. Rather than totally excluding them from the analysis this allows their inclusion in the panel if their contribution is important.

11. The invention allows the design of single lung cancer type specific discrmination panels that can discriminate one type of lung cancer from among all other cancers.

12. Analysis of the performance of a single panel to classify five cancers showed discrimination was possible but the overall error rate was worse than a set of five panels each designed to discriminate one of the cancers from the others.

13. A very useful discrimination was obtained with the combination of five two way classifiers.

14. Common sets of probes were selected by the three classification methodologies for the five discrimination panels, again giving confidence in this result.

15. Probes for isolating cases of Adenocarcinoma are 1, 14, 19, 20, 25, and 27.

16. Probes for isolating cases of Squamous Cell cancer are 1, 2, 3, 24, 25, and 26.

17. Probes for isolating cases of Large Cell cancer are 1 and 7 or 1, and 21.

18. Probes for isolating cases of Mesothelioma are 3, 12, and 16.

19. Probes for isolating cases of Small Cell cancer are 12, 20, and 23.

20. Probes for recognizing all cancers simultaneously are 1, 2, 3, 4, 12, 14, 19, 22, 23, and 28.

21. An advantage of using the multiple pair-wise panels as defined by this invention is that doubtful cases may not score on any of the five panels, also confusing cases may show on two or more panels. Such anomalous reports would alert the cytologist that further analysis is indicated.

iv. Risk Management Study

All the tests applied in this study were statistical in nature. There is a risk that probes selected on the basis of small improvements in performance will have statistical variations when tested on new data. To give confidence in the results, the best classifier emerging from the Linear Discriminant analysis on the Pathologist 1 and Pathologist 2 data was tested. It should be remembered that the Pathologist 3 data was statistically different from the Pathologist 1 and Pathologist 2 data, so if good performances are obtained when tests using the Pathologist 3 data, then this would be encouraging indeed.

(1) Report on Testing with Unseen Data—Detection Panel (a) Method

In the Section titled "Detection Panel(s) Composition" above, we showed that good classification is obtained with features 7 and 16. Using SPSS all the Pathologist 3 data that reported H scores for both 7 and 16 was selected. Then, using Transform and Compute, the canonical discrimination function was generated as a new feature. The performance of this feature alone was then tested.

(b) Results

These are the results of testing the classifier designed on Pathologist 1 and Pathologist 2 data and testing on Pathologist 3 data. The classifier was designed using the linear discriminant function on probes 7 and 16. The Canonical Pathologist 2 function was =0.965* Probe7-0.298* Probe16.

Classification Results on Pathologist 3 data using probes 7 and 16

|  |  | Predicted Group Membership | | Total |
|---|---|---|---|---|
|  | Diagnosis (UCLA) | 0 | 1 |  |
| Original Count | 0 | 20 | 1 | 21 |
|  | 1 | 6 | 41 | 47 |
| % | 0 | 95.2 | 4.8 | 100.0 |
|  | 1 | 12.8 | 87.2 | 100.0 |
| Cross-validated Count | 0 | 20 | 1 | 21 |
|  | 1 | 6 | 41 | 47 |
| % | 0 | 95.2 | 4.8 | 100.0 |
|  | 1 | 12.8 | 87.2 | 100.0 | a Cross validation is done only for those cases in the analysis. In cross validation, each case is classified by the functions derived from all cases other than that case.
b 89.7% of original grouped cases correctly classified.
c 89.7% of cross-validated grouped cases correctly classified.

This is better than classifying the Pathologist 3 data on probe 7 only show as follows Classification Results on Pathologist 3 data using probes 7 only

|  |  | Predicted Group Membership | | Total |
|---|---|---|---|---|
|  | Diagnosis (UCLA) | 0 | 1 |  |
| Original Count | 0 | 20 | 1 | 21 |
|  | 1 | 8 | 39 | 47 |
| % | 0 | 95.2 | 4.8 | 100.0 |
|  | 1 | 17.0 | 83.0 | 100.0 |
| Cross-validated Count | 0 | 20 | 1 | 21 |
|  | 1 | 8 | 39 | 47 |
| % | 0 | 95.2 | 4.8 | 100.0 |
|  | 1 | 17.0 | 83.0 | 100.0 | a Cross validation is done only for those cases in the analysis. In cross validation, each case is classified by the functions derived from all cases other than that case.
b 86.8% of original grouped cases correctly classified.
c 86.8% of cross-validated grouped cases correctly classified.

(c) Conclusion

This gives confidence that the two-probe classifier based on 7 and 16 is better than probe 7 alone.

(2) Report on Testing With Unseen Data—Discrimination Panel (a) Background

Reported below is the performance of the classifier designed with Pathologist 1 and Pathologist 2 data using LDF and tested with the unseen Pathologist 3 data. The numbers of cases at the design stage was relatively small and the numbers in the test data are also small, so a good degree of variability can be expected between performance on the first and second set.

(b) Method

In SPSS, the canonical discrimination functions derived in the section titled "Pattern recognition", were built and tested on Pathologist 3 data for all five classes of cancer (c) Results Mesothelioma LDF=probe3sc * 0.385−probe12s * 0.317+probe6s * 1.006

Classification Results

| | | Meso = 1, others = 0 | Predicted Group Membership | | Total |
|---|---|---|---|---|---|
| | | | 0 | 1 | |
| Original | Count | 0 | 38 | 2 | 40 |
| | | 1 | 1 | 7 | 8 |
| | % | 0 | 95.0 | 5.0 | 100.0 |
| | | 1 | 12.5 | 87.5 | 100.0 |
| Cross-validated | Count | 0 | 38 | 2 | 40 |
| | | 1 | 1 | 7 | 8 |
| | % | 0 | 95.0 | 5.0 | 100.0 |
| | | 1 | 12.5 | 87.5 | 100.0 | a Cross validation is done only for those cases in the analysis. In cross validation, each case is classified by the functions derived from all cases other than that case.
b 93.8% of original grouped cases correctly classified.
c 93.8% of cross-validated grouped cases correctly classified.

Small cell cancer LDF=probe12s * 0.575−probe20s * 0.408−probe22s * 0.423+probe23s* 0.334

Classification Results

| | | Small = 1, others = 0 | Predicted Group Membership | | Total |
|---|---|---|---|---|---|
| | | | 0 | 1 | |
| Original | Count | 0 | 39 | 3 | 42 |
| | | 1 | 1 | 5 | 6 |
| | % | 0 | 92.9 | 7.1 | 100.0 |
| | | 1 | 16.7 | 83.3 | 100.0 |
| Cross-validated | Count | 0 | 39 | 3 | 42 |
| | | 1 | 1 | 5 | 6 |
| | % | 0 | 92.9 | 7.1 | 100.0 |
| | | 1 | 16.7 | 83.3 | 100.0 | a Cross validation is done only for those cases in the analysis. In cross validation, each case is classified by the functions derived from all cases other than that case.
b 91.7% of original grouped cases correctly classified.
c 91.7% of cross-validated grouped cases correctly classified.

Squamous cell cancer LDF=−probe1sc * 0.328−probe2sc * 0.295+probe3sc * 0.741+probe24s * 0.490+probe25s * 0.393+probe26s * 0.426

Classification Results

| | | Squamous = 1, others = 0 | Predicted Group Membership | | Total |
|---|---|---|---|---|---|
| | | | 0 | 1 | |
| Original | Count | 0 | 31 | 4 | 35 |
| | | 1 | 2 | 9 | 11 |
| | % | 0 | 88.6 | 11.4 | 100.0 |
| | | 1 | 18.2 | 81.8 | 100.0 |

Classification Results

| Squamous = 1, others = 0 | | | Predicted Group Membership | | Total |
|---|---|---|---|---|---|
| | | | 0 | 1 | |
| Cross-validated | Count | 0 | 31 | 4 | 35 |
| | | 1 | 2 | 9 | 11 |
| | % | 0 | 88.6 | 11.4 | 100.0 |
| | | 1 | 18.2 | 81.8 | 100.0 | a Cross validation is done only for those cases in the analysis. In cross validation, each case is classified by the functions derived from all cases other than that case.
b 87.0% of original grouped cases correctly classified.
c 87.0% of cross-validated grouped cases correctly classified.

Large cell cancer LDF=probe1sc * 0.847+probe7sc * 0.452

Classification Results

| Large = 1, others = 0 | | | Predicted Group Membership | | Total |
|---|---|---|---|---|---|
| | | | 0 | 1 | |
| Original | Count | 0 | 23 | 15 | 38 |
| | | 1 | 4 | 5 | 9 |
| | % | 0 | 60.5 | 39.5 | 100.0 |
| | | 1 | 44.4 | 55.6 | 100.0 |
| Cross-validated | Count | 0 | 23 | 15 | 38 |
| | | 1 | 4 | 5 | 9 |
| | % | 0 | 60.5 | 39.5 | 100.0 |
| | | 1 | 44.4 | 55.6 | 100.0 | a Cross validation is done only for those cases in the analysis. In cross validation, each case is classified by the functions derived from all cases other than that case.
b 59.6% of original grouped cases correctly classified.
c 59.6% of cross-validated grouped cases correctly classified.

The lower, but useful, performance was on a classifier designed and tested with a very small number of cases of large cell cancer, so this result is still very encouraging.

Adenocarcincoma, LDF=−probe4sc * 0.515+probe5sc * 0.299−probe14s * 0.485−probe19s* 0.347+probe20s* 0.723+probe25s* 03.27+probe27s * 0.327

Classification Results

| Adeno = 1, Others = 0 | | | Predicted Group Membership | | Total |
|---|---|---|---|---|---|
| | | | 0 | 1 | |
| Original | Count | 0 | 29 | 5 | 34 |
| | | 1 | 0 | 14 | 14 |
| | % | 0 | 85.3 | 14.7 | 100.0 |
| | | 1 | .0 | 100.0 | 100.0 |

Classification Results

| Adeno = 1, Others = 0 | | | Predicted Group Membership | | Total |
|---|---|---|---|---|---|
| | | | 0 | 1 | |
| Cross-validated | Count | 0 | 29 | 5 | 34 |
| | | 1 | 0 | 14 | 14 |
| | % | 0 | 85.3 | 14.7 | 100.0 |
| | | 1 | .0 | 100.0 | 100.0 | a Cross validation is done only for those cases in the analysis. In cross validation, each case is classified by the functions derived from all cases other than that case.
b 89.6% of original grouped cases correctly classified.
c 89.6% of cross-validated grouped cases correctly classified.

(d) Conclusion

It is very encouraging to note the performance of these classifiers stand up to the tests of applying unseen data. This gives a very high confidence in the ability to detect the individual cancers.

(3) Training and Testing on Data From Different Patients and Pathologists

As a "final final" test of robustness a LDF was trained on the data that was reviewed by both Pathologist 1 and Pathologist 2. This removes data reviewed by Pathologist 3. Hence testing on data reviewed by both Pathologist 3 plus Pathologist 1 data is not biased. Previously the test process was biased through using data from the same patient for test and train.

LDF produced the same set of features except for probe 4 which was not included. The LDF was=probe1sc * 0.288+ probe7sc * 0.846−probe5s * 0.249−probe16s * 0.534

Classification Results
Area under the Curve = .977

| Diagnosis (UCLA) | | | Predicted Group Membership | | Total |
|---|---|---|---|---|---|
| | | | 0 | 1 | |
| Original | Count | 0 | 20 | 0 | 20 |
| | | 1 | 9 | 37 | 46 |
| | % | 0 | 100.0 | .0 | 100.0 |
| | | 1 | 19.6 | 80.4 | 100.0 |
| Cross-validated | Count | 0 | 20 | 0 | 20 |
| | | 1 | 9 | 37 | 46 |
| | % | 0 | 100.0 | .0 | 100.0 |
| | | 1 | 19.6 | 80.4 | 100.0 | a Cross validation is done only for those cases in the analysis. In cross validation, each case is classified by the functions derived from all cases other than that case.
b 86.4% of original grouped cases correctly classified.
c 86.4% of cross-validated grouped cases correctly classified.

Still a reasonable result, but a similar result, but with a smaller area under the curve, was obtained with probe7 alone on Pathologist 3 only data Classification Results
Area under the curve = .908

|  |  | Diagnosis (UCLA) | Predicted Group Membership | | Total |
|---|---|---|---|---|---|
|  |  |  | 0 | 1 |  |
| Original | Count | 0 | 19 | 1 | 20 |
|  |  | 1 | 7 | 39 | 46 |
|  | % | 0 | 95.0 | 5.0 | 100.0 |
|  |  | 1 | 15.2 | 84.8 | 100.0 |
| Cross-validated | Count | 0 | 19 | 1 | 20 |
|  |  | 1 | 7 | 39 | 46 |
|  | % | 0 | 95.0 | 5.0 | 100.0 |
|  |  | 1 | 15.2 | 84.8 | 100.0 | a Cross validation is done only for those cases in the analysis. In cross validation, each case is classified by the functions derived from all cases other than that case.
b 87.9% of original grouped cases correctly classified.
c 87.9% of cross-validated grouped cases correctly classified.

What is claimed is:

1. A panel for detecting lung cancer, wherein:
   (a) said panel comprises a plurality of probes each of which specifically binds to a marker associated with lung cancer,
   (b) the pattern of binding of the component probes of the panel to cells in a cytology sample is diagnostic for the presence of lung cancer, and
   (c) said plurality of probes comprises a probe that binds to cyclin A or a correlate marker thereof and at least two probes, each of which binds to a marker selected from the group consisting of SP-B, HERA, ER-related(p29) and correlate markers thereof as depicted in the correlation matrix shown in FIG. 4.

2. A cell-based method for detecting lung cancer, comprising contacting cells from a cytology sample on one or more microscope slides with a panel comprising a plurality of probes and analyzing the pattern of binding of the component probes of the panel to cells in said cytology sample to detect lung cancer,
   wherein said plurality of probes comprises a probe that binds to cyclin A or a correlate marker thereof and at least two probes, each of which binds to a marker selected from the group consisting of SP-B, HERA, ER-related(p29), and correlate markers thereof as depicted in the correlation matrix shown in FIG. 4.

3. A panel for detecting lung cancer, wherein said panel comprises a plurality of probes each of which specifically binds to a marker associated with lung cancer, wherein:
   (a) the pattern of binding of the component probes of the panel to cells in a cytology sample is diagnostic for the presence of lung cancer, and
   (b) said plurality of probes comprises probes that bind to cyclin A, SP-B, HERA, and ER-related(p29).

4. A cell-based method for detecting lung cancer, comprising contacting cells from a cytology sample on one or more microscope slides with a panel comprising a plurality of probes and analyzing the pattern of binding of the component probes of the panel to cells in said cytology sample to detect lung cancer,
   wherein said plurality of probes comprises a probe that binds to cyclin A and at least one probe that binds to a marker selected from the group consisting of SP-B, HERA, ER-related(p29).

* * * * *